United States Patent
Cobaugh

(10) Patent No.: US 12,188,060 B2
(45) Date of Patent: Jan. 7, 2025

(54) MESSENGER RNA ENCODING Cas9 FOR USE IN GENOME-EDITING SYSTEMS

(71) Applicant: CRISPR THERAPEUTICS AG, Zug (CH)

(72) Inventor: Christian Cobaugh, Newton, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 347 days.

(21) Appl. No.: 17/319,291

(22) Filed: May 13, 2021

(65) Prior Publication Data

US 2021/0355463 A1 Nov. 18, 2021

Related U.S. Application Data

(60) Provisional application No. 63/025,755, filed on May 15, 2020.

(51) Int. Cl.
| | |
|---|---|
| C12N 9/22 | (2006.01) |
| A61K 9/51 | (2006.01) |
| A61K 31/7088 | (2006.01) |
| C12N 15/11 | (2006.01) |
| C12N 15/90 | (2006.01) |
| A61K 48/00 | (2006.01) |

(52) U.S. Cl.
CPC .............. *C12N 9/22* (2013.01); *A61K 9/5123* (2013.01); *A61K 31/7088* (2013.01); *C12N 15/11* (2013.01); *C12N 15/907* (2013.01); *A61K 48/00* (2013.01); *C12N 2310/20* (2017.05); *C12N 2320/32* (2013.01); *C12N 2800/80* (2013.01)

(58) Field of Classification Search
CPC ........ C12N 9/22; C12N 15/11; C12N 15/907; C12N 2310/20; C12N 2320/32; C12N 2800/80; C12N 15/102; C12N 15/88; C12N 2310/335; C12N 15/111; A61K 9/5123; A61K 31/7088; A61K 48/00; A61K 48/005
See application file for complete search history.

(56) References Cited

U.S. PATENT DOCUMENTS

| | | |
|---|---|---|
| 4,373,071 A | 2/1983 | Itakura |
| 4,401,796 A | 8/1983 | Itakura |
| 4,415,732 A | 11/1983 | Caruthers et al. |

(Continued)

FOREIGN PATENT DOCUMENTS

| | | |
|---|---|---|
| EP | 2518144 A1 | 10/2012 |
| EP | 2578685 B1 | 4/2019 |

(Continued)

OTHER PUBLICATIONS

Gould et al. 2014. Computational tools and algorithms for designing customized synthetic genes. Front. Bioengineer. Biotechnol. 2:41 (Year: 2014).*

(Continued)

*Primary Examiner* — Kimberly Chong
*Assistant Examiner* — Ruth Sophia Arieti
(74) *Attorney, Agent, or Firm* — Casimir Jones, S.C.; J. Mitchell Jones

(57) ABSTRACT

The present disclosure provides optimized mRNAs encoding a site-directed endonuclease for use in a CRISPR/Cas system. Also provided herein are delivery systems for use of the CRISPR/Cas system in methods of in vivo and ex vivo genome editing.

15 Claims, 7 Drawing Sheets

Specification includes a Sequence Listing.

(56) References Cited

U.S. PATENT DOCUMENTS

| | | |
|---|---|---|
| 4,458,066 A | 7/1984 | Caruthers et al. |
| 4,500,707 A | 2/1985 | Caruthers et al. |
| 4,668,777 A | 5/1987 | Caruthers et al. |
| 4,973,679 A | 11/1990 | Caruthers et al. |
| 5,013,556 A | 5/1991 | Woodle et al. |
| 5,034,506 A | 7/1991 | Summerton et al. |
| 5,047,524 A | 9/1991 | Andrus et al. |
| 5,132,418 A | 7/1992 | Caruthers et al. |
| 5,153,319 A | 10/1992 | Caruthers et al. |
| 5,262,530 A | 11/1993 | Andrus et al. |
| 5,700,642 A | 12/1997 | Monforte et al. |
| 6,027,726 A | 2/2000 | Ansell |
| 7,561,972 B1 | 7/2009 | Welch et al. |
| 7,561,973 B1 | 7/2009 | Welch et al. |
| 8,126,653 B2 | 2/2012 | Welch et al. |
| 8,401,798 B2 | 3/2013 | Welch et al. |
| 8,664,194 B2 | 3/2014 | De Fougerolles |
| 8,680,069 B2 | 3/2014 | De Fougerolles |
| 8,691,750 B2 | 4/2014 | Constien et al. |
| 8,754,062 B2 | 6/2014 | De Fougerolles |
| 8,999,380 B2 | 4/2015 | Bancel |
| 9,050,297 B2 | 6/2015 | Chakraborty |
| 9,061,059 B2 | 6/2015 | Chakraborty |
| 9,089,604 B2 | 7/2015 | Chakraborty |
| 9,095,552 B2 | 8/2015 | Chakraborty |
| 9,107,886 B2 | 8/2015 | Chakraborty |
| 9,114,113 B2 | 8/2015 | Chakraborty |
| 9,149,506 B2 | 10/2015 | Chakraborty |
| 9,186,372 B2 | 11/2015 | De Fougerolles |
| 9,192,651 B2 | 11/2015 | Chakraborty |
| 9,216,205 B2 | 12/2015 | Chakraborty |
| 9,220,755 B2 | 12/2015 | Chakraborty |
| 9,220,792 B2 | 12/2015 | Chakraborty |
| 9,221,891 B2 | 12/2015 | Bancel |
| 9,233,141 B2 | 1/2016 | Chakraborty |
| 9,254,311 B2 | 2/2016 | Bancel |
| 9,255,129 B2 | 2/2016 | Chakraborty |
| 9,271,996 B2 | 3/2016 | De Fougerolles |
| 9,283,287 B2 | 3/2016 | Chakraborty |
| 9,295,689 B2 | 3/2016 | De Fougerolles |
| 9,301,993 B2 | 4/2016 | Chakraborty |
| 9,303,079 B2 | 4/2016 | Chakraborty |
| 9,428,535 B2 | 8/2016 | De Fougerolles |
| 9,504,734 B2 | 11/2016 | Bancel |
| 9,572,896 B2 | 2/2017 | Bancel |
| 9,572,897 B2 | 2/2017 | Bancel |
| 9,587,003 B2 | 3/2017 | Bancel |
| 9,597,380 B2 | 3/2017 | Chakraborty |
| 9,675,668 B2 | 6/2017 | Bancel |
| 9,782,462 B2 | 10/2017 | Bancel |
| 9,814,760 B2 | 11/2017 | Bancel |
| 9,827,332 B2 | 11/2017 | Bancel |
| 9,828,416 B2 | 11/2017 | Bancel |
| 9,878,056 B2 | 1/2018 | Bancel |
| 9,950,068 B2 | 4/2018 | De Fougerolles |
| 10,155,029 B2 | 12/2018 | Chakraborty |
| 10,385,106 B2 | 8/2019 | De Fougerolles |
| 10,463,751 B2 | 11/2019 | De Fougerolles |
| 10,493,167 B2 | 12/2019 | De Fougerolles |
| 10,501,512 B2 | 12/2019 | De Fougerolles |
| 10,501,513 B2 | 12/2019 | De Fougerolles |
| 10,577,403 B2 | 3/2020 | De Fougerolles |
| 10,583,203 B2 | 3/2020 | De Fougerolles |
| 10,703,789 B2 | 7/2020 | De Fougerolles |
| 10,724,050 B1 | 7/2020 | Doering |
| 10,772,975 B2 | 9/2020 | Bancel |
| 10,898,574 B2 | 1/2021 | De Fougerolles |
| 10,925,935 B2 | 2/2021 | Chakraborty |
| 11,564,998 B2 | 1/2023 | De Fougerolles |
| 2004/0142025 A1 | 7/2004 | MacLachlan et al. |
| 2005/0222064 A1 | 10/2005 | Vargeese et al. |
| 2005/0235369 A1 | 10/2005 | Choo |
| 2006/0240554 A1 | 10/2006 | Chen |
| 2006/0292572 A1 | 12/2006 | Stuart |
| 2007/0042031 A1 | 2/2007 | MacLachlan et al. |
| 2007/0161031 A1 | 7/2007 | Trinklein |
| 2008/0220983 A1 | 9/2008 | Trinklein |
| 2011/0182980 A1 | 7/2011 | Yagi |
| 2012/0065252 A1 | 3/2012 | Schrum |
| 2022/0364078 A1* | 11/2022 | Cheng .................... C07H 21/02 |

FOREIGN PATENT DOCUMENTS

| | | | |
|---|---|---|---|
| EP | 3019619 B1 | 8/2021 | |
| EP | 2791160 B1 | 3/2022 | |
| EP | 3611266 B1 | 11/2022 | |
| GB | 2378445 A | 2/2003 | |
| WO | WO2001/057182 | 8/2001 | |
| WO | 2001/83692 A2 | 11/2001 | |
| WO | WO2002/000677 | 1/2002 | |
| WO | WO2002/018424 | 3/2002 | |
| WO | WO2003/054166 | 7/2003 | |
| WO | WO2004/042054 | 5/2004 | |
| WO | WO2004/108883 | 12/2004 | |
| WO | 2005/001248 A1 | 1/2005 | |
| WO | WO2005/028617 | 3/2005 | |
| WO | WO2006/023491 | 3/2006 | |
| WO | WO2006/028967 | 3/2006 | |
| WO | 2007/024708 A2 | 3/2007 | |
| WO | WO2008077592 | 7/2008 | |
| WO | WO2008/112127 | 9/2008 | |
| WO | WO2009/074968 | 6/2009 | |
| WO | WO2010/037539 | 4/2010 | |
| WO | WO2011/005861 | 1/2011 | |
| WO | WO2011/008260 | 1/2011 | |
| WO | WO2011/150241 | 12/2011 | |
| WO | 2012/135805 A2 | 10/2012 | |
| WO | WO2012/135805 | 10/2012 | |
| WO | 2013/052523 A1 | 4/2013 | |
| WO | WO2013/071047 | 5/2013 | |
| WO | 2013/086354 A1 | 6/2013 | |
| WO | WO2013/082519 | 6/2013 | |
| WO | WO2013/090648 | 6/2013 | |
| WO | 2013/116126 A1 | 8/2013 | |
| WO | 2013/151666 A2 | 10/2013 | |
| WO | 2013/151736 A2 | 10/2013 | |
| WO | WO2014140211 | 9/2014 | |
| WO | WO2014/165825 | 10/2014 | |
| WO | WO2015/006498 | 1/2015 | |
| WO | 2015/052133 A1 | 4/2015 | |
| WO | 2017/181107 A2 | 10/2017 | |
| WO | WO2018111967 | 6/2018 | |
| WO | 2018/144775 A1 | 8/2018 | |
| WO | WO-2018183808 A1 * | 10/2018 | ......... C12N 15/1131 |
| WO | 2019/067910 A1 | 4/2019 | |
| WO | WO-2019140116 A2 * | 7/2019 | ......... C07K 14/1825 |
| WO | 2019/191341 A1 | 10/2019 | |
| WO | 2020/056304 A1 | 3/2020 | |

OTHER PUBLICATIONS

ThermoFisher 2016-GeneArt CRISPR Nuclease mRNA Complete webpage and manual (Year: 2016).*

Parr et al. 2020. N1-Methylpseudouridine substitution enhances the performance of synthetic mRNA switches in cells. Nuc. Acids Res. 48[6]:e35 (is on IDS) (Year: 2020).*

Pouton et al. 2007. Targeted delivery to the nucleus. Adv. Drug Deliv. Rev. 59:698-717 (Year: 2007).*

Fayssoil et al. 2010. Cardiomyopathy in Duchenne muscular dystrophy: pathogenesis and therapeutics. Heart Fail. Rev. 15:103-107 (Year: 2010).*

Ran et al. 2013. Genome engineering using the CRISPR-Cas9 system. Nat. Protocol. 8[11]:2281-2308 (Year: 2013).*

Rubel et al. 2013. A brief history of hair cell regeneration research and speculations on the future. Hearing Res. 297:42-51 (Year: 2013).*

Murray et al. 2015. Mutations in the NHEJ Component XRCC4 Cause Primordial Dwarfism. Am. J. Hum Genet. 96:412-424 (Year: 2015).*

Cox et al. 2015. Therapeutic genome editing: prospects and challenges. Nat. Med. 21[2]:121-131 (Year: 2015).*

(56) References Cited

OTHER PUBLICATIONS

Kaiser. 2016. The gene editor CRISPR won't fully fix sick people anytime soon. Here's why. Science AAAS (Year: 2016).*
Wyatt and Ramsden. 2020. CRISPR 101: Non-Homologous End Joining. Addgene Blog. Available online at addgene.org. Accessed May 15, 2024 (Year: 2020).*
Jaslow. 2023. Scientists Regenerate Hair Cells that Enable Hearing. Harvard Medical School News & Research. Available online at Harvard.edu. Accessed on May 15, 2024 (Year: 2023).*
Medline. Help me understand genetics: Variants and health. Available online at medlineplus.gov. Accessed on May 15, 2024 (Year: 2024).*
CDC. If no known FH-causing mutation. Available online at cdc.gov. Accessed on May 15, 2024 (Year: 2024).*
Wikipedia. Scurvy. Available online at Wikipedia.org. Accessed on May 15, 2024 (Year: 2024).*
Heath et al., "Covalent Attachment of Proteins to Liposomes," Methods in Enzymology 1987, 149, 111-119.
Abra et al., The next generation of liposome delivery systems: recent experience with tumor-targeted, sterically-stabilized immunoliposomes and active-loading gradients, J. Liposome Res., 12:1-3 (2002).
Akinc et al., A combinatorial library of lipid-like materials for delivery of RNAi therapeutics, Nat. Biotechnol., 26(5):561-569 (2008).
Akinc et al., Development of lipidoid-siRNA formulations for systemic delivery to the liver, Mol. Ther., 17(5):872-879 (2009).
Allen et al., A new strategy for attachment of antibodies to sterically stabilized liposomes resulting in efficient targeting to cancer cells, Biochim. Biophys. Acta., 1237(2):99-108 (1995).
Altschul et al., Basic local alignment search tool, J. Mol. Biol., 215(3):403-410 (1990).
Anderson et al., Nucleoside modifications in RNA limit activation of 2'-5'-oligoadenylate synthetase and increase resistance to cleavage by RNase L, Nucleic Acids Res., 39(21):9329-38 (2011).
Blume et al., Specific targeting with poly(ethylene glycol)-modified liposomes: coupling of homing devices to the ends of the polymeric chains combines effective target binding with long circulation times, Biochim. Biophys. Acta., 1149(1):180-184 (1993).
Brinkman et al., Easy quantitative assessment of genome editing by sequence trace decomposition, Nucleic Acids Res., 42(22):e168 (2014).
Chang et al., Modification of DNA ends can decrease end joining relative to homologous recombination in mammalian cells, Proc. Natl. Acad. Sci. USA., 84(14):4959-4963 (1987).
Chiang et al., Sequence-specific modifications enhance the broad-spectrum antiviral response activated by RIG-I Agonists, J. Virol., 89(15):8011-25 (2015).
Defrees et al., Sialyl lewis X liposomes as a multivalent ligand and inhibitor of E-selectin mediated cellular adhesion, J. Am. Chem. Soc., 118:6101-6104 (1996).
Deltcheva et al., CRISPR RNA maturation by trans-encoded small RNA and host factor RNase III, Nature, 471:602-607 (2011).
Goodchild, Conjugates of oligonucleotides and modified oligonucleotides: a review of their synthesis and properties, Bioconjugate Chem., 1(3):165-87 (1990).
International Application No. PCT/IB2021/054115, International Search Report and Written Opinion, mailed Aug. 31, 2021.
Jinek et al., A programmable dual-RNA-guided DNA endonuclease in adaptive bacterial immunity, Science, 337(6096):816-821 (2012).
Kariko et al., Suppression of RNA recognition by Toll-like receptors: the impact of nucleoside modification and the evolutionary origin of RNA, Immunity, 23(2):165-75 (2005).
Kirpotin et al., Liposomes with detachable polymer coating: destabilization and fusion of dioleoylphosphatidylethanolamine vesicles triggered by cleavage of surface-grafted poly(ethylene glycol), FEBS Letters, 388:115-118 (1996).
Klibanov et al., Long-circulating liposomes: development and perspectives, Journal of Liposome Research, 2(3):321-334 (1992).
Laughlin et al., Cloning of infectious adeno-associated virus genomes in bacterial plasmids, Gene., 23(1):65-73 (1983).
Leonetti et al., Antibody-targeted liposomes containing oligodeoxyribonucleotides complementary to viral RNA selectively inhibit viral replication, Proc. Natl. Acad. Sci. USA., 87(7):2448-2451 (1990).
Liu et al., Designer lipids advance systemic siRNA delivery, Molecular Therapy, 18(4):669-670 (2010).
Love et al., Lipid-like materials for low-dose, in vivo gene silencing, Proc. Natl. Acad. Sci. USA., 107(5):1864-1869 (2010).
Mahon et al., Combinatorial approach to determine functional group effects on lipidoid-mediated siRNA delivery, Bioconjug. Chem., 21(8):1448-1454 (2010).
Mesmaeker et al., Antisense oligonucleotides, Acc. Chem. Res., 28(9):366-374 (1995).
Murugaiah et al., Reversed-phase high-performance liquid chromatography method for simultaneous analysis of two liposome-formulated short interfering RNA duplexes, Analytical Biochemistry, 401(1):61-7 (2010).
Nehls et al., Two genetically separable steps in the differentiation of thymic epithelium, Science, 272:886-889 (1996).
Nielsen et al., Sequence-selective recognition of DNA by strand displacement with a thymine-substituted polyamide, Science, 254:1497-1500 (1991).
Parr et al., N1-Methylpseudouridine substitution enhances the performance of synthetic mRNA switches in cells, Nucl. Acids Res., 48(6):e35 (2020).
Parr et al., N1-Methylpseudouridine substitution enhances the performance of synthetic mRNA switches in cells, Supp. Infor., 1-19 (2020).
Reese, Oligo- and poly-nucleotides: 50 years of chemical synthesis, Organic & Biomolecular Chemistry, 3(21):3851-68 (2005).
Renneisen et al., Inhibition of expression of human immunodeficiency virus-1 in vitro by antibody-targeted liposomes containing antisense RNA to the env region, J. Bio. Chem., 265:16337-16342 (1990).
Runge et al., In vivo ligands of MDA5 and RIG-I in measles virus-infected cells, PLoS Pathog., 10(4):e1004081 (2014).
Saito et al., Innate immunity induced by composition-dependent RIG-I recognition of hepatitis C virus RNA, Nature, 454(7203):523-7 (2008).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Sapra et al., Ligand-targeted liposomal anticancer drugs, Prog. Lipid Res., 42(5):439-62 (2003).
Schroeder et al., Lipid-based nanotherapeutics for siRNA delivery, J. Intern. Med., 267(1):9-21 (2010).
Senapathy et al., Molecular cloning of adeno-associated virus variant genomes and generation of infectious virus by recombination in mammalian cells, J. Biol. Chem., 259:4661-4666 (1984).
Siegwart et al., Combinatorial synthesis of chemically diverse core-shell nanoparticles for intracellular delivery, Proc. Natl. Acad. Sci. USA., 108(32): 12996-3001 (2011).
Verma et al., Modified oligonucleotides: synthesis and strategy for users, Annual Review of Biochemistry, 67:99-134 (1998).
Wang et al., Cyclohexene nucleic acids (CeNA):? serum stable oligonucleotides that activate RNase H and increase duplex stability with complementary RNA, J. Am. Chem. Soc., 122(36):8595-8602 (2000).
Warren et al., Highly efficient reprogramming to pluripotency and directed differentiation of human cells with synthetic modified mRNA, Cell Stem Cell., 7(5):618-30 (2010).
Zalipsky et al., Long circulating, cationic liposomes containing amino-PEG-phosphatidylethanolamine, FEBS Letters, 353(1):71-74 (1994).
Zalipsky, Synthesis of an end-group functionalized polyethylene glycol-lipid conjugate for preparation of polymer-grafted liposomes, Bioconjugate Chemistry, 4(4):296-299 (1993).
U.S. Appl. No. 61/808,594, filed Apr. 4, 2013, Kiran Musunuru.
U.S. Appl. No. 61/844,333, filed Jul. 9, 2013, Kiran Musunuru.

(56) References Cited

OTHER PUBLICATIONS

Agris et al., "Thermodynamic contribution of nucleoside modifications to yeast tRNA$^{Phe}$ anticodon stem loop analogs," Acta Biochimica Polonica 1999, 46(1), 163-172.
Akinc et al., "Development of lipidoid-siRNA formulations for systemic delivery to the liver," Molecular Therapy 2009, 17(5), 872-879.
Andries et al., "N1-methylpseudouridine-incorporated mRNA outperforms pseudouridine-incorporated mRNA by providing enhanced protein expression and reduced immunogenicity in mammalian cell lines and mice," Journal of Controlled Release 2015, 217, 337-344.
Barrangou, "RNA-mediated programmable DNA cleavage," Nature Biotechnology 2012, 30(9), 836-838.
Blancafort et al., "Designing transcription factor architectures for drug discovery," Molecular Pharmacology 2004, 66(6), 1361-1371.
Brouns, "A Swiss army knife of immunity," Science 2012, 337(6096), 808-809.
Carroll, "Genome engineering with zinc-finger nucleases," Genetics 2011, 188(4), 773-782.
Carroll, "Progress and prospects: zinc-finger nucleases as gene therapy agents," Gene Therapy 2008, 15(22), 1463-1468.
Chang et al., "Genome editing with RNA-guided Cas9 nuclease in zebrafish embryos," Cell Research 2013, 23(4), 465-472.
Cho et al., "Targeted genome engineering in human cells with the Cas9 RNA-guided endonuclease," Nature Biotechnology 2013, 31(3), 230-232.
Christian et al., "Targeting DNA double-strand breaks with TAL effector nucleases," Genetics 2010, 186(2), 757-761.
Chylinski et al., "The tracrRNA and Cas9 families of type II CRISPR-Cas immunity systems," RNA Biology 2013, 10(5), 726-737.
Cong et al., "Multiplex genome engineering using CRISPR/Cas systems," Science 2013, 339(6121), 819-823.
D100—Exhibit 7—sequence alignment and analysis of SEQ ID No. 9 submitted in Grounds of Opposition to EP 3019619 B1 on May 25, 2022, in 4 pages.
D101—Exhibit 8—sequence alignment and analysis of SEQ ID No. 1 submitted in Grounds of Opposition to EP 3019619 B1 on May 25, 2022, in 10 pages.
D102—Exhibit 9—sequence alignment and analysis of SEQ ID No. 2 submitted in Grounds of Opposition to EP 3019619 B1 on May 25, 2022, in 10 pages.
D103—Exhibit 10—sequence alignment and analysis of SEQ ID No. 3 submitted in Grounds of Opposition to EP 3019619 B1 on May 25, 2022, in 6 pages.
D104—Exhibit 11—sequence alignment and analysis of SEQ ID No. 4 submitted in Grounds of Opposition to EP 3019619 B1 on May 25, 2022, in 4 pages.
D105—Exhibit 12—sequence alignment and analysis of SEQ ID No. 5 submitted in Grounds of Opposition to EP 3019619 B1 on May 25, 2022, in 4 pages.
D106—Exhibit 13—sequence alignment and analysis of SEQ ID No. 6 submitted in Grounds of Opposition to EP 3019619 B1 on May 25, 2022, in 5 pages.
D107—Exhibit 14—sequence alignment and analysis of SEQ ID No. 111 submitted in Grounds of Opposition to EP 3019619 B1 on May 25, 2022, in 10 pages.
D108—Exhibit 15—sequence alignment and analysis of SEQ ID No. 112 submitted in Grounds of Opposition to EP 3019619 B1 on May 25, 2022, in 10 pages.
D109—Exhibit 16—sequence alignment and analysis of SEQ ID No. 55 submitted in Grounds of Opposition to EP 3019619 B1 on May 25, 2022, in 5 pages.
D110—Exhibit 17—sequence alignment and analysis of SEQ ID No. 56 submitted in Grounds of Opposition to EP 3019619 B1 on May 25, 2022, in 5 pages.
D111—Exhibit 18—sequence alignment and analysis of SEQ ID No. 61 submitted in Grounds of Opposition to EP 3019619 B1 on May 25, 2022, in 3 pages.
D112—Exhibit 19—sequence alignment and analysis of SEQ ID No. 62 submitted in Grounds of Opposition to EP 3019619 B1 on May 25, 2022, in 4 pages.
D113—Exhibit 20—sequence alignment and analysis of SEQ ID No. 63 submitted in Grounds of Opposition to EP 3019619 B1 on May 25, 2022, in 4 pages.
D114—Exhibit 21—sequence alignment and analysis of SEQ ID No. 64 submitted in Grounds of Opposition to EP 3019619 B1 on May 25, 2022, in 4 pages.
D115—Exhibit 22—sequence alignment and analysis of SEQ ID No. 65 submitted in Grounds of Opposition to EP 3019619 B1 on May 25, 2022, in 4 pages.
D116—Exhibit 23—sequence alignment and analysis of SEQ ID No. 110 submitted in Grounds of Opposition to EP 3019619 B1 on May 25, 2022, in 5 pages.
D117—Exhibit 24—sequence alignment and analysis of SEQ ID No. 51 submitted in Grounds of Opposition to EP 3019619 B1 on May 25, 2022, in 5 pages.
D118—Exhibit 25—sequence alignment and analysis of SEQ ID No. 52 submitted in Grounds of Opposition to EP 3019619 B1 on May 25, 2022, in 5 pages.
D119—Exhibit 26—sequence alignment and analysis of SEQ ID No. 53 submitted in Grounds of Opposition to EP 3019619 B1 on May 25, 2022, in 5 pages.
D120—Exhibit 27—sequence alignment and analysis of SEQ ID No. 54 submitted in Grounds of Opposition to EP 3019619 B1 on May 25, 2022, in 5 pages.
D121—Exhibit 28—sequence alignment and analysis of Cas9 used in Wang (D18) submitted in Grounds of Opposition to EP 3019619 B1 on May 25, 2022, in 5 pages.
D122—Exhibit 29—sequence alignment and analysis of SEQ ID No. 90 submitted in Grounds of Opposition to EP 3019619 B1 on May 25, 2022, in 2 pages.
D123—Exhibit 30—sequence alignment and analysis of SEQ ID No. 71 submitted in Grounds of Opposition to EP 3019619 B1 on May 25, 2022, in 1 page.
D124—Exhibit 31—sequence alignment and analysis of SEQ ID No. 18 submitted in Grounds of Opposition to EP 3019619 B1 on May 25, 2022, in 1 page.
D125—Exhibit 32—sequence alignment and analysis of SEQ ID No. 23 submitted in Grounds of Opposition to EP 3019619 B1 on May 25, 2022, in 5 pages.
D126—Exhibit 33—sequence alignment and analysis of SEQ ID No. 25 submitted in Grounds of Opposition to EP 3019619 B1 on May 25, 2022, in 2 pages.
D127—Exhibit 34—sequence alignment and analysis of SEQ ID No. 26 submitted in Grounds of Opposition to EP 3019619 B1 on May 25, 2022, in 1 page.
D128—Exhibit 35—sequence alignment and analysis of SEQ ID No. 27 submitted in Grounds of Opposition to EP 3019619 B1 on May 25, 2022, in 1 page.
D129—Exhibit 36—sequence alignment and analysis of SEQ ID No. 28 submitted in Grounds of Opposition to EP 3019619 B1 on May 25, 2022, in 3 pages.
D130—Exhibit 37—sequence alignment and analysis of SEQ ID No. 30 submitted in Grounds of Opposition to EP 3019619 B1 on May 25, 2022, in 2 pages.
D131—Exhibit 38—sequence alignment and analysis of SEQ ID No. 31 submitted in Grounds of Opposition to EP 3019619 B1 on May 25, 2022, in 1 page.
D132—Exhibit 39—sequence alignment and analysis of SEQ ID No. 32 submitted in Grounds of Opposition to EP 3019619 B1 on May 25, 2022, in 3 pages.
D133—Exhibit 40—sequence alignment and analysis of SEQ ID No. 33 submitted in Grounds of Opposition to EP 3019619 B1 on May 25, 2022, in 2 pages.
D134—Exhibit 41—sequence alignment and analysis of SEQ ID No. 34 submitted in Grounds of Opposition to EP 3019619 B1 on May 25, 2022, in 2 pages.
D61—Experimental data filed by the then Applicant during examination proceedings on Jul. 18, 2017, submitted in Grounds of Opposition to EP 3019619 B1 on May 25, 2022, in 2 pages.

(56) References Cited

OTHER PUBLICATIONS

D94—Exhibit 1—timeline of relevant dates submitted in Grounds of Opposition to EP 3019619 B1 on May 25, 2022, in 1 page.
D95—Exhibit 2—sequence alignment and analysis of SEQ ID No. 298 of WO 2014/165825 (D36) submitted in Grounds of Opposition to EP 3019619 B1 on May 25, 2022, in 4 pages.
D96—Exhibit 3—sequence alignment and analysis of SEQ ID No. 298 of WO 2015/006498 (D39) submitted in Grounds of Opposition to EP 3019619 B1 on May 25, 2022, in 4 pages.
D97—Exhibit 4—summary of characteristics of the Cas9 sequences specified in the claims submitted in Grounds of Opposition to EP 3019619 B1 on May 25, 2022, in 2 pages.
D98—Exhibit 5—sequence alignment and analysis of SEQ ID No. 7 submitted in Grounds of Opposition to EP 3019619 B1 on May 25, 2022, in 3 pages.
D99—Exhibit 6—sequence alignment and analysis of SEQ ID No. 8 submitted in Grounds of Opposition to EP 3019619 B1 on May 25, 2022, in 3 pages.
Dai et al., "The transcription factors GATA4 and dHAND physically interact to synergistically activate cardiac gene expression through a p300-dependent mechanism," Journal of Biological Chemistry 2002, 277(27), 24390-24398.
Deltcheva et al., "CRISPR RNA maturation by trans-encoded small RNA and host factor RNase III," Nature 2011, 471(7340), 602-607.
DiCarlo et al., "Genome engineering in Saccharomyces cerevisiae using CRISPR-Cas systems," Nucleic Acids Research 2013, 41(7), 4336-4343.
Freitas & Cunha, "Mechanisms and signals for the nuclear import of proteins," Current Genomics 2009, 10(8), 550-557.
Fu et al., "High-frequency off-target mutagenesis induced by CRISPR-Cas nucleases in human cells," Nature Biotechnology 2013, 31(9), 822-826.
Gascón et al., "Non-viral delivery systems in gene therapy," Gene Therapy-Tools and Potential Applications. IntechOpen 2013, in 31 pages.
Gilbert et al., "CRISPR-mediated modular RNA-guided regulation of transcription in eukaryotes," Cell 2013, 154(2), 442-451.
Gratz et al., "Genome engineering of Drosophila with the CRISPR RNA-guided Cas9 nuclease," Genetics 2013, 194(4), 1029-1035.
Grounds of Opposition submitted to European Patent Office to European patent No. EP 3019619 B1 on May 25, 2022, in 133 pages.
Harper et al., "Sin3 corepressor function in Myc-induced transcription and transformation," Proceedings of the National Academy of Sciences 1996, 93(16), 8536-8540.
Heyes et al., "Cationic lipid saturation influences intracellular delivery of encapsulated nucleic acids," Journal of Controlled Release 2005, 107(2), 276-287.
Hwang et al., "Efficient genome editing in zebrafish using a CRISPR-Cas system," Nature Biotechnology 2013, 31(3), 227-229.
Jinek et al., "A programmable dual-RNA-guided DNA endonuclease in adaptive bacterial immunity," Science 2012, 337(6096), 816-821.
Jinek et al., "RNA-programmed genome editing in human cells," eLife 2013, 2, in 9 pages.
Joung & Sander, "TALENs: a widely applicable technology for targeted genome editing," Nature Reviews Molecular Cell Biology 2013, 14(1), 49-55.
Kalejs & Erenpreisa, "Cancer/testis antigens and gametogenesis: a review and "brain-storming" session," Cancer Cell International 2005, 5, 1-11.
Karikó et al., "Incorporation of pseudouridine into mRNA yields superior nonimmunogenic vector with increased translational capacity and biological stability," Molecular Therapy 2008, 16(11), 1833-1840.
Khorsandi et al., "Minimally invasive and selective hydrodynamic gene therapy of liver segments in the pig and human," Cancer Gene Therapy 2008, 15(4), 225-230.
Liu & Huang, "Designer lipids advance systemic siRNA delivery," Molecular Therapy 2010, 18(4), 669-670.

Maeder et al., "CRISPR RNA-guided activation of endogenous human genes," Nature Methods 2013, 10(10), 977-979.
Makarova et al., "Evolution and classification of the CRISPR-Cas systems," Nature Reviews Microbiology 2011, 9(6), 467-477.
Makarova et al., "Unification of Cas protein families and a simple scenario for the origin and evolution of CRISPR-Cas systems," Biology Direct 2011, 6, 1-27.
Mali et al., "RNA-guided human genome engineering via Cas9," Science 2013, 339(6121), 823-826.
McCaffrey, "The Buzz on the Cut: From Dream to Reality," trilinkbiotech.com 2020, in 8 pages.
Miller et al., "A Tale nuclease architecture for efficient genome editing," Nature Biotechnology 2011, 29(2), 143-148.
Murugaiah et al., "Reversed-phase high-performance liquid chromatography method for simultaneous analysis of two liposome-formulated short interfering RNA duplexes," Analytical Biochemistry 2010, 401(1), 61-67.
Opposition proceedings (observations) submitted to European Patent Office on Dec. 15, 2022 in European patent No. EP 3019619 B1, in 37 pages.
Pardi et al., "In vitro transcription of long RNA containing modified nucleosides," Synthetic Messenger RNA and Cell Metabolism Modulation: Methods and Protocols 2013, 29-42.
Patterson et al., "Codon optimization of bacterial luciferase (lux) for expression in mammalian cells," Journal of Industrial Microbiology and Biotechnology 2005, 32(3), 115-123.
Perche et al., "Enhancement of dendritic cells transfection in vivo and of vaccination against B16F10 melanoma with mannosylated histidylated lipopolyplexes loaded with tumor antigen messenger RNA," Nanomedicine: Nanotechnology, Biology and Medicine 2011, 7(4), 445-453.
Perez-Pinera et al., "RNA-guided gene activation by CRISPR-Cas9-based transcription factors," Nature Methods 2013, 10(10), 973-976.
Planey et al., "Inhibition of glucocorticoid-induced apoptosis in 697 pre-B lymphocytes by the mineralocorticoid receptor N-terminal domain," Journal of Biological Chemistry 2002, 277(44), 42188-42196.
Qi et al., "Repurposing CRISPR as an RNA-guided platform for sequence-specific control of gene expression," Cell 2013, 152(5), 1173-1183.
Raymond & Soriano, "High-efficiency FLP and φC31 site-specific recombination in mammalian cells," PloS One 2007, 2(1), in 4 pages.
Response to the observations filed by the Patentee on Dec. 15, 2022 submitted to European Patent Office on May 16, 2023 in European patent No. EP 3019619 B1, in 21 pages.
Sanjana et al., "A transcription activator-like effector toolbox for genome engineering," Nature Protocols 2012, 7(1), 171-192.
Shen et al., "Generation of gene-modified mice via Cas9/RNA-mediated gene targeting," Cell Research 2013, 23(5), 720-723.
Su et al., "In vitro and in vivo mRNA delivery using lipid-enveloped pH-responsive polymer nanoparticles," Molecular Pharmaceutics 2011, 8(3), 774-787.
Tavernier et al., "mRNA as gene therapeutic: how to control protein expression," Journal of Controlled Release 2011, 150(3), 238-247.
Urnov et al., "Genome editing with engineered zinc finger nucleases," Nature Reviews Genetics 2010, 11(9), 636-646.
Urnov et al., "Highly efficient endogenous human gene correction using designed zinc-finger nucleases," Nature 2005, 435(7042), 646-651.
Villion & Moineau, "The double-edged sword of CRISPR-Cas systems," Cell Research 2013, 23(1), 15-17.
Wang et al., "One-step generation of mice carrying mutations in multiple genes by CRISPR/Cas-mediated genome engineering," Cell 2013, 153(4), 910-918.
Wang et al., "Systemic delivery of modified mRNA encoding herpes simplex virus 1 thymidine kinase for targeted cancer gene therapy," Molecular Therapy 2013, 21(2), 358-367.
Warren et al., "Highly efficient reprogramming to pluripotency and directed differentiation of human cells with synthetic modified mRNA," Cell Stem Cell 2010, 7(5), 618-630.

(56) References Cited

OTHER PUBLICATIONS

Xu, "The next generation biotechnology for apple improvement and beyond: The CRISP/cas9 story," New York Fruit Quarterly 2013, 21, 19-22.

Yagi et al., "Sustained ex vivo expansion of hematopoietic stem cells mediated by thrombopoietin" Proceedings of the National Academy of Sciences 1999, 96(14), 8126-8131.

Yamamoto et al., "Current prospects for mRNA gene delivery," European Journal of Pharmaceutics and Biopharmaceutics 2009, 71(3), 484-489.

Yarian et al., "Structural and functional roles of the N1-and N3-protons of ψ at tRNA's position 39," Nucleic Acids Research 1999, 27(17), 3543-3549.

Young et al., "Recombinant protein expression and purification: a comprehensive review of affinity tags and microbial applications," Biotechnology Journal 2012, 7(5) 620-634.

Yu et al., "Highly efficient genome modifications mediated by CRISPR/Cas9 in *Drosophila*," Genetics 2013, 195(1), 289-291.

Zhang et al., "Efficient construction of sequence-specific TAL effectors for modulating mammalian transcription," Nature Biotechnology 2011, 29(2), 149-153.

Albretsen, Catrine, et al. "Applications of magnetic beads with covalently attached oligonucleotides in hybridization: isolation and detection of specific measles virus mRNA from a crude cell lysate." Analytical biochemistry 189.1 (1990): 40-50.

Bosnes, et al. "Solid-phase in vitro Transcription and mRNA Purification using DynabeadsTM Superparamagnetic Beads." Thermo Fisher Scientific, 2007.

International preliminary report on patentability dated Nov. 14, 2023 in Patent Application No. PCT/US2022/028727.

International Search Report and Written opinion dated Aug. 29, 2022 in Patent Application No. PCT/US2022/028727.

Miller, Shannon M., et al. "Continuous evolution of SpCas9 variants compatible with non-G PAMs." Nature biotechnology 38.4 (2020): 471-481.

Svec, F., and T. B. Tennikova. "Polymeric Separation Media for Chromatography of Biopolymers in a Novel Shape-Macroporous Membranes." Journal of Bioactive and Compatible Polymers 6.4 (1991): 393-405.

Svec, F., M. Jelinkova, and E. Votavova. "Reactive macroporous membranes based on glycidyl methacrylate-ethylene dimethacrylate copolymer for high-performance membrane chromatography." Angew. Makromol. Chem 188 (1991): 167-176.

Svec, Frantisek, and Jean MJ Fréchet. "Continuous rods of macroporous polymer as high-performance liquid chromatography separation media." Analytical Chemistry 64.7 (1992): 820-822.

Wang, Chengming, et al. "Rapid high-yield mRNA extraction for reverse-transcription PCR." Journal of biochemical and biophysical methods 70.3 (2007): 507-509.

\* cited by examiner

INDELs mAbIT1
(RNA009n Dose Response)

INDELs mTF T2
(RNA009n Dose Response)

INDELs mC3
(RNA009n Dose Response)

SEQUENCE LISTING

<160> NUMBER OF SEQ ID NOS: 17

<210> SEQ ID NO 1
<211> LENGTH: 4506
<212> TYPE: DNA
<213> ORGANISM: Artificial Sequence
<220> FEATURE:
<223> OTHER INFORMATION: Synthetic

<400> SEQUENCE: 1

```
agaggaaata agagagaaaa gaagagtaag aagaaatata agagccacca tggcccctaa      60
gaagaagaga aaagtcggaa ttcacggagt ccccgccgcc gacaaaaagt actccattgg     120
ccttgatatt ggaaccaact ccgtgggttg ggccgtgatc actgacgagt acaaggtgcc     180
gtccaagaag ttcaaggtgc tggggaacac tgaccggcac tcaattaaga gaacctgat     240 tgggcgctg ctgttcgact ccggagaaac cgcggaggct acccgcctga gcggactgc     300 ccggcggaga tacacgcgca ggaagaaccg gatttgctac ctccaagaaa tcttcagcaa     360
cgaaatggca aaggtggacg attccttctt ccatcgcctg aagagagct tcctggtgga     420 agaggacaag aagcacgaaa gacacccgat tttcggcaac atcgtggatg aggtcgcata     480
ccacgaaaag taccccacca tctatcatct tcggaagaag ctggtcgact ccaccgataa     540
ggccgatctg cgcctgatct acttggcgct ggctcacatg attaagttca gaggacactt     600
tctgatagag ggcgacctca tcccgataa ctccgacgtg gataagctgt tcatccaact     660
ggtgcagacg tacaaccaac tgtttgaaga gaatccaatc aacgccagcg ggtggacgc     720 caaggccatc ctgtccgccc ggctgtcaaa gtccagacgc ctggagaatc tcatcgcgca     780
actccctggc gaaaaaaga acggactctt cgggaatctg attgctctgt ccctggggct     840
cactccgaac ttcaagtcga acttcgacct ggcggaggac gctaagctgc agctgtccaa     900
ggacacctac gatgacgatc tggataacct tctggcccag atcggggatc aatacgccga     960
tctcttcctg gccgcaaaga acttgtcgga tgctattctg ctgagcgaca ttctgcgggt    1020
caatactgaa atcaccaagg cgcccctgtc ggccagcatg atcaagcgct acgacgaaca    1080 ccaccagac ctgactctgc tgaaggccct cgtgcgccag cagctgcctg aaaagtacaa    1140
ggagattttc ttcgaccagt ccaagaacgg atacgccgga tacattgacg gaggggccag    1200
```

```
ccaggaggaa ttttacaaat tcatcaagcc cattctcgag aaaatggacg gaaccgaaga   1260
gttgctcgtg aagctgaaca gagaggatct cctccggaag cagcggacct tcgacaacgg   1320
ttccatcccg caccaaatcc acctgggcga attgcacgcc atcctccggc ggcaggaaga   1380
tttctaccca ttcttgaagg acaatcgcga aaagatcgaa aagatcttga ctttccgcat   1440
cccgtactac gtgggccctc tggcccgcgg caactcccgc ttcgcttgga tgacacggaa   1500
gtccgaggaa accattacgc cctggaactt cgaggaagtg gtggacaagg gggcgtccgc   1560
ccagagcttc atcgaacgca tgaccaattt cgacaagaac ctcccgaacg aaaaagtgct   1620
gccaaagcac tcgctcctct acgaatactt caccgtgtac aacgagctga ctaaggtcaa   1680
atacgtgact gagggaatgc ggaagccggc cttcctgtcg ggagagcaga agaaggccat   1740
agtggacttg cttttcaaga ctaaccggaa ggtcactgtg aagcaactca aggaggacta   1800
cttcaagaag atcgagtgtt tcgactcggt ggagatctcg ggtgtcgagg accgcttcaa   1860
cgcctccctg gaacttaccc acgatctgct gaagatcatc aaggacaagg acttcctcga   1920
taacgaagaa aatgaggaca tcctcgagga tatcgtgctg accctgacct tgttcgagga   1980
tagggagatg atcgaggagc ggctcaagac ctacgcccac ctgtttgacg acaaagtgat   2040
gaagcaactg aaacggcgga ggtataccgg ctggggtcgg ctgtcccgca agctgatcaa   2100
cgggatcagg gacaagcagt ccggaaagac catcctcgac ttccttaagt ccgacggatt   2160
cgcgaaccgc aacttcatgc aacttatcca cgacgactcg ctgacattca aggaagatat   2220
ccagaaggcc caggtgtccg acagggggga ctcgcttcat gagcacatcg ctaacctggc   2280
cggatccccc gccataaaaa agggcattct gcagaccgtc aaagtggtgg atgagctggt   2340
caaggtcatg ggccggcata agccggaaaa catcgtcatc gagatggccc gcagaaacca   2400
gactacgcag aagggccaga agaactcccg ggagcggatg aagcggattg aagagggcat   2460
caaggagctc ggcagccaga ttctgaagga acatcccgtg aaaacaccc agctgcaaaa   2520 cgaaaagctc tatttgtact atctgcaaaa cggacgcgat atgtacgtgg atcaggagct   2580
ggacattaac agactgagcg actatgacgt ggatcacatt gtgcctcaaa gcttcctcaa   2640
ggacgactca attgacaaca aggtcctgac cagaagcgac aagaacagag aaagtcgga   2700 taatgtgccg tccgaagaag tggtcaagaa gatgaagaat tactggagac agctcctgaa   2760
tgcgaagctc attcccagcg gaagttcga taacctgacc aaggccgaaa ggggtggact   2820
gtccgaactc gacaaagctg gcttcatcaa gcgccaactg gtcgaaacca ggcagatcac   2880
caagcacgtc gcccagattc tggacagccg catgaacact aagtacgacg agaacgataa   2940
gctgatccgc gaagtgaagg tcatcaccct gaagtccaag ctcgtgtccg actttcggaa   3000
ggatttccag ttttacaagg tccgcgagat caacaactac catcacgccc acgacgcgta   3060
ccttaacgca gtcgtgggaa cggctcttat caagaagtac ccaaagctgg agtcggaatt   3120
tgtgtacgga gactacaaag tgtacgacgt gcgcaagatg atcgccaaat ctgagcaaga   3180
gatcgggaag gcaaccgcca atacttcttc tactcaaac attatgaatt ttttcaaaac   3240
tgagattacc ctggctaacg gagaaattcg gaagcgcccc ctgattgaaa ccaacggaga   3300
aactggagaa attgtgtggg acaagggacg ggacttcgcc accgtccgca aggtcctctc   3360
aatgccccaa gtcaacatcg tgaaaaagac cgaagtgcaa accggcggct ctcaaaggga   3420
gtccatcctg cctaagcgca acagcgacaa gctgattgcc aggaagaagg actgggaccc   3480
gaagaagtac ggaggatttg attcccctac cgtggcctac tccgtgctcg tggtggccaa   3540
```

```
agtggaaaag gggaaatcca agaagctgaa gtcggtgaag gagcttttgg gtatcaccat    3600
catgaacgc tcctcgttcg aaaagaaccc aatcgatttc ctggaagcta agggttataa    3660
ggaagtgaaa aaggacctga ttatcaagct gcccaagtac tcactgttcg agctggaaaa    3720
cggtcggaaa aggatgctgg ccagcgccgg agaactccag aagggaaacg aactggcact    3780
gccgtccaaa tacgtcaact tcctctacct tgcatcccat tacgaaaaac tcaagggatc    3840
gccggaggac aacgagcaga agcagctttt cgtggagcaa cacaagcatt acttggacga    3900
gatcatcgag cagatttccg agttctcaaa gcgcgtgatc ctggccgacg caaatctgga    3960
caaggtcctg tccgcgtaca ataagcatcg ggacaagcct atccgcgaac aggccgagaa    4020
catcatccat ctgttcactc tgacaaacct gggcgcaccc gccgcgttca agtactttga    4080
caccaccatc gataggaagc gatacacctc aactaaggaa gtgttggacg cgacccttat    4140
ccatcagtcg atcaccgggc tgtacgaaac acggatcgac ctcagccagt tgggaggcga    4200
caagcgccct gcggctacca agaaggccgg acaggccaag aagaagaaat gagcggccgc    4260
ttaattaagc tgccttctgc ggggcttgcc ttctggccat gcccttcttc tctcccttgc    4320
acctgtacct cttggtcttt gaataaagcc tgagtaggaa gtctagaaaa aaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaa                                                                4506

<210> SEQ ID NO 2
<211> LENGTH: 4506
<212> TYPE: RNA
<213> ORGANISM: Artificial Sequence
<220> FEATURE:
<223> OTHER INFORMATION: Synthetic

<400> SEQUENCE: 2
agaggaaaua agagagaaaa gaagaguaag aagaaauaua agagccacca uggcccuaa     60
gaagaagaga aaagucggaa uucacggagu ccccgccgcc gacaaaaagu acuccauugg    120
ccuugauauu ggaaccaacu ccgugggguug ggccgugauc acugacgagu acaaggugcc    180
guccaagaag uucaaggugc uggggaacac ugaccggcac ucaauuaaga gaaccugau    240
uggggcgcug cuguucgacu ccggagaaac cgcggaggcu acccgccuga gcgacugc    300
ccggcggaga uacacgcgca ggaagaaccg gauuugcuac cuccaagaaa ucuucagcaa    360
cgaaauggca aaggugggacg auuccuucuu ccaucgccug aagagagcu uccuggugga    420
agaggacaag aagcacgaaa gacacccgau uuucggcaac aucguggaug aggucgcaua    480
ccacgaaaag uacccaccca ucuaucaucu ucggaagaag cuggucgacu ccaccgauaa    540
ggccgaucug cgccugaucu acuuggcgcu ggcucacaug auuaaguuca gaggacacuu    600
ucugauagag ggcgaccuca aucccgauaa cuccgacgug gauaagcugu caccaacu    660
ggugcagacg uacaaccaac uguuugaaga gaauccaauc aacgccagcg ggguggacgc    720
caaggccauc cuguccgccc ggcugucaaa guccagacgc cuggagaauc ucaucgcgca    780
acucccuggc gaaaaaaga acggacucuu cgggaaucug auugcucugu cccggggcu    840
cacuccgaac uucaagucga acuucgaccu ggcggaggac gcuaagcugc agcuguccaa    900
ggacaccuac gaugacgauc uggauaaccu ucuggcccag aucggggauc aauacgccga    960
ucucuuccug gccgcaaaga aacuugucgga ugcuauucug cugagcgaca uucugcgggu    1020
caauacugaa aucaccaagg cgccccuguc ggccagcaug aucaagcgcu acgacgaaca    1080
```

-continued

| | |
|---|---|
| ccaccaagac cugacucugc ugaaggcccu cgugcgccag cagcugccug aaaaguacaa | 1140 |
| ggagauuuuc uucgaccagu ccaagaacgg auacgccgga uacauugacg aggggccag | 1200 |
| ccaggaggaa uuuuacaaau ucaucaagcc cauucucgag aaaauggacg gaaccgaaga | 1260 |
| guugcucgug aagcugaaca gagaggaucu ccuccggaag cagcggaccu ucgacaacgg | 1320 |
| uuccaucccg caccaaaucc accugggcga auugcacgcc auccuccggc ggcaggaaga | 1380 |
| uuucuaccca uucuugaagg caaucgcga aaagaucgaa aagaucuuga cuuuccgcau | 1440 |
| cccguacuac gugggcccuc uggcccgcgg caacucccgc uucgcuugga ugacacggaa | 1500 |
| guccgaggaa accauuacgc ccuggaacuu cgaggaagug guggacaagg gggcguccgc | 1560 |
| ccagagcuuc aucgaacgca ugaccaauuu cgacaagaac cucccgaacg aaaagugcu | 1620 |
| gccaaagcac ucgcuccucu acgaauacuu caccguguac aacgagcuga cuaaggucaa | 1680 |
| auacgugacu gagggaaugc ggaagccggc cuuccugucg ggagagcaga agaaggccau | 1740 |
| aguggacuug cuuuucaaga cuaaccggaa ggucacugug aagcaacuca aggaggacua | 1800 |
| cuucaagaag aucgagguguu cgacucgguu ggagaucucg ggugucgagg accgcuucaa | 1860 |
| cgccucccug ggaacuuacc acgaucgcu gaagaucauc aaggacaagg acuuccucga | 1920 |
| uaacgaagaa aaugaggaca uccucgagga uaucgugcug acccugaccu uguucgagga | 1980 |
| uaggagaugu aucgaggagc ggcucaagac cuacgcccac cuguuugacg acaaagugau | 2040 |
| gaagcaacug aaacggcgga gguauaccgg cuggggucgg cugucccgca agcugaucaa | 2100 |
| cgggaucagg gacaagcagu ccggaaagac cauccucgac uuccuuaagu ccgacggauu | 2160 |
| cgcgaaccgc aacuucaugc aacuuauca cgacgacucg cugacauuca aggaagauau | 2220 |
| ccagaaggcc caggugccg gacaggggga cucgcuucau gagcacaucg cuaaccuggc | 2280 |
| cggauccccc gccauaaaaa agggcauucu gcagaccguc aaagugugg augagcuggu | 2340 |
| caaggucaug ggccggcaua agccggaaaa caucgucauc gagaugccc gcagaaacca | 2400 |
| gacuacgcag aagggccaga gaacucccg ggagcggaug aagcggauug aagagggcau | 2460 |
| caaggagcuc ggcagccaga uucugaagga acauccgug gaaaacaccc agcugcaaaa | 2520 |
| cgaaaagcuc uauuuguacu aucugcaaaa cggacgcgau auguacgugg ucaggagcu | 2580 |
| ggacauuaac agacugagcg acuaugacgu ggaucacauu gugccucaaa gcuuccucaa | 2640 |
| ggacgacuca auugacaaca aggucgcugac cagaagcgac aagaacagag gaaagucgga | 2700 |
| uaaugugccg uccgaagaag uggucaagaa gaugaagaau uacuggagac agcuccugaa | 2760 |
| ugcgaagcuc auuacccagc ggaaguucga uaaccugacc aaggccgaaa ggggugacu | 2820 |
| guccgaacuc gacaaagcug gcuucaucaa gcgccaacug gucgaaacca ggcagaucac | 2880 |
| caagcacguc gcccagauuc uggacagccg cauggacacu aaguacgacg agaacgauaa | 2940 |
| gcugauccgc gaagugaagg ucaucacccu gaaguccaag cucgugcccg acuuucggaa | 3000 |
| ggauuuccag uuuuacaagg uccgcgagau caacaacuac caucacgccc acgacgcgua | 3060 |
| ccuuaacgca gucguggga cggcucuuau caagaaguac ccaaagcugg agucggaauu | 3120 |
| uguguacgga gacuacaaag ugucacgcgu gcgcaagaug aucgccaaau cugagcaaga | 3180 |
| gaucggggaag gcaaccgcca aauacuucuu cuacucaaac auuaugaauu uuucaaaac | 3240 |
| ugagauuacc cuggcuaacg gagaaauucg gaagcgcccc cugauugaaa ccaacggaga | 3300 |
| aacuggagaa auugugggg acaagggacg ggacuucgcc accguccgca aggccucuc | 3360 |
| aaugcccaa gucaacaucg ugaaaagac cgaagugcaa accggcggcu ucucaaagga | 3420 |

-continued

| | |
|---|---|
| guccauccug ccuaagcgca acagcgacaa gcugauugcc aggaagaagg acugggaccc | 3480 |
| gaagaaguac ggaggauuug auuccccuac cguggccuac uccgugcucg uggugggccaa | 3540 |
| aguggaaaag gggaaauucca agaagcugaa gucggugaag gagcuuuugg guauaccau | 3600 |
| cauggaacgc uccucguucg aaaagaaccc aaucgauuuc cuggaagcua aggguuauaa | 3660 |
| ggaagugaaa aaggaccuga uuaucaagcu gcccaaguac ucacuguucg agcuggaaaa | 3720 |
| cggucggaaa aggaugcugg ccagcgccgg agaauccag aagggaaacg aacuggcacu | 3780 |
| gccguccaaa uacgucaacu uccucuaccu ugcaucccau uacgaaaaac ucaagggauc | 3840 |
| gccggaggac aacgagcaga agcagcuuuu cguggagcaa cacaagcauu acuuggacga | 3900 |
| gaucaucgag cagauuuccg aguucucaaa gcgcgugauc cuggccgacg caaaucugga | 3960 |
| caagguccug uccgcguaca auaagcaucg ggacaagccu auccgcgaac aggccgagaa | 4020 |
| caucauccau cuguucacuc ugacaaaccu gggcgcaccc gccgcguuca aguacuuuga | 4080 |
| caccaccauc gauaggaagc gauaccacuc aacuaaggaa guguuggacg cgacccuuau | 4140 |
| ccaucagucg auccaccggc uguacgaaac acggaucgac cucagccagu ugggaggcga | 4200 |
| caagcgcccu gcggcuacca agaaggccgg acaggccaag aagaagaaau gagcggccgc | 4260 |
| uuaauuaagc ugccuucugc ggggcuugcc uucggccauu gccuucuuc ucucccuugc | 4320 |
| accuguaccu cuuggucuuu gaauaaagcc ugaguaggaa gucuagaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaa | 4506 |

<210> SEQ ID NO 3
<211> LENGTH: 4203
<212> TYPE: DNA
<213> ORGANISM: Artificial Sequence
<220> FEATURE:
<223> OTHER INFORMATION: Synthetic

<400> SEQUENCE: 3

| | |
|---|---|
| atggcccta agaagaagag aaagtcgga attcacggag tccccgccgc cgacaaaaag | 60 |
| tactccattg gccttgatat tggaaccaac tccgtgggtt gggccgtgat cactgacgag | 120 |
| tacaaggtgc cgtccaagaa gttcaaggtg ctggggaaca ctgaccggca ctcaattaag | 180 |
| aagaacctga ttggggcgct gctgttcgac tccggagaaa ccgcggaggc tacccgcctg | 240 |
| aagcggactg cccggcggag atacacgcgc aggaagaacc ggatttgcta cctccaagaa | 300 |
| atcttcagca acgaaatggc aaaggtggac gattccttct tccatcgcct ggaagagagc | 360 |
| ttcctggtgg aagaggacaa gaagcacgaa agacacccga ttttcggcaa catcgtggat | 420 |
| gaggtcgcat accacgaaaa gtaccccacc atctatcatc ttcggaagaa gctggtcgac | 480 |
| tccaccgata aggccgatct gcgcctgatc tacttggcgc tggctcacat gattaagttc | 540 |
| agaggacact ttctgataga gggcgacctc aatcccgata actccgacgt ggataagctg | 600 |
| ttcatccaac tggtgcagac gtacaaccaa ctgtttgaag agaatccaat caacgccagc | 660 |
| ggggtggacg ccaaggccat cctgtccgcc ggctgtcaa agtccagacg cctggagaat | 720 |
| ctcatcgcgc aactccctgg cgaaaaaaag aacggactct cgggaatct gattgctctg | 780 |
| tccctgggc tcactccgaa cttcaagtcg aacttcgacc tggcggagga cgctaagctg | 840 |
| cagctgtcca aggacaccta cgatgacgat ctggataacc ttctggccca gatcgggat | 900 |
| caatacgccg atctcttcct ggccgcaaag aacttgtcgg atgctattct gctgagcgac | 960 |

```
attctgcggg tcaatactga aatcaccaag gcgccctgt cggccagcat gatcaagcgc   1020
tacgacgaac accaccaaga cctgactctg ctgaaggccc tcgtgcgcca gcagctgcct   1080
gaaaagtaca aggagatttt cttcgaccag tccaagaacg gatacgccgg atacattgac   1140 ggagggggcca gccaggagga attttacaaa ttcatcaagc ccattctcga aaaatggac   1200 ggaaccgaag agttgctcgt gaagctgaac agagaggatc tcctccggaa gcagcggacc   1260
ttcgacaacg gttccatccc gcaccaaatc cacctgggcg aattgcacgc catcctccgg   1320
cggcaggaag atttctaccc attcttgaag gacaatcgcg aaaagatcga aagatcttg   1380 actttccgca tcccgtacta cgtgggccct ctggcccgcg gcaactcccg cttcgcttgg   1440
atgacacgga agtccgagga accattacg ccctggaact tcgaggaagt ggtggacaag   1500
ggggcgtccg cccagagctt catcgaacgc atgaccaatt cgacaagaa cctcccgaac   1560 gaaaagtgc tgccaaagca ctcgctcctc tacgaatact tcaccgtgta caacgagctg   1620
actaaggtca aatacgtgac tgagggaatg cggaagccgg ccttcctgtc gggagagcag   1680
aagaaggcca tagtggactt gcttttcaag actaaccgga aggtcactgt gaagcaactc   1740
aaggaggact acttcaagaa gatcgagtgt ttcgactcgg tggagatctc gggtgtcgag   1800
gaccgcttca acgcctccct gggaacttac cacgatctgc tgaagatcat caaggacaag   1860
gacttcctcg ataacgaaga aaatgaggac atcctgagg atatcgtgct gaccctgacc   1920
ttgttcgagg atagggagat gatcgaggag cggctcaaga cctacgccca cctgtttgac   1980
gacaaagtga tgaagcaact gaacggcgg aggtataccg gctggggtcg gctgtcccgc   2040
aagctgatca acgggatcag ggacaagcag tccggaaaga ccatcctcga cttccttaag   2100
tccgacggat tcgcgaaccg caacttcatg caacttatcc acgacgactc gctgacattc   2160
aaggaagata tccagaaggc ccaggtgtcc ggacaggggg actcgcttca tgagcacatc   2220
gctaacctgg ccggatcccc cgccataaaa aagggcattc tgcagaccgt caaagtggtg   2280
gatgagctgg tcaaggtcat gggccggcat aagccggaaa acatcgtcat cgagatggcc   2340
cgcgagaacc agactacgca gaagggccag aagaactccc gggagcggat gaagcggatt   2400
gaagagggca tcaaggagct cggcagccag attctgaagg aacatcccgt ggaaaacacc   2460
cagctgcaaa acgaaaagct ctatttgtac tatctgcaaa acggacgcga tatgtacgtg   2520
gatcaggagc tggacattaa cagactgagc gactatgacg tggatcacat tgtgcctcaa   2580
agcttcctca aggacgactc aattgacaac aaggtcctga ccagaagcga caagaacaga   2640
ggaaagtcgg ataatgtgcc gtccgaagaa gtggtcaaga gatgaagaa ttactggaga   2700 cagctcctga atgcgaagct cattacccag cggaagttcg ataacctgac caaggccgaa   2760
aggggtggac tgtccgaact cgacaaagct ggcttcatca agcgccaact ggtcgaaacc   2820
aggcagatca ccaagcacgt cgcccagatt ctggacagcc gcatgaacac taagtacgac   2880
gagaacgata gctgatccg cgaagtgaag gtcatcaccc tgaagtccaa gctcgtgtcc   2940
gactttcgga aggatttcca gttttacaag gtccgcgaga tcaacaacta ccatcacgcc   3000
cacgacgcgt accttaacgc agtcgtggga acggctctta tcaagaagta cccaaagctg   3060
gagtcggaat ttgtgtacgg agactacaaa gtgtacgacg tgcgcaagat gatcgccaaa   3120
tctgagcaag agatcgggaa ggcaaccgcc aaatacttct tctactcaaa cattatgaat   3180 ttttttcaaaaa ctgagattac cctggctaac ggagaaattc ggaagcgccc cctgattgaa   3240
accaacggag aaactggaga aattgtgtgg gacaagggac gggacttcgc caccgtccgc   3300
```

```
aaggtcctct caatgcccca agtcaacatc gtgaaaaaga ccgaagtgca aaccggcggc    3360
ttctcaaagg agtccatcct gcctaagcgc aacagcgaca agctgattgc caggaagaag    3420
gactgggacc cgaagaagta cggaggattt gattccccta ccgtggccta ctccgtgctc    3480
gtggtggcca agtggaaaaa ggggaaatcc aagaagctga agtcggtgaa ggagcttttg    3540
ggtatcacca tcatggaacg ctcctcgttc gaaaagaacc caatcgattt cctggaagct    3600
aagggttata aggaagtgaa aaaggacctg attatcaagc tgcccaagta ctcactgttc    3660
gagctggaaa acggtcggaa aggatgctg gccagcgccg agaactcca aagggaaac    3720 gaactggcac tgccgtccaa atacgtcaac ttcctctacc ttgcatccca ttacgaaaaa    3780
ctcaagggat cgccggagga caacgagcag aagcagcttt cgtggagca acacaagcat    3840 tacttggacg agatcatcga gcagatttcc gagttctcaa agcgcgtgat cctggccgac    3900
gcaaatctgg acaaggtcct gtccgcgtac aataagcatc gggacaagcc tatccgcgaa    3960
caggccgaga acatcatcca tctgttcact ctgacaaacc tgggcgcacc cgccgcgttc    4020
aagtactttg acaccaccat cgataggaag cgatacacct caactaagga agtgttggac    4080 gcgacccta tccatcagtc gatcaccggg ctgtacgaaa cacggatcga cctcagccag    4140
ttgggaggcg acagcgccc tgcggctacc aagaaggccg acaggccaa gaagaagaaa    4200 tga                                                                 4203

<210> SEQ ID NO 4
<211> LENGTH: 4203
<212> TYPE: RNA
<213> ORGANISM: Artificial Sequence
<220> FEATURE:
<223> OTHER INFORMATION: Synthetic

<400> SEQUENCE: 4 auggcccua agaagaagag aaaagucgga auucacggag uccccgccgc cgacaaaaag      60
uacuccauug ccuugauau uggaaccaac uccguggguu gggccgugau cacugacgag     120
uacaaggugc cguccaagaa guucaaggug cuggggaaca cugaccggca cucaauuaag     180
aagaaccuga uuggggcgcu gcuguucgac uccgagaaaa ccgcggaggc uacccgccug     240
aagcggacug cccggcggag auacacgcgc aggaagaacc ggauuugcua ccuccaagaa     300
aucuucagca cgaaauggc aaagguggac gauccuucu ccaucgccu ggaagagagc      360 uuccugguug aagaggacaa gaagcacgaa agacacccga uuucggcaa caucguggau     420 gaggucgcau accacgaaaa guacccccacc aucuaucauc uucggaagaa gcuggucgac     480
uccaccgaua aggccgaucu cgccugauc uacuuggcgc uggcucacau gauuaaguuc     540
agaggacacu uucugauaga gggcgaccuc aaucccgaua acuccgacgu ggauaagcug     600
uucauccaac uggugcagac guacaaccaa cuguuugaag agaauccaau caacgccagc     660 ggggugacg ccaaggccau ccugccgcc cggcugucaa aguccagacg ccuggagaau     720
cucaucgcgc aacucccugg cgaaaaaag aacggacucu cgggaaucu gauugcucug     780 ucccugggc ucacuccgaa cuucaagucg aacuucgacc uggcggagga cgcuaagcug     840
cagcugucca aggacaccua cgaugacgau cuggauaacc uucuggccca gaucggggau     900
caauacgccg aucuuuccu ggccgcaaag aacuugucgg augcuauucu gcugagcgac     960
auucugcggg ucaauacuga aaucaccaag gcgccccgu cggccagcau gaucaagcgc    1020
uacgacgaac accaccaaga ccugacucug cugaggcccc ucgugcgcca gcagcugccu    1080
gaaaaguaca aggagauuuu cuucgaccag uccaagaacg gauacgccgg auacauugac    1140
```

```
ggaggggcca gccaggagga auuuuacaaa uucaucaagc ccauucucga gaaaauggac    1200
ggaaccgaag aguugcucgu gaagcugaac agagaggauc uccuccggaa gcagcggacc    1260
uucgacaacg guuccauccc gcaccaaauc caccugggcg aauugcacgc cauccuccgg    1320
cggcaggaag auuucuaccc auucuugaag gacaaucgcg aaaagaucga aaagaucuug    1380
acuuuccgca ucccguacua cgugggcccu cuggcccgcg caacucccg cuucgcuugg     1440 augacacgga aguccgagga aaccauuacg cccuggaacu ucgaggaagu gguggacaag    1500
ggggcguccg cccagagcuu caucgaacgc augaccaauu ucgacaagaa ccucccgaac    1560
gaaaaagugc ugccaaagca cucgcuccuc uacgaauacu ucaccgugua caacgagcug    1620
acuaagguca aauacgugac ugagggaaug cggaagccgg ccuuccuguc gggagagcag    1680
aagaaggcca uaguggacuu gcuuuucaag acuaaccgga aggucacugu gaagcaacuc    1740
aaggaggacu acuucaagaa gaucgagugu uucgacucgg uggagaucuc ggguguggag    1800
gaccgcuuca acgccucccu gggaacuuac cacgaucugc ugaagaucau caaggacaag    1860
gacuuccucg auaacgaaga aaaugaggac auccucgagg auaucgugcu gacccugacc    1920
uuguucgagg auagggagau gaucgaggag cggcucaaga ccuacgccca ccuguuugac    1980
gacaaaguga ugaagcaacu gaaacggcgg agguauaccg gcugggucg gcugucccgc     2040 aagcugauca acgggaucag ggacaagcag uccggaaaga ccauccucga cuuccuuaag    2100
uccgacggau ucgcgaaccg caacuucaug caacuuaucc acgacgacuc gcugacauuc    2160
aaggaagaua uccagaaggc ccaggugucc ggacagggg acucgcuuca ugagcacauc      2220
gcuaaccugg ccggauccc cgccauaaaa aagggcauuc ugcagaccgu caagugggug     2280
gaugagcugg ucaaggucau gggccggcau aagccggaaa acaucgucau cgagaugcc     2340 cgcgagaacc agacuacgca aagggccag aagaacccc gggagcggau gaagcggauu       2400
gaagagggca ucaaggagcu cggcagccag auucugaagg aacaucccgu ggaaaacacc    2460
cagcugcaaa acgaaaagcu cuauuuguac uaucugcaaa acggacgcga uauguacgug    2520
gaucaggagc uggacauuaa cagacugagc gacuaugacg uggaucacau gugccucaa     2580 agcuuccuca aggacgacuc aauugacaac aagguccuga ccagaagcga caagaacaga    2640
ggaaagucgg auaaugugcc guccgaagaa guguucaaga agaugaagaa uuacuggaga    2700
cagcuccuga augcgaagcu cauuacccag cggaaguucg auaaccugac caaggccgaa    2760 aggggguggac uguccgaacu cgacaaagcu ggcuucauca agcgccaacu ggucgaaacc    2820
aggcagauca ccaagcacgu cgcccagauu cuggacagcc gcaugaacac uaaguacgac    2880
gagaacgaua agcugaucgc cgaagugaag gucaucaccc ugaaguccaa gcucgugucc    2940
gacuuucgga aggauuucca guuuuacaag guccgcgaga ucaacaacua ccaucacgcc    3000
cacgacgcgu accuuaacgc agucguggga acggcucuua ucaagaagua cccaaagcug    3060
gagucggaau uuguguacgg agacuacaaa guguacgacg ugcgcaagau gaucgccaaa    3120
ucugagcaag agaucgggaa ggcaaccgcc aaauacuucu cuacucaaa cauuaugaau     3180 uuuuucaaaa cugagauuac ccuggcuaac ggagaaauuc ggaagcgccc ccugauugaa    3240 accaacgag aaacuggaga aauugugugg acaaggac gggacuucgc caccgucgc         3300 aaggucucu caaugcccca agucaacauc gugaaaaga ccgaagugca aaccggcggc       3360
uucucaaagg aguccauccu gccuaagcgc aacagcgaca agcugauugc caggaagaag    3420
gacugggacc cgaagaagua cggaggauuu gauucccua ccgugggccua cucccgugcuc    3480
```

| | |
|---|---|
| gugguggcca aagugggaaaa ggggaaaucc aagaagcuga agucggugaa ggagcuuuug | 3540 |
| gguaucacca ucauggaacg cuccucguuc gaaaagaacc caaucgauuu ccuggaagcu | 3600 |
| aagggguuaua aggaagugaa aaaggaccug auuaucaagc ugcccaagua cucacuguuc | 3660 |
| gagcuggaaa acggucggaa aaggaugcug gccagcgccg gagaacucca gaagggaaac | 3720 |
| gaacuggcac ugccguccaa auacgucaac uuccucuacc uugcauccca uuacgaaaaa | 3780 |
| cucaagggau cgccggagga caacgagcag aagcagcuuu cguggagca acacaagcau | 3840 |
| uacuuggacg agaucaucga gcagauuucc gaguucucaa agcgcgugau ccuggccgac | 3900 |
| gcaaaucugg acaagguccu guccgcguac aauaagcauc gggacaagcc uauccgcgaa | 3960 |
| caggccgaga acaucaucca ucuguucacu cugacaaacc ugggcgcacc cgccgcguuc | 4020 |
| aaguacuuug acaccaccau cgauaggaag cgauacaccu caacuaagga aguguuggac | 4080 |
| gcgacccuua uccaucaguc gaucaccggg cuguacgaaa cacggaucga ccucagccag | 4140 |
| uugggaggcg acaagcgccc ugcggcuacc aagaaggccg acaggccaa gaagaagaaa | 4200 |
| uga | 4203 |

<210> SEQ ID NO 5
<211> LENGTH: 1400
<212> TYPE: PRT
<213> ORGANISM: Artificial Sequence
<220> FEATURE:
<223> OTHER INFORMATION: Synthetic

<400> SEQUENCE: 5

```
Met Ala Pro Lys Lys Arg Lys Val Gly Ile His Gly Val Pro Ala
1               5                   10                  15

Ala Asp Lys Lys Tyr Ser Ile Gly Leu Asp Ile Gly Thr Asn Ser Val
                20                  25                  30

Gly Trp Ala Val Ile Thr Asp Glu Tyr Lys Val Pro Ser Lys Lys Phe
            35                  40                  45

Lys Val Leu Gly Asn Thr Asp Arg His Ser Ile Lys Lys Asn Leu Ile
        50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
```

-continued

```
            225                 230                 235                 240
Leu Ile Ala Gln Leu Pro Gly Glu Lys Lys Asn Gly Leu Phe Gly Asn
                245                 250                 255
Leu Ile Ala Leu Ser Leu Gly Leu Thr Pro Asn Phe Lys Ser Asn Phe
            260                 265                 270
Asp Leu Ala Glu Asp Ala Lys Leu Gln Leu Ser Lys Asp Thr Tyr Asp
            275                 280                 285
Asp Asp Leu Asp Asn Leu Leu Ala Gln Ile Gly Asp Gln Tyr Ala Asp
            290                 295                 300
Leu Phe Leu Ala Ala Lys Asn Leu Ser Asp Ala Ile Leu Leu Ser Asp
305                 310                 315                 320
Ile Leu Arg Val Asn Thr Glu Ile Thr Lys Ala Pro Leu Ser Ala Ser
                325                 330                 335
Met Ile Lys Arg Tyr Asp Glu His His Gln Asp Leu Thr Leu Leu Lys
                340                 345                 350
Ala Leu Val Arg Gln Gln Leu Pro Glu Lys Tyr Lys Glu Ile Phe Phe
            355                 360                 365
Asp Gln Ser Lys Asn Gly Tyr Ala Gly Tyr Ile Asp Gly Gly Ala Ser
            370                 375                 380
Gln Glu Glu Phe Tyr Lys Phe Ile Lys Pro Ile Leu Glu Lys Met Asp
385                 390                 395                 400
Gly Thr Glu Glu Leu Leu Val Lys Leu Asn Arg Glu Asp Leu Leu Arg
                405                 410                 415
Lys Gln Arg Thr Phe Asp Asn Gly Ser Ile Pro His Gln Ile His Leu
            420                 425                 430
Gly Glu Leu His Ala Ile Leu Arg Arg Gln Glu Asp Phe Tyr Pro Phe
            435                 440                 445
Leu Lys Asp Asn Arg Glu Lys Ile Glu Lys Ile Leu Thr Phe Arg Ile
            450                 455                 460
Pro Tyr Tyr Val Gly Pro Leu Ala Arg Gly Asn Ser Arg Phe Ala Trp
465                 470                 475                 480
Met Thr Arg Lys Ser Glu Glu Thr Ile Thr Pro Trp Asn Phe Glu Glu
                485                 490                 495
Val Val Asp Lys Gly Ala Ser Ala Gln Ser Phe Ile Glu Arg Met Thr
            500                 505                 510
Asn Phe Asp Lys Asn Leu Pro Asn Glu Lys Val Leu Pro Lys His Ser
            515                 520                 525
Leu Leu Tyr Glu Tyr Phe Thr Val Tyr Asn Glu Leu Thr Lys Val Lys
            530                 535                 540
Tyr Val Thr Glu Gly Met Arg Lys Pro Ala Phe Leu Ser Gly Glu Gln
545                 550                 555                 560
Lys Lys Ala Ile Val Asp Leu Leu Phe Lys Thr Asn Arg Lys Val Thr
                565                 570                 575
Val Lys Gln Leu Lys Glu Asp Tyr Phe Lys Lys Ile Glu Cys Phe Asp
            580                 585                 590
Ser Val Glu Ile Ser Gly Val Glu Asp Arg Phe Asn Ala Ser Leu Gly
            595                 600                 605
Thr Tyr His Asp Leu Leu Lys Ile Ile Lys Asp Lys Asp Phe Leu Asp
            610                 615                 620
Asn Glu Glu Asn Glu Asp Ile Leu Glu Asp Ile Val Leu Thr Leu Thr
625                 630                 635                 640
Leu Phe Glu Asp Arg Glu Met Ile Glu Glu Arg Leu Lys Thr Tyr Ala
                645                 650                 655
```

```
His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
            675                 680             685

Lys Gln Ser Gly Lys Thr Ile Leu Asp Phe Leu Lys Ser Asp Gly Phe
        690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
            755                 760                 765

Arg His Lys Pro Glu Asn Ile Val Ile Glu Met Ala Arg Glu Asn Gln
            770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
            835                 840                 845

Leu Ser Asp Tyr Asp Val Asp His Ile Val Pro Gln Ser Phe Leu Lys
            850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
            915                 920                 925

Lys Ala Gly Phe Ile Lys Arg Gln Leu Val Glu Thr Arg Gln Ile Thr
930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala His Asp Ala Tyr Leu Asn Ala Val
            995                 1000                1005

Val Gly Thr Ala Leu Ile Lys Lys Tyr Pro Lys Leu Glu Ser Glu
            1010                1015                1020

Phe Val Tyr Gly Asp Tyr Lys Val Tyr Asp Val Arg Lys Met Ile
            1025                1030                1035

Ala Lys Ser Glu Gln Glu Ile Gly Lys Ala Thr Ala Lys Tyr Phe
            1040                1045                1050

Phe Tyr Ser Asn Ile Met Asn Phe Phe Lys Thr Glu Ile Thr Leu
            1055                1060                1065
```

Ala Asn Gly Glu Ile Arg Lys Arg Pro Leu Ile Glu Thr Asn Gly
1070                1075                1080

Glu Thr Gly Glu Ile Val Trp Asp Lys Gly Arg Asp Phe Ala Thr
1085                1090                1095

Val Arg Lys Val Leu Ser Met Pro Gln Val Asn Ile Val Lys Lys
1100                1105                1110

Thr Glu Val Gln Thr Gly Gly Phe Ser Lys Glu Ser Ile Leu Pro
1115                1120                1125

Lys Arg Asn Ser Asp Lys Leu Ile Ala Arg Lys Lys Asp Trp Asp
1130                1135                1140

Pro Lys Lys Tyr Gly Gly Phe Asp Ser Pro Thr Val Ala Tyr Ser
1145                1150                1155

Val Leu Val Val Ala Lys Val Glu Lys Gly Lys Ser Lys Lys Leu
1160                1165                1170

Lys Ser Val Lys Glu Leu Leu Gly Ile Thr Ile Met Glu Arg Ser
1175                1180                1185

Ser Phe Glu Lys Asn Pro Ile Asp Phe Leu Glu Ala Lys Gly Tyr
1190                1195                1200

Lys Glu Val Lys Lys Asp Leu Ile Ile Lys Leu Pro Lys Tyr Ser
1205                1210                1215

Leu Phe Glu Leu Glu Asn Gly Arg Lys Arg Met Leu Ala Ser Ala
1220                1225                1230

Gly Glu Leu Gln Lys Gly Asn Glu Leu Ala Leu Pro Ser Lys Tyr
1235                1240                1245

Val Asn Phe Leu Tyr Leu Ala Ser His Tyr Glu Lys Leu Lys Gly
1250                1255                1260

Ser Pro Glu Asp Asn Glu Gln Lys Gln Leu Phe Val Glu Gln His
1265                1270                1275

Lys His Tyr Leu Asp Glu Ile Ile Glu Gln Ile Ser Glu Phe Ser
1280                1285                1290

Lys Arg Val Ile Leu Ala Asp Ala Asn Leu Asp Lys Val Leu Ser
1295                1300                1305

Ala Tyr Asn Lys His Arg Asp Lys Pro Ile Arg Glu Gln Ala Glu
1310                1315                1320

Asn Ile Ile His Leu Phe Thr Leu Thr Asn Leu Gly Ala Pro Ala
1325                1330                1335

Ala Phe Lys Tyr Phe Asp Thr Thr Ile Asp Arg Lys Arg Tyr Thr
1340                1345                1350

Ser Thr Lys Glu Val Leu Asp Ala Thr Leu Ile His Gln Ser Ile
1355                1360                1365

Thr Gly Leu Tyr Glu Thr Arg Ile Asp Leu Ser Gln Leu Gly Gly
1370                1375                1380

Asp Lys Arg Pro Ala Ala Thr Lys Lys Ala Gly Gln Ala Lys Lys
1385                1390                1395

Lys Lys
1400

<210> SEQ ID NO 6
<211> LENGTH: 1367
<212> TYPE: PRT
<213> ORGANISM: Artificial Sequence
<220> FEATURE:
<223> OTHER INFORMATION: Synthetic

<400> SEQUENCE: 6

```
Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
```

-continued

```
            420             425             430
Lys Asp Asn Arg Glu Lys Ile Glu Lys Ile Leu Thr Phe Arg Ile Pro
            435             440             445

Tyr Tyr Val Gly Pro Leu Ala Arg Gly Asn Ser Arg Phe Ala Trp Met
            450             455             460

Thr Arg Lys Ser Glu Glu Thr Ile Thr Pro Trp Asn Phe Glu Glu Val
465             470             475             480

Val Asp Lys Gly Ala Ser Ala Gln Ser Phe Ile Glu Arg Met Thr Asn
                485             490             495

Phe Asp Lys Asn Leu Pro Asn Glu Lys Val Leu Pro Lys His Ser Leu
            500             505             510

Leu Tyr Glu Tyr Phe Thr Val Tyr Asn Glu Leu Thr Lys Val Lys Tyr
            515             520             525

Val Thr Glu Gly Met Arg Lys Pro Ala Phe Leu Ser Gly Glu Gln Lys
            530             535             540

Lys Ala Ile Val Asp Leu Leu Phe Lys Thr Asn Arg Lys Val Thr Val
545             550             555             560

Lys Gln Leu Lys Glu Asp Tyr Phe Lys Lys Ile Glu Cys Phe Asp Ser
                565             570             575

Val Glu Ile Ser Gly Val Glu Asp Arg Phe Asn Ala Ser Leu Gly Thr
                580             585             590

Tyr His Asp Leu Leu Lys Ile Ile Lys Asp Lys Asp Phe Leu Asp Asn
            595             600             605

Glu Glu Asn Glu Asp Ile Leu Glu Asp Ile Val Leu Thr Leu Thr Leu
            610             615             620

Phe Glu Asp Arg Glu Met Ile Glu Glu Arg Leu Lys Thr Tyr Ala His
625             630             635             640

Leu Phe Asp Asp Lys Val Met Lys Gln Leu Lys Arg Arg Arg Tyr Thr
                645             650             655

Gly Trp Gly Arg Leu Ser Arg Lys Leu Ile Asn Gly Ile Arg Asp Lys
                660             665             670

Gln Ser Gly Lys Thr Ile Leu Asp Phe Leu Lys Ser Asp Gly Phe Ala
            675             680             685

Asn Arg Asn Phe Met Gln Leu Ile His Asp Asp Ser Leu Thr Phe Lys
            690             695             700

Glu Asp Ile Gln Lys Ala Gln Val Ser Gly Gln Gly Asp Ser Leu His
705             710             715             720

Glu His Ile Ala Asn Leu Ala Gly Ser Pro Ala Ile Lys Lys Gly Ile
                725             730             735

Leu Gln Thr Val Lys Val Val Asp Glu Leu Val Lys Val Met Gly Arg
            740             745             750

His Lys Pro Glu Asn Ile Val Ile Glu Met Ala Arg Glu Asn Gln Thr
            755             760             765

Thr Gln Lys Gly Gln Lys Asn Ser Arg Glu Arg Met Lys Arg Ile Glu
            770             775             780

Glu Gly Ile Lys Glu Leu Gly Ser Gln Ile Leu Lys Glu His Pro Val
785             790             795             800

Glu Asn Thr Gln Leu Gln Asn Glu Lys Leu Tyr Leu Tyr Tyr Leu Gln
                805             810             815

Asn Gly Arg Asp Met Tyr Val Asp Gln Glu Leu Asp Ile Asn Arg Leu
                820             825             830

Ser Asp Tyr Asp Val Asp His Ile Val Pro Gln Ser Phe Leu Lys Asp
            835             840             845
```

-continued

Asp Ser Ile Asp Asn Lys Val Leu Thr Arg Ser Asp Lys Asn Arg Gly
    850             855             860

Lys Ser Asp Asn Val Pro Ser Glu Glu Val Val Lys Lys Met Lys Asn
865             870             875             880

Tyr Trp Arg Gln Leu Leu Asn Ala Lys Leu Ile Thr Gln Arg Lys Phe
            885             890             895

Asp Asn Leu Thr Lys Ala Glu Arg Gly Gly Leu Ser Glu Leu Asp Lys
            900             905             910

Ala Gly Phe Ile Lys Arg Gln Leu Val Glu Thr Arg Gln Ile Thr Lys
            915             920             925

His Val Ala Gln Ile Leu Asp Ser Arg Met Asn Thr Lys Tyr Asp Glu
    930             935             940

Asn Asp Lys Leu Ile Arg Glu Val Lys Val Ile Thr Leu Lys Ser Lys
945             950             955             960

Leu Val Ser Asp Phe Arg Lys Asp Phe Gln Phe Tyr Lys Val Arg Glu
            965             970             975

Ile Asn Asn Tyr His His Ala His Asp Ala Tyr Leu Asn Ala Val Val
            980             985             990

Gly Thr Ala Leu Ile Lys Lys Tyr Pro Lys Leu Glu Ser Glu Phe Val
            995             1000            1005

Tyr Gly Asp Tyr Lys Val Tyr Asp Val Arg Lys Met Ile Ala Lys
    1010            1015            1020

Ser Glu Gln Glu Ile Gly Lys Ala Thr Ala Lys Tyr Phe Phe Tyr
    1025            1030            1035

Ser Asn Ile Met Asn Phe Phe Lys Thr Glu Ile Thr Leu Ala Asn
    1040            1045            1050

Gly Glu Ile Arg Lys Arg Pro Leu Ile Glu Thr Asn Gly Glu Thr
    1055            1060            1065

Gly Glu Ile Val Trp Asp Lys Gly Arg Asp Phe Ala Thr Val Arg
    1070            1075            1080

Lys Val Leu Ser Met Pro Gln Val Asn Ile Val Lys Lys Thr Glu
    1085            1090            1095

Val Gln Thr Gly Gly Phe Ser Lys Glu Ser Ile Leu Pro Lys Arg
    1100            1105            1110

Asn Ser Asp Lys Leu Ile Ala Arg Lys Lys Asp Trp Asp Pro Lys
    1115            1120            1125

Lys Tyr Gly Gly Phe Asp Ser Pro Thr Val Ala Tyr Ser Val Leu
    1130            1135            1140

Val Val Ala Lys Val Glu Lys Gly Lys Ser Lys Lys Leu Lys Ser
    1145            1150            1155

Val Lys Glu Leu Leu Gly Ile Thr Ile Met Glu Arg Ser Ser Phe
    1160            1165            1170

Glu Lys Asn Pro Ile Asp Phe Leu Glu Ala Lys Gly Tyr Lys Glu
    1175            1180            1185

Val Lys Lys Asp Leu Ile Ile Lys Leu Pro Lys Tyr Ser Leu Phe
    1190            1195            1200

Glu Leu Glu Asn Gly Arg Lys Arg Met Leu Ala Ser Ala Gly Glu
    1205            1210            1215

Leu Gln Lys Gly Asn Glu Leu Ala Leu Pro Ser Lys Tyr Val Asn
    1220            1225            1230

Phe Leu Tyr Leu Ala Ser His Tyr Glu Lys Leu Lys Gly Ser Pro
    1235            1240            1245

```
Glu  Asp  Asn  Glu  Gln  Lys  Gln  Leu  Phe  Val  Glu  Gln  His  Lys  His
    1250                1255                     1260

Tyr  Leu  Asp  Glu  Ile  Ile  Glu  Gln  Ile  Ser  Glu  Phe  Ser  Lys  Arg
    1265                1270                     1275

Val  Ile  Leu  Ala  Asp  Ala  Asn  Leu  Asp  Lys  Val  Leu  Ser  Ala  Tyr
    1280                1285                     1290

Asn  Lys  His  Arg  Asp  Lys  Pro  Ile  Arg  Glu  Gln  Ala  Glu  Asn  Ile
    1295                1300                     1305

Ile  His  Leu  Phe  Thr  Leu  Thr  Asn  Leu  Gly  Ala  Pro  Ala  Ala  Phe
    1310                1315                     1320

Lys  Tyr  Phe  Asp  Thr  Thr  Ile  Asp  Arg  Lys  Arg  Tyr  Thr  Ser  Thr
    1325                1330                     1335

Lys  Glu  Val  Leu  Asp  Ala  Thr  Leu  Ile  His  Gln  Ser  Ile  Thr  Gly
    1340                1345                     1350

Leu  Tyr  Glu  Thr  Arg  Ile  Asp  Leu  Ser  Gln  Leu  Gly  Gly  Asp
    1355                1360                     1365

<210> SEQ ID NO 7
<211> LENGTH: 16
<212> TYPE: PRT
<213> ORGANISM: Artificial Sequence
<220> FEATURE:
<223> OTHER INFORMATION: Synthetic

<400> SEQUENCE: 7

Lys  Arg  Pro  Ala  Ala  Thr  Lys  Lys  Ala  Gly  Gln  Ala  Lys  Lys  Lys  Lys
1                 5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Pro  Lys  Lys  Lys  Arg  Lys  Val
1                 5

<210> SEQ ID NO 9
<211> LENGTH: 49
<212> TYPE: DNA
<213> ORGANISM: Artificial Sequence
<220> FEATURE:
<223> OTHER INFORMATION: Synthetic

<400> SEQUENCE: 9
agaggaaata agagagaaaa gaagagtaag aagaaatata agagccacc                49

<210> SEQ ID NO 10
<211> LENGTH: 49
<212> TYPE: RNA
<213> ORGANISM: Artificial Sequence
<220> FEATURE:
<223> OTHER INFORMATION: Synthetic

<400> SEQUENCE: 10
agaggaaaua agagagaaaa gaagaguaag aagaaauaua agagccacc                49

<210> SEQ ID NO 11
<211> LENGTH: 114
<212> TYPE: DNA
<213> ORGANISM: Artificial Sequence
```

<220> FEATURE:
<223> OTHER INFORMATION: Synthetic

<400> SEQUENCE: 11

| | | | | | |
|---|---|---|---|---|---|
| gcggccgctt | aattaagctg | ccttctgcgg | ggcttgcctt | ctggccatgc | ccttcttctc | 60
| tcccttgcac | ctgtacctct | tggtctttga | ataaagcctg | agtaggaagt | ctag | 114

<210> SEQ ID NO 12
<211> LENGTH: 114
<212> TYPE: RNA
<213> ORGANISM: Artificial Sequence
<220> FEATURE:
<223> OTHER INFORMATION: Synthetic

<400> SEQUENCE: 12

| | | | | | |
|---|---|---|---|---|---|
| gcggccgcuu | aauuaagcug | ccuucugcgg | ggcuugccuu | cuggccaugc | ccuucuucuc | 60
| ucccuugcac | cuguaccucu | uggucuuuga | auaaagccug | aguaggaagu | cuag | 114

<210> SEQ ID NO 13
<211> LENGTH: 140
<212> TYPE: RNA
<213> ORGANISM: Artificial Sequence
<220> FEATURE:
<223> OTHER INFORMATION: Synthetic

<400> SEQUENCE: 13

| | | | | | |
|---|---|---|---|---|---|
| aaaaaaaaaa | aaaaaaaaaa | aaaaaaaaaa | aaaaaaaaaa | aaaaaaaaaa | aaaaaaaaaa | 60
| aaaaaaaaaa | aaaaaaaaaa | aaaaaaaaaa | aaaaaaaaaa | aaaaaaaaaa | aaaaaaaaaa | 120
| aaaaaaaaaa | aaaaaaaaaa | | | | | 140

<210> SEQ ID NO 14
<211> LENGTH: 4504
<212> TYPE: RNA
<213> ORGANISM: Artificial Sequence
<220> FEATURE:
<223> OTHER INFORMATION: Synthetic

<400> SEQUENCE: 14

| | | | | | |
|---|---|---|---|---|---|
| aggaaauaag | agagaaaaga | agaguaagaa | gaaauauaag | agccaccaug | gccccuaaga | 60
| agaagagaaa | agucggaauu | cacggagucc | ccgccgccga | caaaaaguac | uccauuggcc | 120
| uugauauugg | aaccaacucc | gugggguuggg | ccgugaucac | ugacgaguac | aaggugccgu | 180
| ccaagaaguu | caaggugcug | gggaacacug | accggcacuc | aauuaagaag | aaccugauug | 240
| gggcgcugcu | guucgacucc | ggagaaaccg | cggaggcuac | ccgccugaag | cggacugccc | 300
| ggcggagaua | cacgcgcagg | aagaaccgga | uuugcuaccu | ccaagaaauc | uucagcaacg | 360
| aaauggcaaa | ggugacgau | uccuucuucc | aucgccugga | agagagcuuc | cugguggaag | 420
| aggacaagaa | gcacgaaaga | cacccgauuu | ucggcaacau | cguggaugag | gucgcauacc | 480
| acgaaaaguua | ccccaccauc | uaucaucuuc | ggaagaagcu | ggucgacucc | accgauaagg | 540
| ccgaucugcg | ccugaucuac | uuggcgcugg | cucacaugau | uaaguucaga | ggacacuuuc | 600
| ugauagaggg | cgaccucaau | cccgauaacu | ccgacgugga | uaagcuguuc | auccaacugg | 660
| ugcagacgua | caaccaacug | uuugaagaga | auccaaucaa | cgccagcggg | guggacgcca | 720
| aggccauccu | guccgcccgg | cugucaaagu | ccagacgccu | ggagaaucuc | aucgcgcaac | 780
| ucccuggcga | aaaaaagaac | ggacucuucg | ggaaucugau | ugcucugucc | cggggcuca | 840
| cuccgaacuu | caagucgaac | uucgaccugg | cggaggacgc | uaagcugcag | cuguccaagg | 900

```
acaccuacga ugacgaucug gauaaccuuc uggcccagau cggggaucaa uacgccgauc    960
ucuuccuggc cgcaaagaac uugucggaug cuauucugcu gagcgacauu cugcggguca   1020
auacugaaau caccaaggcg ccccugucgg ccagcaugau caagcgcuac gacgaacacc   1080
accaagaccu gacucugcug aaggcccucu gcgccagca gcugccugaa aaguacaagg    1140
agauuuucuu cgaccaguccc aagaacggau acgccggaua cauugacgga ggggccagcc  1200
aggaggaauu uuacaaauuc aucaagccca uucucgagaa aauggacgga accgaagagu   1260
ugcucgugaa gcugaacaga gaggaucucc uccggaagca gcggaccuuc gacaacgguu   1320
ccaucccgca ccaaauccac cugggcgaau gcacgccau ccuccggcgg caggaagauu    1380
ucuacccauu cuugaaggac aaucgcgaaa agaucgaaaa gaucuugacu uccgcaucc    1440
cguacuacgu gggcccucug gcccgcggca acucccgcuu cgcuuggaug acacggaagu   1500
ccgaggaaac cauuacgccc uggaacuucg aggaaguggu ggacaagggg gcguccgccc   1560
agagcuucau cgaacgcaug accauuucg acaagaaccu cccgaacgaa aagugcugc    1620
caaagcacuc gcuccucuac gaauacuuca ccguguacaa cgagcugacu aaggucaaau   1680
acgugacuga gggaaugcgg aagccggccu uccugucggg agagcagaag aaggccauag   1740
uggacuugcu uuucaagacu aaccggaagg ucacugugaa gcaacucaag gaggacuacu   1800
ucaagaagau cgaguguuuc gacucggugg agaucucggg ugucgaggac cgcuucaacg   1860
ccucccuggg aacuuaccac gaucugcuga agaucaucaa ggacaaggac uuccucgaua   1920
acgaagaaaa ugaggacauc cucgaggaua ucgugcugac ccugaccuug uucgaggaua   1980
gggagaugau cgaggagcgg cucaagaccu acgcccaccu guuugacgac aaagugauga   2040
agcaacugaa acggcggagg uauaccggcu ggggucggcu guccgcaag cugaucaacg    2100
ggaucaggga caagcagucc ggaaagacca uccucgacuu ccuuaaaguc gacggauucg   2160
cgaaccgcaa cuucaugcaa cuuauccacg acgacucgcu gacauucaag gaagauaucc   2220
agaaggccca ggugucgga cagggggacu cgcuucauga gcacaucgcu aaccuggccg    2280
gauccccgc cauaaaaaag ggcauucugc agaccgucaa aguggggau gagcuggcu      2340
aggucauggg ccggcauaag ccggaaaaca ucgucaucga aauggccgc gagaaccaga    2400
cuacgcagaa gggccagaag aacucccggg agcggaugaa gcggauugaa gagggcauca   2460
aggagcucgg cagccagauu cugaaggaac aucccgugga aaacacccag cugcaaaacg   2520
aaaagcucua uuuguacuau cugcaaaacg gacgcgauau guacguggau caggagcugg   2580
acauuaacag acugagcgac uaugacgugg aucacauugu gccucaaagc uuccucaagg   2640
acgacucaau ugacaacaag guccugacca gaagcgacaa gaacagagga agucggaua   2700
augugccguc cgaagaagug gucaagaaga ugaagaauua cggagacag cuccugaaug    2760
cgaagcucau uacccagcgg aaguucgaua accugaccaa ggccgaaagg ggugacguu    2820
ccgaacucga caaagcuggc uucaucaagc gccaacuggu cgaaaccagg cagaucacca   2880
agcacgucgc ccagauucug gacagccgca ugaacacuaa gacgacgag aacgauaagc    2940
ugauccgcga agugaagguc aucacccuga aguccaagcu cguguccgac uuucggaagg   3000
auuuccaguu uuacaaggguc cgcgagauca caacuaccaa ucacgcccac gacgcguacc  3060
uuaacgcagu cguggaacg gcucuuauca agaaguaccc aaagcuggag ucggaauuug    3120
uguacgagga cuacaagug uacgacgugc gcaagaugau cgccaaaucu gagcaagaga   3180
ucgggaaggc aaccgccaaa uacuucuucu acucaaacau uaugaauuuu ucaaaacug    3240
agauuacccu ggcuaacgga gaaauucgga agcgcccccu gauugaaacc aacggagaaa  3300
```

```
cuggagaaau uguguggggac aagggacggg acuucgccac cguccgcaag guccucucaa    3360
ugccccaagu caacaucgug aaaaagaccg aagugcaaac cggcggcuuc ucaaaggagu    3420
ccauccugcc uaagcgcaac agcgacaagc ugauugccag gaagaaggac ugggacccga    3480
agaaguacgg aggauuugau uccccuaccg uggccuacuc cgugcucgug guggccaaag    3540
uggaaaaggg gaaauccaag aagcugaagu cggugaagga gcuuugggu aucaccauca     3600 uggaacgcuc cucguucgaa aagaacccaa ucgauuuccu ggaagcuaag gguuauaagg    3660
aagugaaaaa ggaccugauu aucaagcugc caaguacuc acguucgag cuggaaaacg     3720 gucggaaaag gaugcuggcc agcgccggag aacuccagaa gggaaacgaa cuggcacugc    3780
cguccaaaua cgucaacuuc cucuaccuug caucccauua cgaaaaacuc aagggaucgc    3840
cggaggacaa cgagcagaag cagcuuuucg uggagcaaca caagcauuac uuggacgaga    3900
ucaucgagca gauuuccgag uucucaaagc gcugauccu ggccgacgca aaucuggaca     3960
agguccuguc cgcguacaau aagcaucggg acaagccuau ccgcgaacag gccgagaaca    4020
ucauccaucu guucacucug acaaaccugg gcgcacccgc cgcguucaag uacuuugaca    4080
ccaccaucga uaggaagcga uacaccucaa cuaaggaagu guuggacgcg acccuuaucc    4140
aucagucgau caccgggcug uacgaaacac ggaucgaccu cagccaguug ggaggcgaca    4200
agcgcccugc ggcuaccaag aaggccggac aggccaagaa gaagaaauga gcggccgcuu    4260
aauuaagcug ccuucugcgg ggcuugccuu cuggccaugc ccuucuucuc ucccuugcac    4320
cuguaccucu ggucuuuga auaaagccug aguaggaagu cuagaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaa                                                                 4504

<210> SEQ ID NO 15
<211> LENGTH: 47
<212> TYPE: RNA
<213> ORGANISM: Artificial Sequence
<220> FEATURE:
<223> OTHER INFORMATION: Synthetic

<400> SEQUENCE: 15
aggaaauaag agagaaaaga agaguaagaa gaaauauaag agccacc                  47

<210> SEQ ID NO 16
<211> LENGTH: 4444
<212> TYPE: DNA
<213> ORGANISM: Artificial Sequence
<220> FEATURE:
<223> OTHER INFORMATION: Synthetic

<400> SEQUENCE: 16
aggaaataag agagaaaaga agagtaagaa gaaatataag agccaccatg gccccaaaga     60
agaagcggaa ggtcggtatc cacggagtcc cagcagccga caagaagtac agcatcggcc    120
tggacatcgg caccaactct gtgggctggg ccgtgatcac cgacgagtac aaggtgccca    180
gcaagaaatt caaggtgctg gcaacaccg accggcacag catcaagaag aacctgatcg    240 agccctgct gttcgacagc ggcgaaacag ccgaggccac ccggctgaag agaaccgcca    300
gaagaagata caccagacgg aagaaccgga tctgctatct gcaagagatc ttcagcaacg    360
agatggccaa ggtggacgac agcttcttcc acagactgga agagtccttc ctggtggaag    420
```

```
aggacaagaa gcacgagaga cacccatct tcggcaacat cgtggacgag gtggcctacc    480
acgagaagta ccccaccatc taccacctga gaaagaaact ggtggacagc accgacaagg    540
ccgacctgag actgatctac ctggccctgg cccacatgat caagttcaga ggccacttcc    600
tgatcgaggg cgacctgaac cccgacaaca gcgacgtgga caagctgttc atccagctgg    660
tgcagaccta caaccagctg ttcgaggaaa accccatcaa cgccagcggc gtggacgcca    720
aggctatcct gtctgccaga ctgagcaaga gcagaaggct ggaaaatctg atcgcccagc    780
tgcccggcga gaagaagaac ggcctgttcg gcaacctgat tgccctgagc ctgggcctga    840
cccccaactt caagagcaac ttcgacctgg ccgaggatgc caaactgcag ctgagcaagg    900
acacctacga cgacgacctg gacaacctgc tggcccagat cggcgaccag tacgccgacc    960
tgttcctggc cgccaagaac ctgtctgacg ccatcctgct gagcgacatc ctgagagtga   1020
acaccgagat caccaaggcc cccctgagcg cctctatgat caagagatac gacgagcacc   1080
accaggacct gaccctgctg aaagctctcg tgcggcagca gctgcctgag aagtacaaag   1140
aaatcttctt cgaccagagc aagaacggct acgccggcta catcgatggc ggcgctagcc   1200
aggaagagtt ctacaagttc atcaagccca tcctggaaaa gatggacggc accgaggaac   1260
tgctcgtgaa gctgaacaga gaggacctgc tgagaaagca gagaaccttc gacaacggca   1320
gcatccccca ccagatccac ctgggagagc tgcacgctat cctgagaagg caggaagatt   1380
tttacccatt cctgaaggac aaccgggaaa agatcgagaa gatcctgacc ttcaggatcc   1440
cctactacgt gggcccctg gccagaggca acagcagatt cgcctggatg accagaaaga   1500
gcgaggaaac catcaccccc tggaacttcg aggaagtggt ggacaagggc gccagcgccc   1560
agagcttcat cgagagaatg acaaacttcg ataagaacct gcccaacgag aaggtgctgc   1620
ccaagcacag cctgctgtac gagtacttca ccgtgtacaa cgagctgacc aaagtgaaat   1680
acgtgaccga gggaatgaga aagcccgcct tcctgagcgg cgagcagaaa aaggccatcg   1740
tggacctgct gttcaagacc aacagaaaag tgaccgtgaa gcagctgaaa gaggactact   1800
tcaagaaaat cgagtgcttc gactccgtgg aaatctccgg cgtggaagat agattcaacg   1860
cctccctggg cacataccac gatctgctga aaattatcaa ggacaaggac ttcctggata   1920
acgaagagaa cgaggacatt ctggaagata tcgtgctgac cctgacactg tttgaggacc   1980
gcgagatgat cgaggaaagg ctgaaaacct acgctcacct gttcgacgac aaagtgatga   2040
agcagctgaa gagaaggcgg tacaccggct ggggcaggct gagcagaaag ctgatcaacg   2100
gcatcagaga caagcagagc ggcaagacaa tcctggattt cctgaagtcc gacggcttcg   2160
ccaaccggaa cttcatgcag ctgatccacg acgacagcct gacattcaaa gaggacatcc   2220
agaaagccca ggtgtccggc cagggcgact ctctgcacga gcatatcgct aacctggccg   2280
gcagccccgc tatcaagaag ggcatcctgc agacagtgaa ggtggtggac gagctcgtga   2340
aagtgatggg cagacacaag cccgagaaca tcgtgatcga gatggctaga gagaaccaga   2400
ccacccagaa gggacagaag aactcccgcg agaggatgaa gagaatcgaa gagggcatca   2460
aagagctggg cagccagatc ctgaaagaac accccgtgga aaacacccag ctgcagaacg   2520
agaagctgta cctgtactac ctgcagaatg gccgggatat gtacgtggac caggaactgg   2580
acatcaacag actgtccgac tacgatgtgg accatatcgt gcctcagagc tttctgaagg   2640
acgactccat cgataacaaa gtgctgactc ggagcgacaa gaacagaggc aagagcgaca   2700
acgtgccctc cgaagaggtc gtgaagaaga tgaagaacta ctggcgacag ctgctgaacg   2760
ccaagctgat tacccagagg aagttcgata acctgaccaa ggccgagaga ggcggcctga   2820
```

```
gcgagctgga taaggccggc ttcatcaaga ggcagctggt ggaaaccaga cagatcacaa    2880
agcacgtggc acagatcctg gactcccgga tgaacactaa gtacgacgaa aacgataagc    2940
tgatccggga agtgaaagtg atcaccctga agtccaagct ggtgtccgat tccggaagg     3000 atttccagtt ttacaaagtg cgcgagatca acaactacca ccacgccac gacgcctacc    3060 tgaacgccgt cgtgggaacc gccctgatca aaaagtaccc taagctggaa agcgagttcg    3120
tgtacggcga ctacaaggtg tacgacgtgc ggaagatgat cgccaagagc gagcaggaaa    3180
tcggcaaggc taccgccaag tacttcttct acagcaacat catgaacttt ttcaagaccg    3240
aaatcaccct ggccaacggc gagatcagaa agcgccctct gatcgagaca aacggcgaaa    3300
ccggggagat cgtgtgggat aagggcagag acttcgccac agtgcgaaag gtgctgagca    3360
tgccccaagt gaatatcgtg aaaaagaccg aggtgcagac aggcggcttc agcaaagagt    3420
ctatcctgcc caagaggaac agcgacaagc tgatcgccag aaagaaggac tgggacccca    3480
agaagtacgg cggcttcgac agccctaccg tggcctactc tgtgctggtg gtggctaagg    3540
tggaaaaggg caagtccaag aaactgaaga gtgtgaaaga gctgctgggg atcaccatca    3600
tggaaagaag cagctttgag aagaacccta tcgactttct ggaagccaag ggctacaaag    3660
aagtgaaaaa ggacctgatc atcaagctgc ctaagtactc cctgttcgag ctggaaaacg    3720
gcagaaagag aatgctggcc tctgccggcg aactgcagaa gggaaacgag ctggcctgc     3780 ctagcaaata tgtgaacttc ctgtacctgg cctcccacta tgagaagctg aagggcagcc    3840
ctgaggacaa cgaacagaaa cagctgtttg tggaacagca taagcactac ctggacgaga    3900
tcatcgagca gatcagcgag ttctccaaga gagtgatcct ggccgacgcc aatctggaca    3960
aggtgctgtc tgcctacaac aagcacaggg acaagcctat cagagagcag gccgagaata    4020
tcatccacct gttcaccctg acaaacctgg gcgctcctgc cgccttcaag tactttgaca    4080
ccaccatcga ccggaagagg tacaccagca ccaaagaggt gctggacgcc accctgatcc    4140
accagagcat caccggcctg tacgagacaa gaatcgacct gtctcagctg ggaggcgaca    4200
agagacctgc cgccactaag aaggccgac  aggccaaaaa gaagaagtga gcggccgctt    4260
aattaagctg ccttctgcgg ggcttgcctt ctggccatgc ccttcttctc tcccttgcac    4320
ctgtacctct tggtctttga ataaagcctg agtaggaagt ctagaaaaaa aaaaaaaaa     4380 aaaaaaaaa aaaaaaaaa aaaaaaaaa aaaaaaaaa aaaaaaaaa aaaaaaaaa          4440 aaaa                                                                  4444

<210> SEQ ID NO 17
<211> LENGTH: 4444
<212> TYPE: RNA
<213> ORGANISM: Artificial Sequence
<220> FEATURE:
<223> OTHER INFORMATION: Synthetic

<400> SEQUENCE: 17
aggaaauaag agagaaaaga agaguaagaa gaaauauaag agccaccaug gccccaaaga     60
agaagcggaa ggucgguauc cacggagucc cagcagccga caagaaguac agcaucggcc    120
uggacaucgg caccaacucu guggguggg ccgugaucac cgacgaguac aaggugccca    180
gcaagaaauu caaggugcug ggcaacaccg accggcacag caucaagaag aaccugaucg    240
gagcccugcu guucgacagc ggcgaaacag ccgaggccac ccggcugaag agaaccgcca    300
gaagaagaua caccagacgg aagaaccgga ucugcuaucu gcaagagauc uucagcaacg    360
```

```
agauggccaa gguggacgac agcuucuucc acagacugga agaguccuuc cugguggaag    420
aggacaagaa gcacgagaga caccccaucu ucggcaacau cguggacgag guggccuacc    480
acgagaagua ccccaccauc uaccaccuga gaaagaaacu gguggacagc accgacaagg    540
ccgaccugag acugaucuac cuggcccugg cccacaugau caaguucaga ggccacuucc    600
ugaucgaggg cgaccugaac cccgacaaca gcgacgugga caagcuguuc auccagcugg    660
ugcagaccua caaccagcug uucgaggaaa accccaucaa cgccagcggc guggacgcca    720
aggcuauccu gucugccaga cugagcaaga gcagaaggcu ggaaaaucug aucgcccagc    780
ugcccggcga agaagaac ggccuguucg caaccugau gcccugagc cugggccuga    840 cccccaacuu caagagcaac uucgaccugg ccgaggaugc caaacugcag cugagcaagg    900
acaccuacga cgacgaccug acaaccugc uggcccagau cggcgaccag uacgccgacc    960
uguuccuggc cgccaagaac cugucugacg ccauccugcu gagcgacauc cugagaguga   1020
acaccgagau caccaaggcc ccccugagcc ccucuaugau caagagauac gacgagcacc   1080
accaggaccu gacccugcug aaagcucucg ugcggcagca gcugccugag aaguacaaag   1140
aaaucuucuu cgaccagagc aagaacggca cgccggcua caucgauggc ggcgcuagcc   1200
aggaagaguu cuacaaguuc aucagcccca uccuggaaaa gauggacggc accgaggaac   1260
ugcucgugaa gcugaacaga gaggaccugc ugagaaagca gagaaccuuc gacaacggca   1320
gcauccccca ccagauccac cugggagagc ugcacgcuau ccgagaagg caggaagauu   1380 uuuacccauu ccugaaggac aaccgggaaa agaucgagaa gauccugacc uucaggaucc   1440
ccuacuacgu gggccccug gccagaggca acagcagauu cgccuggaug accagaaaga   1500
gcgaggaaac caucacccc uggaacuucg aggaaguggu ggacaagggc ccagcgccc    1560 agagcuucau cgagagaaug acaaacuucg auaagaaccu gcccaacgag aaggugcugc   1620
ccaagcacag ccugcucuac gaguacuuca ccguguacaa cgagcugacc aaagugaaau   1680
acgugaccga gggaaugaga aagcccgccu uccugagcgg cgagcagaaa aaggccaucg   1740
uggaccugcu guucaagacc aacagaaaag ugaccgugaa gcagcugaaa gaggacuacu   1800
ucaagaaaau cgagugcuuc gacuccgugg aaauuccgg cguggaagau agauucaacg   1860
ccucccuggg cacauaccac gaucugcuga aaauuaucaa ggacaaggac uuccuggaua   1920
acgaagagaa cgaggacauu cuggaagaua ucgucgac cugacacug uuugaggacc    1980 gcgagaugau cgaggaaagg cugaaaaccu acgcucaccu guucgacgac aaagugauga   2040
agcagcugaa gagaaggcgg uacaccggcu ggggcaggcu gagcagaaag cugaucaacg   2100
gcaucagaga caagcagagc ggcaagacaa uccuggauuu ccugaaguc gacggcuucg    2160 ccaaccggaa cuucaugcag cugauccacg acgacagccu gacauucaaa gaggacaucc   2220
agaaagccca ggguccggc cagggcgacu cucugcacga gcauaucgcu aaccuggccg    2280
gcagccccgc uaucaagaag ggcauccugc agacagugaa ggugguggac gagcucguga   2340
aagugauggg cagacacaag cccgagaaca ucgugaucga gauggcuaga gagaaccaga   2400
ccacccagaa gggacagaag aacucccgcg agaggaugaa gagaaucgaa gagggcauca   2460
aagagcuggg cagccagauc cugaaagaac ccccggugga aaacacccag cugcagaacg   2520
agaagcugua ccuguacuac cugcagaaug ccgggauau guacgugac caggaacugg    2580 acaucaacag acugucegac uacgauguge accaucgu gccucagagc uuucugaagg    2640
acgacuccau cgauaacaaa gugcugacuc ggagcgacaa gaacagaggc aagagcgaca   2700
acgugcccuc cgaagagguc gugaagaaga ugaagaacua cuggcgacag cugcugaacg   2760
```

```
ccaagcugau uacccagagg aaguucgaua accugaccaa ggccgagaga ggcggccuga   2820
gcgagcugga uaaggccggc uucaucaaga ggcagcuggu ggaaaccaga cagaucacaa   2880
agcacguggc acagauccug gacucccgga ugaacacuaa guacgacgaa aacgauaagc   2940
ugauccggga agugaaagug aucacccuga aguccaagcu gguguccgau uuccggaagg   3000
auuuccaguu uuacaaagug cgcgagauca acaacuacca ccacgcccac gacgccuacc   3060
ugaacgccgu cgugggaacc gcccugauca aaaaguaccc uaagcuggaa agcgaguucg   3120
uguacggcga cuacaaggug uacgacgugc ggaagaugau cgccaagagc gagcaggaaa   3180
ucggcaaggc uaccgccaag uacuucuucu acagcaacau caugaacuuu uucaagaccg   3240
aaaucacccu ggccaacggc gagaucagaa agcgcccucu gaucgagaca acggcgaaa    3300 ccggggagau cguguqqqau aagggcagag acuucgccac agugcgaaag gugcugagca   3360
ugccccaagu gaauaucgug aaaaagaccg aggugcagac aggcggcuuc agcaaagagu   3420
cuauccugcc caagaggaac agcgacaagc ugaucgccag aaagaaggac ugggacccca   3480
agaaguacgg cggcuucgac agcccuaccg uggccuacuc ugugcuggug guggcuaagg   3540
uggaaaaggg caaguccaag aaacugaaga gugugaaaga gcugcugggg aucaccauca   3600
uggaaagaag cagcuuugag aagaacccua ucgacuuucu ggaagccaag ggcuacaaag   3660
aagugaaaaa ggaccugauc aucaagcugc cuaaguacuc ccuguucgag cuggaaaacg   3720
gcagaaagag aaugcuggcc ucugccggcg aacugcagaa gggaaacgag cuggcccugc   3780
cuagcaaaua ugugaacuuc cuguaccugg ccucccacua ugagaagcug aagggcagcc   3840
cugaggacaa cgaacagaaa cagcuguuug uggaacagca uaagcacuac cuggacgaga   3900
ucaucgagca gaucagcgag uucuccaaga gagugauccu ggccgacgcc aaucuggaca   3960
aggugcuguc ugccuacaac aagcacaggg acaagccuau cagagagcag gccgagaaua   4020
ucauccaccu guucacccug acaaaccugg gcgcuccugc cgccuucaag uacuuugaca   4080
ccaccaucga ccggaagagg uacaccagca ccaaagaggu gcuggacgcc acccugaucc   4140
accagagcau caccggccug uacgagacaa gaaucgaccu gucucagcug ggaggcgaca   4200
agagaccugc cgccacuaag aaggccggac aggccaaaaa gaagaaguga gcggccgcuu   4260
aauuaagcug ccuucugcgg ggcuugccuu cuggccaugc ccuucuucuc ucccuugcac   4320
cuguaccucu uggucuuuga auaaagccug aguaggaagu cugaaaaaaa aaaaaaaaaa   4380
aaaaaaaaaa aaaaaaaaaa aaaaaaaaaa aaaaaaaaaa aaaaaaaaaa aaaaaaaaaa   4440
aaaa                                                               4444
```

MESSENGER RNA ENCODING Cas9 FOR USE IN GENOME-EDITING SYSTEMS

CROSS REFERENCE TO RELATED APPLICATIONS

The present application claims the benefit of priority to U.S. Provisional Patent Application No. 63/025,755, filed May 15, 2020, the disclosure of which is incorporated herein by reference in its entirety.

PARTIES TO A JOINT RESEARCH AGREEMENT

The claimed invention was made by, on behalf of, and/or in connection with one or more of the following parties to a joint research agreement: CRISPR THERAPEUTICS AG and BAYER HEALTHCARE LLC. The joint research agreement was in effect on or before the date the claimed invention was made, and the claimed invention was made as a result of activities undertaken within the scope of the joint research agreement.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "CB35_Seqlisting.txt", which was created on May 10, 2021 and is 67,435 bytes in size. The subject matter of the Sequence Listing is incorporated herein in its entirety by reference.

BACKGROUND

Recent advances in genome sequencing techniques and analysis methods have significantly accelerated the ability to identify and map genetic elements associated with a diverse range of biological functions and diseases. Precise genome targeting technologies are needed to enable reverse engineering of causal genetic variations by allowing selective perturbation of individual genetic elements, as well as to advance synthetic biology, biotechnological, and medical applications. In recent years, targeted genome editing technologies using engineered nucleases have progressed from being niche technologies to advanced methods used by many biological researchers. This adoption has been largely fueled by the emergence of a new class of site-specific endonucleases, including designer zinc fingers, transcription activator-like effectors (TALEs), homing meganucleases, and the development of the clustered, regularly interspaced, short palindromic repeat (CRISPR) technology.

The CRISPR/Cas9 system, which includes an RNA-guided nuclease (Cas9) and one or more guide RNAs (gRNAs), has become a powerful tool for manipulating/editing genomes. Upon delivery of Cas9 polypeptide and gRNA to the nucleus of a cell, the gRNA directs Cas9 to a target gene sequence and the Cas9/gRNA complex generates a site-specific DNA double-strand break (DSB). These DSBs are repaired by endogenous cellular mechanisms, including non-homologous end joining (NHEJ) and homology directed repair (HDR), which can, for example, introduce a mutation in the target gene through formation of insertions or deletions (indels) at the DSB or introduce an exogenous nucleotide sequence by insertion at the DSB.

Application of the CRISPR/Cas9 system depends upon effective delivery, as well as expression/activity, of system components to target cells, which can be challenging for large biomolecules such as Cas9. Various methods of introducing Cas9 to target cells have been explored, but each have drawbacks. For example, plasmid or viral vectors have been used for Cas9 delivery. However, such methods suffer the risk of vector integration into the genome. Recombinant Cas9 polypeptide complexed to gRNA (i.e., ribonucleoprotein or RNP complexes) has also been used for delivery. However, the stability of such complexes in cells or plasma is limited, which can be detrimental for certain genome editing applications. In addition, mRNA expressing Cas9 can induce innate immune responses, reducing Cas9 expression. Thus, there remains a need for compositions and methods that enable efficient delivery and expression/activity of CRISPR/Cas9 system components to target cells and tissues for broad application to methods of genome editing.

SUMMARY

The present disclosure provides optimized messenger RNAs (mRNAs) encoding a site-directed endonuclease, such as an *S. pyogenes* Cas9 endonuclease ("SpCas9 mRNA"), which, when combined with one or gRNAs provide effective genome editing of target cells. In some aspects, the disclosure provides an mRNA comprising a 5' untranslated region (UTR); an open reading frame (ORF) comprising a nucleotide sequence that encodes a site-directed endonuclease, wherein the nucleotide sequence is at least 85% identical to a nucleotide sequence of SEQ ID NO: 4; and a 3' untranslated region (UTR). In some aspects, the mRNA comprises at least one chemically modified nucleoside. In some aspects, the chemically modified nucleoside is selected from pseudouridine, N1-methylpseudouridine, and 5-methoxyuridine. In some aspects, the chemically modified nucleoside is N1-methylpseudouridine. In some aspects, at least about 80% of the uridines are chemically modified. In some aspects, 100% of the uridines are chemically modified. In some aspects, the uridines are modified and/or replaced with N1-methylpseudouridine.

In some aspects, the disclosure provides an mRNA comprising: a 5' UTR; an ORF comprising a nucleotide sequence that encodes a site-directed endonuclease, wherein the nucleotide sequence is at least 85% identical to the nucleotide sequence of SEQ ID NO: 4; and a 3' UTR, wherein 100% of the uridines of the mRNA are modified and/or replaced with N1-methylpseudouridine.

In any of the foregoing or related aspects, the 5' UTR comprises a nucleotide sequence of SEQ ID NO: 10 or SEQ ID NO: 15. In some aspects, the 3' UTR comprises a nucleotide sequence of SEQ ID NO: 12.

In any of the foregoing or related aspects, the mRNA further comprises a poly-A tail. In some aspects, the poly-A tail is about 100 to about 1000, about 10 to about 500, about 10 to about 300, about 10 to about 200, about 50 to about 200, about 50 to about 150, about 100 to about 150, or about 120 to about 150 adenosine nucleotides.

In any of the foregoing or related aspects, the mRNA comprises the nucleotide sequence of SEQ ID NO: 2 or SEQ ID NO: 14.

In some aspects, the disclosure provides an mRNA comprising a nucleotide sequence of SEQ ID NO: 2 or SEQ ID NO: 14, wherein 100% of the uridines of the mRNA are modified and/or replaced with N1-methylpseudouridine.

In any of the foregoing or related aspects, the mRNA comprises a 5' cap. In some aspects, the 5' cap is a cap-0, a cap-1, or a cap-2 structure.

In some aspects, the disclosure provides a system for editing a target gene in a genomic DNA molecule in a cell, the system comprising (a) an mRNA described herein; and (b) at least one guide RNA (gRNA) directed to the target gene, wherein the mRNA is translated when the mRNA contacts the cell and provides a site-directed endonuclease that combines with the gRNA to induce a double-stranded DNA break (DSB) at a site in the target gene.

In some aspects, the disclosure provides a system for introducing a double-stranded DNA break (DSB) in a target gene in a cell, the system comprising (a) an mRNA described herein; and (b) at least one guide RNA (gRNA) directed to the target gene, wherein the mRNA is translated when the mRNA contacts the cell and provides a site-directed endonuclease that combines with the gRNA to induce a DSB at a site in the target gene.

In some aspects, the disclosure provides a system for correcting a mutation in a target gene in a cell, the system comprising: (a) an mRNA described herein; (b) at least one gRNA directed to the target gene; and (c) a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) or homology-directed DNA repair pathway inserts the donor polynucleotide into the DSB at a location proximal to the mutation, thereby correcting the mutation.

In any of the foregoing or related aspects, the mRNA and the gRNA are individually formulated in a lipid nanoparticle (LNP). In some aspects, the mRNA and the gRNA are co-formulated in an LNP. In some aspects, the donor polynucleotide is individually formulated in a LNP. In some aspects, the donor polynucleotide is encoded by an AAV.

In any of the foregoing or related aspects, the LNP comprises one or more lipid moieties selected from: an amino lipid, an ionizable lipid, a neutral lipid, a PEG-lipid, a helper lipid, a cholesterol or derivative thereof.

In some aspects, the disclosure provides a pharmaceutical composition comprising: an mRNA described herein or a system described herein, and a pharmaceutically acceptable carrier. In some aspects, the pharmaceutical composition further comprises at least one gRNA directed to a target gene. In some aspects, the pharmaceutical composition further comprises a donor polynucleotide.

In some aspects, the disclosure provides a method for editing a target gene in a genomic DNA molecule in a cell, the method comprising: contacting the cell with: (i) an mRNA described herein and at least one gRNA directed to the target gene; (ii) a system described herein; or (iii) a pharmaceutical composition described herein, wherein the mRNA is translated when the mRNA, the system, or the composition contacts the cell and provides a site-directed endonuclease that combines with the gRNA to induce a DSB at a site in the target gene.

In some aspects, the disclosure provides a method for inducing a DSB in a target gene in a cell, the method comprising: contacting the cell with: (i) an mRNA described herein and at least one gRNA directed to the target gene; (ii) a system described herein; or (iii) a pharmaceutical composition described herein, wherein the mRNA is translated when the mRNA, the system, or the composition contacts the cell and provides a site-directed endonuclease that combines with the gRNA to induce a DSB at a site in the target gene.

In some aspects, the disclosure provides a method of treating a patient with a disease by editing a target gene in a genomic DNA molecule in a cell, the method comprising: isolating a cell from the patient, and contacting the cell with: (i) an mRNA described herein and at least one gRNA directed to the target gene; (ii) a system described herein; or (iii) a pharmaceutical composition described herein, wherein the mRNA is translated when the mRNA, system, or composition contacts the cell and provides a site-directed endonuclease that combines with the gRNA to induce a DSB at a site in the target gene.

In some aspects, the disclosure provides a method of treating a patient with a disease by inducing a DSB in a target gene in a cell, the method comprising: isolating a cell from the patient, and contacting the cell with: (i) an mRNA described herein and at least one gRNA directed to the target gene; (ii) a system described herein; or (iii) a pharmaceutical composition described herein, wherein the mRNA is translated when the mRNA, system, or composition contacts the cell and provides a site-directed endonuclease that combines with the gRNA to induce a DSB at a site in the target gene.

In some aspects, the disclosure provides a method of treating a patient with a disease by editing a target gene in a genomic DNA molecule in a cell, the method comprising: administering to the patient an effective amount of (i) an mRNA described herein and at least one gRNA directed to the target gene; (ii) a system described herein; or (iii) a pharmaceutical composition described herein, wherein the mRNA is translated when the mRNA, system, or composition contacts the cell and provides a site-directed endonuclease that combines with the gRNA to induce a DSB at a site in the target gene.

In some aspects, the disclosure provides a method of treating a patient with a disease by inducing a DSB in a target gene in a cell, the method comprising: administering to the patient an effective amount of (i) an mRNA described herein and at least one gRNA directed to the target gene; (ii) a system described herein; or (iii) a pharmaceutical composition described herein, wherein the mRNA is translated when the mRNA, system, or composition contacts the cell and provides a site-directed endonuclease that combines with the gRNA to induce a DSB at a site in the target gene.

In some aspects, the disclosure provides a method for correcting a mutation in a target gene in a cell, the method comprising: contacting the cell with an mRNA described herein, at least one gRNA directed to the target gene, and a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) or homology-directed DNA repair pathway inserts the donor polynucleotide into the DSB at a location proximal to the mutation, thereby correcting the mutation.

In some aspects, the disclosure provides a method of treating a patient with a disease by correcting a mutation in a target gene in a cell, the method comprising: isolating a cell from the patient; and contacting the cell with an mRNA described herein, at least one gRNA directed to the target gene, and a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) or homology-directed DNA repair pathway inserts the donor polynucleotide into the DSB at a location proximal to the mutation, thereby correcting the mutation.

In some aspects, the disclosure provides a method of treating a patient with a disease by correcting a mutation in a target gene in a cell, the method comprising: administering to the patient an effective amount of an mRNA described herein, at least one gRNA directed to the target gene, and a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) or homology-directed DNA repair pathway inserts the donor polynucleotide into the DSB at a location proximal to the mutation, thereby correcting the mutation.

In some aspects, the disclosure provides a kit for inducing a DSB in a target gene in a cell, the kit comprising: a container comprising an mRNA described herein, a system described herein, or a pharmaceutical composition described herein, and a package insert comprising instructions for use.

DETAILED DESCRIPTION

Overview

Figure 1:
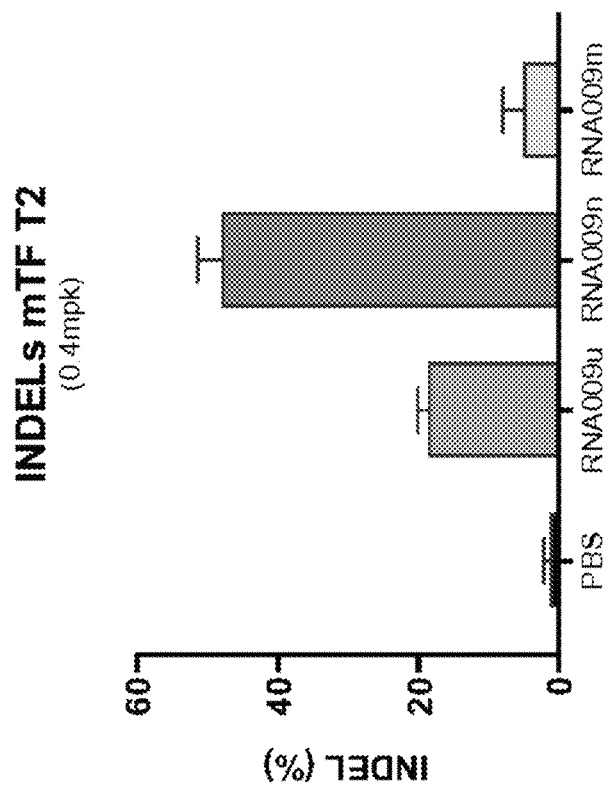
FIG. 1 provides a graph showing frequency of INDELs in liver tissue of mice administered lipid nanoparticles (LNPs) containing gRNA targeting the mouse transferrin gene locus (mTF_T2 sgRNA) and sequence-optimized mRNA encoding SpCas9 (RNA-009 mRNA). RNA-009 mRNA contained either unmodified uridine (RNA-009u), N1-methylpseudouridine (RNA-009n), or 5-methoxyuridine (RNA-009m). Comparison was made to control mice administered PBS only.

The present disclosure provides optimized mRNAs encoding an *S. pyogenes* Cas9 endonuclease ("SpCas9 mRNA"), and which optionally include chemically modified nucleotides, that provide effective genome editing of a target cell population when administered with one or more gRNAs. As described herein, approaches were discovered that resulted in an optimized SpCas9 mRNA with improved translation and/or SpCas9 polypeptide activity. Without being bound by theory, it is believed that such optimized mRNAs increase translation in target cells and tissues and reduces activation of RNA-responsive innate immune response pathways that can trigger an adaptive immune response against the CRISPR/Cas9 system. In some embodiments, the mRNA is codon optimized for effective translation in host cells (e.g., human cells). In some embodiments, the SpCas9 mRNA is chemically modified, for example, to minimize uridine-rich sequences that trigger innate immune response pathways. As described herein, a combination of approaches provided an optimized SpCas9 mRNA, which optionally include chemically modified nucleotides, that was highly effective for use in methods of genome editing when administered in vivo.

In some aspects, the disclosure provides CRISPR/Cas9 systems comprising the optimized SpCas9 mRNA described herein for use in editing a target gene in a cell, e.g., following in vivo or in vitro administration. In some aspects, the CRISPR/Cas9 system comprises an optimized SpCas9 mRNA described herein and one or more gRNAs for introducing a DSB in a target gene in a cell, for example, to introduce a mutation or correct a mutation in a target gene. In some aspects, the CRISPR/Cas9 system further comprises a donor polynucleotide, for example, to introduce a sequence-specific gene-edit by a NHEJ or HDR repair pathway.

In further aspects, the disclosure also provides methods of delivery of CRISPR/Cas9 system components described herein. For example, in some embodiments, the disclosure provides lipid nanoparticle (LNP) formulations for separate or co-formulation of SpCas9 mRNA and one or more gRNAs. Indeed, it was discovered that the LNP formulations described herein comprising an optimized SpCas9 mRNA of the disclosure were highly effective for introducing gene edits when evaluated with gRNAs targeting different gene loci and following in vivo administration in both mouse and non-human primate animal models. Moreover, the level of editing efficiency could be readily controlled by titrating the dose of the optimized SpCas9 mRNA administered (i.e., dose responsive efficacy).

Thus, provided herein, are compositions and methods for delivery of CRISPR/Cas9 system components (e.g., SpCas9 mRNA and one or more gRNAs) for use in effective genome editing of target tissues and cells while reducing undesirable immune cell activation.

Messenger RNAs Encoding a Site-Directed Endonuclease

In some aspects, the disclosure provides an mRNA encoding a site-directed endonuclease, such as a SpCas9 polypeptide, for use in methods of genome editing using a CRISPR/Cas system. In some embodiments, the mRNA comprises a 5' UTR, an open reading frame (ORF) comprising a nucleotide sequence encoding a site-directed endonuclease, such as a SpCas9 polypeptide, and a 3' UTR.

In some embodiments, an mRNA of the disclosure comprises at least one modification. In some embodiments, the at least one modification provides (i) improved mRNA stability, for example, in serum or in cells, (ii) improved mRNA translation efficiency, and/or (iii) reduced activation of innate immune signaling pathways compared to an equivalent unmodified mRNA. In some embodiments, the at least one modification improves the level and/or duration of expression of the encoded site-directed endonuclease, such as SpCas9 polypeptide, in a target tissue or cell following systemic administration of the mRNA (e.g., as compared to an equivalent unmodified mRNA). In some embodiments, the at least one modification reduces activation of innate immune cell responses following systemic administration of the mRNA (e.g., as compared to an equivalent unmodified mRNA).

In some embodiments, the at least one modification is selected from: (i) sequence optimization of the mRNA, (ii) chemical modification of at least one nucleotide of the mRNA, or (iii) a combination of (i) and (ii).

I. Sequence Optimization

In some embodiments, an mRNA of the disclosure comprises a sequence-optimized nucleotide sequence. In some embodiments, the mRNA comprises a nucleotide sequence that is sequence optimized for expression in a target cell. In some embodiments, the target cell is a mammalian cell. In some embodiments, the target cell is a human cell, a murine cell, or a non-human primate (NHP) cell.

A sequence-optimized nucleotide sequence, e.g., a codon-optimized mRNA sequence encoding a site-directed endonuclease, such as a SpCas9 polypeptide, typically is a sequence comprising at least one synonymous nucleobase substitution with respect to a reference sequence (e.g., a non-optimized mRNA sequence encoding a site-directed endonuclease, such as a SpCas9 polypeptide). A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to as codon optimization) methods are known in the art and can be useful to achieve one or more desired results. These results can include, e.g., matching codon frequencies in certain tissue targets and/or host organisms to ensure proper folding; uridine depletion; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide.

In some embodiments, an mRNA of the disclosure comprises a nucleotide sequence that is sequence-optimized relative to a reference sequence using a method of sequence optimization. Methods of sequence optimization are known in the art, and include known sequence optimization tools, algorithms and services. Non-limiting examples include services from GeneArt (Life Technologies), DNA2.0 (Menlo Park CA), Geneious®, GeneGPS® (Atum, Newark, CA), and/or proprietary methods. In some embodiments, an mRNA of the disclosure comprises a nucleotide sequence that is sequence-optimized relative to a reference sequence using a method of sequence optimization (e.g., GeneGPS®, e.g., Geneious®). In some embodiments, the method of sequence optimization comprises any one codon optimization algorithm described in U.S. Pat. Nos. 7,561,972; 7,561,973; 8,126,653; and 8,401,798, each of which is incorporated herein by reference. In some embodiments, the nucleotide sequence is (i) sequence-optimized based on codon usage bias in a host cell (e.g., mammalian cell, e.g., human cell, murine cell, non-human primate cell) relative to a reference sequence, (ii) uridine-depleted relative to a reference sequence, or (iii) a combination of (i) and (ii), using a method of sequence optimization (e.g., GeneGPS®, e.g., Geneious®).

In some embodiments, the reference sequence comprises the nucleotide sequence of SEQ ID NO: 17. In some embodiments, the sequence-optimized nucleotide sequence comprises one or more nucleobase substitutions relative to the reference sequence. In some embodiments, the sequence-optimized nucleotide sequence is less than about 95%, about 94%, about 93%, about 92%, about 91%, about 90%, about 89%, about 88%, about 87%, about 86%, about 85%, about 84%, about 83%, about 82%, about 81%, or about 80% identical to the reference sequence. In some embodiments, the sequence-optimized nucleotide sequence is at least about 80%, at least about 81%, at least about 82%, at least about 83%, at least about 84%, at least about 85%, at least about 86%, at least about 87%, at least about 88%, at least about 89, at least about 90%, at least about 91%, at least about 92%, at least about 93%, at least about 94%, at least about 95%, at least about 96%, at least about 97%, at least about 98%, or at least about 99% identical to the reference sequence. In some embodiments, the polypeptide encoded by the sequence-optimized nucleotide sequence is 100% identical to the polypeptide encoded by the reference sequence. In some embodiments, the polypeptide encoded by the sequence-optimized nucleotide sequence is set forth in SEQ ID NO: 5.

In some embodiments, the sequence-optimized nucleotide sequence is uridine depleted, e.g., compared to the reference sequence, e.g., compared to the nucleotide sequence of SEQ ID NO: 17. In some embodiments, the uracil content of the sequence-optimized nucleotide sequence is decreased (e.g., by about 1.1-fold, 1.2-fold, 1.3-fold, 1.4-fold, or about 1.5-fold) compared to the reference sequence, e.g., the nucleotide sequence of SEQ ID NO: 17.

In some embodiments, the sequence-optimized nucleotide sequence is not uridine depleted, e.g., compared to the reference sequence, e.g., compared to the nucleotide sequence of SEQ ID NO: 17. In some embodiments, the uracil content of the sequence-optimized nucleotide sequence is substantially equivalent (e.g., about 95% to about 105% similar) or increased (e.g., by about 1.1-fold, about 1.2-fold, about 1.3-fold, about 1.4-fold, or about 1.5-fold) compared to the reference sequence, e.g., the nucleotide sequence of SEQ ID NO: 17.

In some embodiments, the disclosure provides an mRNA comprising a sequence-optimized nucleotide sequence, wherein the mRNA has one or more improved properties (e.g., compared to an mRNA comprising the reference sequence, e.g., compared to an mRNA comprising the nucleotide sequence of SEQ ID NO: 17). In some embodiments, the one or more improved properties relates to expression efficacy after administration in vivo. In some embodiments, the one or more improved properties include, but are not limited to, increased cutting efficiency and/or activity, improving mRNA stability, increasing translation efficacy in the target tissue or target cell, reducing the number of truncated proteins expressed, improving folding or prevent misfolding of the expressed proteins, reducing toxicity of the expressed products, reducing cell death caused by the expressed products, increasing and/or decreasing protein aggregation, or a combination thereof.

In some embodiments, the sequence-optimized nucleotide sequence is codon optimized for expression in human subjects, having structural and/or chemical features that avoid or reduce one or more of the problems known in the art, for example, features that are useful for optimizing formulation and delivery of mRNA-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

II. Modified mRNAs

In some embodiments, the disclosure provides mRNAs with chemistries suitable for delivery, tolerability, and stability within cells, e.g., following in vivo or in vitro administration. Accordingly, in some embodiments, mRNAs described herein are modified, e.g., comprise a modified sugar moiety, a modified internucleoside linkage, a modified nucleoside, a modified nucleotide and/or combinations thereof. In some embodiments, the modified mRNAs exhibit one or more of the following properties: are not immune stimulatory; are nuclease resistant; have improved cell uptake; have increased half-life; have increased translation efficiency; and/or are not toxic to cells or mammals, e.g., following contact with cells in vivo or ex vivo or in vitro.

Additionally, certain nucleotide and nucleoside modifications have been shown to reduce immune stimulation, e.g., stimulation of innate immune pathways, by exogenous mRNA (see, e.g., Kariko, K, et al (2005) *IMMUNITY* 23:165; Anderson, et al (2011) *NUCLEIC ACIDS RES* 39:9329; Warren et al (2010) *CELL STEM CELL* 7:618).

Accordingly, the disclosure provides mRNA comprising chemical modification of one or more nucleosides/nucleotides. In some embodiments, one or more uridines of the mRNA are chemically-modified or replaced with a chemically-modified nucleoside. In some embodiments, the chemically-modified nucleoside selected from: pseudouridine, N1-methylpseudouridine, and 5-methoxyuridine. In some embodiments, the chemically-modified nucleoside is any one described in WO/2017/181107, WO/2018/144775, or WO/2020/056304, each of which is incorporated by reference herein.

In some embodiments, about 100% of the uridines of the mRNA are chemically-modified. In some embodiments, about 95% of the uridines of the mRNA are chemically-modified. In some embodiments, about 90% of the uridines of the mRNA are chemically-modified. In some embodiments, about 85% of the uridines of the mRNA are chemically-modified. In some embodiments, about 80% of the uridines of the mRNA are chemically-modified.

In some embodiments, about 100% of the uridines of the mRNA are chemically-modified and/or replaced with N1-methylpseudouridine. In some embodiments, about 95% of the uridines of the mRNA are chemically-modified and/or replaced with N1-methylpseudouridine. In some embodiments, about 90% of the uridines of the mRNA are chemically-modified and/or replaced with N1-methylpseudouridine. In some embodiments, about 85% of the uridines of the mRNA are chemically-modified and/or replaced with N1-methylpseudouridine. In some embodiments, about 80% of the uridines of the mRNA are chemically-modified and/or replaced with N1-methylpseudouridine.

In some embodiments, the modified nucleobase is N1-methylpseudouridine, and the mRNA of the disclosure is fully modified with N1-methylpseudouridine. In some embodiments, N1-methylpseudouridine represents from 75-100% of the uracils in the mRNA. In some embodiments, N1-methylpseudouridine represents 100% of the uracils in the mRNA.

In some embodiments, an mRNA of the disclosure is modified in the coding region (e.g., an open reading frame encoding a site-directed endonuclease, such as a SpCas9 polypeptide). In some embodiments, the mRNA is modified in regions besides a coding region. For example, in some embodiments, a 5' UTR and/or a 3' UTR are provided, wherein either or both may independently contain one or more different nucleoside modifications. In such embodiments, nucleoside modifications may also be present in the coding region.

Additional modifications of the mRNA encompassed by the present disclosure are further described below.

III. Messenger RNA Components

In some embodiments, the disclosure provides an mRNA comprising an open-reading frame (ORF), wherein the ORF comprises a nucleotide sequence that encodes a site-directed endonuclease, such as a Cas nuclease, wherein the Cas nuclease is a SpCas9 polypeptide. In some embodiments, the Cas nuclease comprises at least one domain that interacts with a guide RNA (gRNA). Additionally, the Cas nuclease is directed to a target sequence by a guide RNA. The guide RNA interacts with the Cas nuclease as well as the target sequence such that, once directed to the target sequence, the Cas nuclease is capable of cleaving the target sequence. In some embodiments, the guide RNA provides the specificity for the cleavage of the target sequence, and the Cas nuclease are universal and paired with different guide RNAs to cleave different target sequences.

In some embodiments, an mRNA of the disclosure comprises a 5' untranslated region (5' UTR), a 3' untranslated region (3' UTR), and an ORF comprising a nucleotide sequence encoding a site-directed endonuclease, such as a SpCas9 polypeptide. In some embodiments, the mRNA further comprises a 5' cap structure, a Kozak or Kozak-like sequence (also known as a Kozak consensus sequence), a polyA sequence (also known as a polyadenylation signal), a nucleotide sequence encoding a nuclear localization signal (NLS), a nucleotide sequence encoding a linker peptide, a nucleotide sequence encoding a tag peptide, or any combination thereof. In some embodiments, the consensus Kozak consensus sequence facilitates the initial binding of mRNA to ribosomes, thereby enhances its translation into a polypeptide product.

In some embodiments, an mRNA of the disclosure comprises any suitable number of base pairs, e.g., thousands (e.g., 4000, 5000, 6000, 7000, 8000, 9000, or 10,000) of base pairs. In some embodiments, the mRNA is about 4.2 kb, about 4.3 kb, about 4.4 kb, about 4.5 kb, about 4.6 kb, about 4.7 kb, about 4.8 kb, about 4.9 kb, about 5.0 kb, about 5.1 kb, about 5.2 kb, about 5.3 kb, about 5.4 kb, about 5.5 kb, or more in length.

A. 5' and 3' Untranslated Regions (UTRs)

In some embodiments, the 5' UTR or 3' UTR is derived from a human gene sequence. Non-limiting exemplary 5' UTR and 3' UTR include those derived from genes encoding α- and β-globin, albumin, HSD17B4, and eukaryotic elongation factor 1a. In addition, viral-derived 5' UTR and 3' UTRs can also be used and include orthopoxvirus and cytomegalovirus UTR sequences. In some embodiments, the 5' UTR comprises the nucleotide sequence of SEQ ID NO: 10. In some embodiments, the 5' UTR comprises the nucleotide sequence of SEQ ID NO: 15. In some embodiments, the 3' UTR comprises the nucleotide sequence of SEQ ID NO: 12.

B. 5' Cap

In some embodiments, an mRNA of the disclosure comprises a 5' cap structure. A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m$^7$G(5')ppp(5')G, commonly written as m$^7$GpppG. This cap is a cap-0 where nucleotide N does not contain 2'OMe, or cap-1 where nucleotide N contains 2'OMe, or cap-2 where nucleotides N and N+1 contain 2'OMe. This cap may also be of the structure m2 7'3 "G(5')N as incorporated by the anti-reverse-cap analog (ARCA), and may also include similar cap-0, cap-1, and cap-2, etc., structures.

In some embodiments, the 5'cap is a CleanCap® (TriLink Biotechnologies) capping structure. Non-limiting examples of CleanCap® capping structures include CleanCap® Reagent GG (m7G(5')ppp(5')(2'OMeG)pG, CleanCap® Reagent AU (m7G(5')ppp(5')(2'OMeA)pU, and CleanCap® Reagent AG (m7(3'OMeG)(5')ppp(5')(2'OMeA)pG, In some embodiments, the 5' cap may regulate nuclear export; prevent degradation by exonucleases; promote translation; and promote 5' proximal intron excision. Stabilizing elements for caps include phosphorothioate linkages, boranophosphate modifications, and methylene bridges. In addition, caps may also contain a non-nucleic acid entity that acts as the binding element for eukaryotic translation initiation factor 4E, eIF4E.

C. Nuclear Localization Signal

In some embodiments, an mRNA of the disclosure further comprises a nucleotide sequence encoding a nuclear localization signal (NLS). In some embodiments, the nuclease is fused with more than one NLS. In some embodiments, one or more NLS is operably-linked to the N-terminus, C-terminus, or both, of the site-directed endonuclease, optionally via a peptide linker. In some embodiments, the NLS comprises a nucleoplasmin NLS and/or a SV40 NLS. In some embodiments, the nucleoplasmin NLS comprises the amino acid sequence of SEQ ID NO: 7. In some embodiments, the SV40 NLS comprises the amino acid sequence of SEQ ID NO: 8. In some embodiments, the mRNA comprises a nucleotide sequence encoding a nucleoplasmin NLS and a nucleotide sequence encoding an SV40 NLS.

D. Poly-A Tail

In some embodiments, an mRNA of the disclosure comprises a poly(A) tail (i.e., polyA sequence, i.e., polyadenylation signal). In some embodiments, the polyA sequence comprises entirely or mostly of adenine nucleotides or analogs or derivatives thereof. In some embodiments, the polyA sequence is a tail located adjacent (e.g., towards the 3' end) of a 3' UTR of an mRNA. In some embodiments, the polyA sequence promotes or increases the nuclear export, translation, and/or stability of the mRNA.

In some embodiments, the poly(A) tail is about 40 to about 300 nucleotides in length. In some embodiments, the tail is about 40 to about 100 nucleotides in length. In some embodiments, the tail is about 100 to about 300 nucleotides in length. In some embodiments, the tail is about 100 to about 200 nucleotides in length. In some embodiments, the tail is about 50 to about 200 nucleotides in length. In some embodiments, the tail is about 50 to about 250 nucleotides in length. In some embodiments, the tail is about 100, 110, 120, 130, 140, 150, 160, 170, 180, 190, or 200 nucleotides in length. In some embodiments, the poly(A) tail comprises modifications to prevent exonuclease degradation, including phosphorotioate linkages and modifications to the nucleobase.

In some embodiments, the poly(A) tail comprises a 3' "cap" comprising modified or non-natural nucleobases or other synthetic moieties.

IV. Exemplary mRNAs

In some embodiments, the disclosure provides an mRNA comprising (i) a 5' untranslated region (UTR); (ii) an open reading frame (ORF) comprising a nucleotide sequence that encodes a site-directed endonuclease; and (iii) a 3' untranslated region (UTR). In some embodiments, the site-directed endonuclease is a Cas nuclease. In some embodiments, the Cas nuclease is a Cas9 polypeptide. In some embodiments, the Cas 9 polypeptide is a *Streptococcus pyogenes*-derived Cas9 (SpCas9) polypeptide. In some embodiments, the ORF further comprises one or more nucleotide sequences encoding a nuclear localization signal, such as one described herein. In some embodiments, the ORF comprises a nucleotide sequence encoding a site-directed endonuclease, such as a SpCas9 polypeptide and at least one NLS that is a nucleoplasmin and/or SV40 NLS. In some embodiments, the ORF comprises a nucleotide sequence encoding an N-terminal and/or C-terminal NLS operably-linked to a site-directed endonuclease, such as a SpCas9 polypeptide. In some embodiments the ORF comprises a nucleotide sequence encoding an N-terminal SV40 NLS operably-linked to a site-directed endonuclease, such as a SpCas9 polypeptide, and a C-terminal nucleoplasmin NLS operably-linked to the site-directed endonuclease, such as the SpCas9 polypeptide. In some embodiments, the nucleoplasmin NLS comprises the amino acid sequence of SEQ ID NO: 7. In some embodiments, the SV40 NLS comprises the amino acid sequence of SEQ ID NO: 8. In some embodiments, the site-directed endonuclease comprises the amino acid sequence of SEQ ID NO: 6.

In some embodiments, the disclosure provides an mRNA comprising (i) a 5' UTR; (ii) an open reading frame (ORF) comprising a nucleotide sequence that encodes a site-directed endonuclease, such as a SpCas9 polypeptide, wherein the nucleotide sequence is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 4; and (iii) a 3' UTR.

In some embodiments, the disclosure provides an mRNA comprising (i) a 5' UTR; (ii) an open reading frame (ORF) comprising a nucleotide sequence that encodes a site-directed endonuclease, such as a SpCas9 polypeptide, wherein the nucleotide sequence is set forth by SEQ ID NO: 4; and (iii) a 3' UTR.

In some embodiments, the 5' UTR of any of the foregoing mRNA is a 5' UTR described herein. In some embodiments, the 3' UTR of any of the foregoing mRNA is a 3' UTR described herein.

In some embodiments, the disclosure provides an mRNA comprising (i) a 5' UTR, wherein the 5' UTR comprises the nucleotide sequence of SEQ ID NO: 10; (ii) an open reading frame (ORF) comprising a nucleotide sequence that encodes a site-directed endonuclease, such as a SpCas9 polypeptide, wherein the nucleotide sequence is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 4; and (iii) a 3' UTR, wherein the 3' UTR comprises the nucleotide sequence of SEQ ID NO: 12.

In some embodiments, the disclosure provides an mRNA comprising (i) a 5' UTR, wherein the 5' UTR comprises the nucleotide sequence of SEQ ID NO: 10; (ii) an open reading frame (ORF) comprising a nucleotide sequence that encodes a site-directed endonuclease, such as a SpCas9 polypeptide, wherein the nucleotide sequence is set forth by the nucleotide sequence of SEQ ID NO: 4; and (iii) a 3' UTR, wherein the 3' UTR comprises the nucleotide sequence of SEQ ID NO: 12.

In some embodiments, the disclosure provides an mRNA comprising (i) a 5' UTR, wherein the 5' UTR comprises the nucleotide sequence of SEQ ID NO: 15; (ii) an open reading frame (ORF) comprising a nucleotide sequence that encodes a site-directed endonuclease, such as a SpCas9 polypeptide, wherein the nucleotide sequence is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 4; and (iii) a 3' UTR, wherein the 3' UTR comprises the nucleotide sequence of SEQ ID NO: 12.

In some embodiments, the disclosure provides an mRNA comprising (i) a 5' UTR, wherein the 5' UTR comprises the nucleotide sequence of SEQ ID NO: 15; (ii) an open reading frame (ORF) comprising a nucleotide sequence that encodes a site-directed endonuclease, such as a SpCas9 polypeptide, wherein the nucleotide sequence is set forth by the nucleotide sequence of SEQ ID NO: 4; and (iii) a 3' UTR, wherein the 3' UTR comprises the nucleotide sequence of SEQ ID NO: 12.

In some embodiments, any of the foregoing mRNA further comprises a poly-A tail, such as one described herein. In some embodiments, the poly-A tail comprises the nucleotide sequence of SEQ ID NO: 13.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 2. In some embodiments, the disclosure provides an mRNA comprising a nucleotide sequence that is 100% identical to the nucleotide sequence of SEQ ID NO: 2.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of ID NO: 14. In some embodiments, the disclosure provides an mRNA comprising a nucleotide sequence that is 100% identical to the nucleotide sequence of SEQ ID NO: 14.

In some embodiments, any of the foregoing mRNA comprise at least one chemically modified nucleoside. In some embodiments, the chemically modified nucleoside is selected from pseudouridine, N1-methylpseudouridine, and 5-methoxyuridine. In some embodiments, the chemically modified nucleoside is N1-methylpseudouridine. In some embodiments, at least about 80% or more (e.g., about 85%, 90%, 91%, 92%, 93%, 94%, 95%, 96%, 97%, 98%, 99%) of uridines in the mRNA are modified or replaced with N1-methylpseudouridine. In some embodiments, 100% of the uridines in the mRNA are modified or replaced with N1-methylpseudouridine.

In some embodiments, the disclosure provides an mRNA comprising (i) a 5' UTR, wherein the 5' UTR comprises the nucleotide sequence of SEQ ID NO: 10; (ii) an open reading frame (ORF) comprising a nucleotide sequence that encodes a site-directed endonuclease, such as a SpCas9 polypeptide, wherein the nucleotide sequence is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 4; and (iii) a 3' UTR, wherein the 3' UTR comprises the nucleotide sequence of SEQ ID NO: 12, wherein 100% of the uridines of the mRNA are modified or replaced with N1-methylpseudouridine.

In some embodiments, the disclosure provides an mRNA comprising (i) a 5' UTR, wherein the 5' UTR comprises the nucleotide sequence of SEQ ID NO: 10; (ii) an open reading frame (ORF) comprising a nucleotide sequence that encodes a site-directed endonuclease, such as a SpCas9 polypeptide, wherein the nucleotide sequence is set forth by the nucleotide sequence of SEQ ID NO: 4; and (iii) a 3' UTR, wherein the 3' UTR comprises the nucleotide sequence of SEQ ID NO: 12, wherein 100% of the uridines of the mRNA are modified or replaced with N1-methylpseudouridine.

In some embodiments, the disclosure provides an mRNA comprising (i) a 5' UTR, wherein the 5' UTR comprises the nucleotide sequence of SEQ ID NO: 15; (ii) an open reading frame (ORF) comprising a nucleotide sequence that encodes a site-directed endonuclease, such as a SpCas9 polypeptide, wherein the nucleotide sequence is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 4; and (iii) a 3' UTR, wherein the 3' UTR comprises the nucleotide sequence of SEQ ID NO: 12, wherein 100% of the uridines of the mRNA are modified or replaced with N1-methylpseudouridine.

In some embodiments, the disclosure provides an mRNA comprising (i) a 5' UTR, wherein the 5' UTR comprises the nucleotide sequence of SEQ ID NO: 15; (ii) an open reading frame (ORF) comprising a nucleotide sequence that encodes a site-directed endonuclease, such as a SpCas9 polypeptide, wherein the nucleotide sequence is set forth by the nucleotide sequence of SEQ ID NO: 4; and (iii) a 3' UTR, wherein the 3' UTR comprises the nucleotide sequence of SEQ ID NO: 12, wherein 100% of the uridines of the mRNA are modified or replaced with N1-methylpseudouridine.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 2, wherein 100% of the uridines of the mRNA are modified or replaced with N1-methylpseudouridine.

In some embodiments, the disclosure provides an mRNA comprising a nucleotide sequence that is 100% identical to the nucleotide sequence of SEQ ID NO: 2, wherein 100% of the uridines of the mRNA are modified or replaced with N1-methylpseudouridine.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of ID NO: 14, wherein 100% of the uridines of the mRNA are modified or replaced with N1-methylpseudouridine.

In some embodiments, the disclosure provides an mRNA comprising a nucleotide sequence that is 100% identical to the nucleotide sequence of SEQ ID NO: 14, wherein 100% of the uridines of the mRNA are modified or replaced with N1-methylpseudouridine.

In some embodiments, any of the foregoing mRNA further comprises a 5' cap, such as one described herein. In some embodiments, the 5' cap is a cap-0, a cap-1, or a cap-2 structure.

Systems for Genome Editing

Engineered versions of CRISPR/Cas systems has been developed in numerous formats to mutate or edit genomic DNA of cells from other species. The general approach of using the CRISPR/Cas system involves the heterologous expression or introduction of a site-directed nuclease (e.g., Cas nuclease) in combination with a guide RNA (gRNA) into a cell, resulting in a DNA cleavage event (e.g., the formation a double-strand break (DSB)) in the backbone of the cell's genomic DNA at a precise, targetable location. The manner in which the DNA cleavage event is repaired by the cell provides the opportunity to edit the genome by the addition, removal, or modification (substitution) of DNA nucleotide(s) or sequences (e.g. genes).

Site-directed polypeptides can introduce DSBs in nucleic acids, e.g., genomic DNA. The DSB can stimulate a cell's endogenous DNA-repair pathways. Non-homologous end joining (NHEJ) can repair a DSB without the need for a homologous template. This can result in small deletions or insertions (indels) in the target nucleic acid at the site of cleavage, and can lead to disruption or alteration of gene expression. Homology-dependent repair (HDR) can occur when a homologous repair template, or exogenous donor template, is available. The homologous donor template comprises sequences that are homologous to sequences flanking the target nucleic acid cleavage site. For the purposes of genome editing, the repair template can be supplied as an exogenous nucleic acid. An exogenous nucleic acid is termed a donor polynucleotide (or donor template, or donor, or donor sequence) herein. With donor polynucleotides, an additional nucleic acid sequence (such as a transgene) or modification (such as a single or multiple base change or a deletion) can be introduced at the cleavage site so that the additional or altered nucleic acid sequence also becomes incorporated into the target locus.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. Mutations contemplated include substitutions, additions, and deletions, or any combination thereof. The processes of deleting genomic DNA and integrating non-native nucleic acid into genomic DNA are examples of genome editing.

I. Guide RNAs

In some embodiments, the disclosure provides a system for genome editing comprising at least one guide RNA (gRNA) molecule, which interacts with a site-directed endonuclease, such as a Cas nuclease (e.g., a SpCas9 polypeptide) to form a gRNA/Cas nuclease complex. A gRNA comprises at least a user-defined targeting domain termed a "spacer" comprising a nucleotide sequence and a CRISPR repeat sequence. In engineered CRISPR/Cas systems, a gRNA/Cas nuclease complex is targeted to a specific target sequence of interest within a target nucleic acid (e.g. a genomic DNA molecule) by generating a gRNA comprising a spacer with a nucleotide sequence that is able to bind to the specific target sequence in a complementary fashion (See Jinek et al., Science, 337, 816-821 (2012) and Deltcheva et al., Nature, 471, 602-607 (2011)). Thus, the spacer provides the targeting function of the gRNA/Cas nuclease complex.

In naturally-occurring type II-CRISPR/Cas systems, the "gRNA" is comprised of two RNA strands: 1) a CRISPR RNA (crRNA) comprising the spacer and CRISPR repeat sequence, and 2) a trans-activating CRISPR RNA (tracrRNA). In Type II-CRISPR/Cas systems, the portion of the crRNA comprising the CRISPR repeat sequence and a portion of the tracrRNA hybridize to form a crRNA: tracrRNA duplex, which interacts with a Cas nuclease (e.g., Cas9). As used herein, the terms "split gRNA" or "modular gRNA" refer to a gRNA molecule comprising two RNA strands, wherein the first RNA strand incorporates the crRNA function(s) and/or structure and the second RNA strand incorporates the tracrRNA function(s) and/or structure, and wherein the first and second RNA strands partially hybridize.

Accordingly, in some embodiments, a gRNA provided by the disclosure comprises two RNA molecules. In some embodiments, the gRNA comprises a CRISPR RNA (crRNA) and a trans-activating CRISPR RNA (tracrRNA). In some embodiments, the gRNA is a split gRNA. In some embodiments, the gRNA is a modular gRNA. In some embodiments, the split gRNA comprises a first strand comprising, from 5' to 3', a spacer, and a first region of complementarity; and a second strand comprising, from 5' to 3', a second region of complementarity; and optionally a tail domain.

In some embodiments, the crRNA comprises a spacer comprising a nucleotide sequence that is complementary to and hybridizes with a sequence that is complementary to the target sequence on a target nucleic acid (e.g., a genomic DNA molecule). In some embodiments, the crRNA comprises a region that is complementary to and hybridizes with a portion of the tracrRNA.

In some embodiments, the tracrRNA may comprise all or a portion of a wild-type tracrRNA sequence (e.g., a tracrRNA from *S. pyogenes*). In some embodiments, the tracrRNA may comprise a truncated or modified variant of the wild-type tracr RNA. In some embodiments, the tracrRNA may comprise 5, 6, 7, 8, 9, 10, 11, 12, 13, 14, 15, 16, 17, 18, 19, 20, 25, 30, 40, 50, 60, 70, 80, 90, 100, or more than 100 nucleotides in length. In certain embodiments, the tracrRNA is at least 26 nucleotides in length. In additional embodiments, the tracrRNA is at least 40 nucleotides in length. In some embodiments, the tracrRNA comprises certain secondary structures, such as, e.g., one or more hairpins or stem-loop structures, or one or more bulge structures.

A. Single Guide RNAs

Engineered CRISPR/Cas nuclease systems often combine a crRNA and a tracrRNA into a single RNA molecule, referred to herein as a "single guide RNA" (sgRNA), by adding a linker between these components. Without being bound by theory, similar to a duplexed crRNA and tracrRNA, an sgRNA will form a complex with a Cas nuclease (e.g., SpCas9), guide the Cas nuclease to a target sequence and activate the Cas nuclease for cleavage the target nucleic acid (e.g., genomic DNA). Accordingly, in some embodiments, the gRNA comprises a crRNA and a tracrRNA that are operably linked. In some embodiments, the sgRNA comprises a crRNA covalently linked to a tracrRNA. In some embodiments, the crRNA and the tracrRNA is covalently linked via a linker. In some embodiments, the sgRNA comprises a stem-loop structure via base pairing between the crRNA and the tracrRNA. In some embodiments, a sgRNA comprises, from 5' to 3', a spacer, a first region of complementarity, a linking domain, a second region of complementarity, and, optionally, a tail domain.

B. Spacer Sequences

In some embodiments, the gRNAs of the disclosure comprise a spacer sequence. A spacer sequence is a sequence that defines the target site of a target nucleic acid (e.g., genomic DNA). The spacer sequence hybridizes to a target sequence in a target nucleic acid of interest. The spacer interacts with the target nucleic acid in a sequence-specific manner via hybridization (i.e., base pairing). The nucleotide sequence of the spacer can vary depending on the sequence of the target nucleic acid of interest. The spacer sequence is also referred to as the DNA-targeting segment.

The target nucleic acid is a double-stranded molecule: one strand comprises the target sequence adjacent to a PAM sequence and is referred to as the "PAM strand," and the second strand is referred to as the "non-PAM strand" and is complementary to the PAM strand and target sequence. Both gRNA spacer and the target sequence are complementary to the non-PAM strand of the target nucleic acid. The gRNA spacer sequence hybridizes to the complementary strand (i.e., the non-PAM strand of the target nucleic acid/target site). In some embodiments, the spacer is sufficiently complementary to the complementary strand of the target sequence (i.e., non-PAM strand), as to target a site-directed endonuclease, such as a Cas nuclease (e.g., a SpCas9 polypeptide) to the target nucleic acid/target site.

In some embodiments, the spacer is at least 80%, 85%, 90% or 95% complementary to the non-PAM strand of the target nucleic acid. In some embodiments, the spacer is 100% complementary to the non-PAM strand of the target nucleic acid.

In some embodiments, the 5' most nucleotide of gRNA comprises the 5' most nucleotide of the spacer. In some embodiments, the spacer is located at the 5' end of the crRNA. In some embodiments, the spacer is located at the 5' end of the sgRNA. In some embodiments, the spacer is about 15-50, about 20-45, about 25-40 or about 30-35 nucleotides in length. In some embodiments, the spacer is about 19-22 nucleotides in length. In some embodiments the spacer is about 15, 16, 17, 18, 19, 20, 21, 22, 23, 24, 25, 26, 27, 28, 29 or 30 nucleotides in length. In some embodiments the spacer is 19 nucleotides in length. In some embodiments, the spacer is 20 nucleotides in length, in some embodiments, the spacer is 21 nucleotides in length.

In some embodiments, the nucleotide sequence of the target sequence and the PAM comprises the formula 5' $N_{19-21}$-N-R-G-3', wherein N is any nucleotide, and wherein R is a nucleotide comprising the nucleobase adenine (A) or guanine (G), and wherein the three 3' terminal nucleic acids, N-R-G represent the *S. pyogenes* PAM. In some embodiments, the nucleotide sequence of the spacer is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, and/or presence of SNPs.

In some embodiments, the spacer can include at least one or more modified nucleotide(s) such as those described herein. The disclosure provides gRNA molecules comprising a spacer which may comprise the nucleobase uracil (U), while any DNA encoding a gRNA comprising a spacer comprising the nucleobase uracil (U) will comprise the nucleobase thymine (T) in the corresponding position(s).

II. Donor Polynucleotides

The disclosure provides donor polynucleotides that, upon insertion into a DSB, correct or induce a mutation in a target nucleic acid (e.g., a genomic DNA). In some embodiments, the donor polynucleotides provided by the disclosure are recognized and used by the HDR machinery of a cell to repair a double strand break (DSB) introduced into a target nucleic acid by a site-directed nuclease, wherein repair of the DSB results in the insertion of the donor polynucleotide into the target nucleic acid. Alternatively, a donor polynucleotide may have no regions of homology to the targeted location in the DNA and may be integrated by NHEJ-dependent end joining following cleavage at the target site.

A donor polynucleotide or template can be single-stranded and/or double-stranded DNA, and can be introduced into a cell in linear or circular form. In some embodiments, the donor polynucleotide can be a double-stranded oligonucleotide (dsODNs) or a single-stranded oligonucleotide (ssODN). If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

A donor template, in some embodiments, is inserted so that its expression is driven by the endogenous promoter at the integration site, namely the promoter that drives expression of the endogenous gene into which the donor is inserted. However, in some embodiments, the donor template comprises an exogenous promoter and/or enhancer, for example a constitutive promoter, an inducible promoter, or tissue-specific promoter.

Furthermore, exogenous sequences may also include transcriptional or translational regulatory sequences, for example, promoters, enhancers, insulators, internal ribosome entry sites, sequences encoding 2A peptides and/or polyadenylation signals.

In some embodiments, the donor polynucleotides comprise a nucleotide sequence which corrects or induces a mutation in a genomic DNA (gDNA) molecule in a cell, wherein when the donor polynucleotide is introduced into the cell in combination with a site-directed nuclease, a HDR or NHEJ DNA repair pathway inserts the donor polynucleotide into a double-stranded DNA break (DSB) introduced into the gDNA by the Cas9 nuclease (e.g., SpCas9 polypeptide) at a location proximal to the mutation, thereby correcting the mutation.

In some embodiments, the donor polynucleotide comprises a nucleotide sequence which corrects or induces a mutation, wherein the nucleotide sequence that corrects or induces a mutation comprises a single or multiple nucleotide(s). In some embodiments, the nucleotide sequence which corrects or induces a mutation comprises one or more codon(s). In some embodiments, the nucleotide sequence which corrects or induces a mutation comprises an exonic and/or intronic sequence.

In some embodiments, repair of the target nucleic acid molecule with the donor polynucleotide results in an insertion, deletion, or substitution of one or more nucleotides of the target nucleic acid molecule. In some embodiments, the insertion, deletion, or substitution of one or more nucleotides results in one or more amino acid changes in a protein expressed from a gene comprising the target sequence. In some embodiments, the insertion, deletion, or substitution of one or more nucleotides results in one or more nucleotide changes in an RNA expressed from the target gene. In some embodiments, the insertion, deletion, or substitution of one or more nucleotides alters the expression level of the target gene. In some embodiments, the insertion, deletion, or substitution of one or more nucleotides results in increased or decreased expression of the target gene. In some embodiments, the insertion, deletion, or substitution of one or more nucleotides results in gene knockdown. In some embodiments, the insertion, deletion, or substitution of one or more nucleotides results in gene knockout. In some embodiments, the repair of the target nucleic acid molecule with the donor polynucleotide results in replacement of an exon sequence, an intron sequence, a transcriptional control sequence, a translational control sequence, a sequence comprising a splicing signal, or a non-coding sequence of the target gene.

The donor polynucleotide is of a suitable length to correct or induce a mutation in a gDNA. In some embodiments, the donor polynucleotide comprises 10, 15, 20, 25, 50, 75, 100, 150, 200, 250, 300, 400, 500, or more nucleotides in length. In some embodiments, the donor polynucleotide is about 10-100, about 10-300, about 20-80, about 30-70, or about 40-60 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length. In some embodiments, the donor polynucleotide is about 10-200 nucleotides in length. In some embodiments, the donor polynucleotide is about 10-500 nucleotides in length.

In some embodiments, for example those described herein wherein a donor polynucleotide is incorporated into the cleaved target site by a NHEJ DNA repair pathway, the donor polynucleotide has no homology arms. In some embodiments, for example those described herein wherein a donor polynucleotide is incorporated into the cleaved target site by an HDR DNA repair pathway, the donor polynucleotide has a left homology arm, a right homology arm, or both. In some embodiments, the left homology arm, the right homology arm, or both are of sufficient length (e.g., 100-1000s nucleotides in length) to facilitate insertion of the exogenous nucleotide sequence by an HDR DNA repair pathway.

The donor polynucleotides provided by the disclosure are produced by suitable nucleic acid synthesis method or means known in the art, such as those described in more detail below. DNA synthesis is the natural or artificial creation of deoxyribonucleic acid (DNA) molecules. The term DNA synthesis refers to DNA replication, DNA biosynthesis (e.g., in vivo DNA amplification), enzymatic DNA synthesis (e.g., polymerase chain reaction (PCR); in vitro DNA amplification) or chemical DNA synthesis.

In some embodiments, each strand of the donor polynucleotide is produced by oligonucleotide synthesis. Oligonucleotide synthesis is the chemical synthesis of relatively short fragments or strands of single-stranded nucleic acids with a defined chemical structure (sequence). Methods of oligonucleotide synthesis are known in the art (see e.g., Reese (2005) Organic & Biomolecular Chemistry 3(21): 3851). The two strands can then be annealed together or duplexed to form a donor polynucleotide.

In some embodiments, donor polynucleotides are provided with chemistries suitable for delivery and stability within cells. Furthermore, in some embodiments, chemistries are provided that are useful for controlling the pharmacokinetics, biodistribution, bioavailability and/or efficacy of the donor polynucleotides described herein. Accordingly, in some embodiments, donor polynucleotides described herein may be modified, e.g., comprise a modified sugar moiety, a modified internucleoside linkage, a modified nucleoside, a modified nucleotide, and/or combinations thereof. In addition, the modified donor polynucleotides may exhibit one or more of the following properties: are not immune stimulatory; are nuclease resistant; have improved cell uptake compared to unmodified donor polynucleotides; and/or are not toxic to cells or mammals Nucleotide and nucleoside modifications have been shown to make a polynucleotide (e.g., a donor polynucleotide) into which they are incorporated more resistant to nuclease digestion than the native polynucleotide and these modified polynucleotides have been shown to survive intact for a longer time than unmodified polynucleotides. Specific examples of modified oligonucleotides include those comprising modified backbones (i.e. modified internucleoside linkage), for example, phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see e.g., De Mesmaeker et al., Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the polynucleotide is replaced with a polyamide backbone, the nucleotides being bound directly or indirectly to the aza nitrogen atoms of the polyamide backbone, see Nielsen et at, Science 1991, 254, 1497). Phosphorus-containing modified linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Cyclohexenyl nucleic acid oligonucleotide mimetics are described in Wang et al., J. Am. Chem. Soc, 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In some embodiments, the donor polynucleotides of the disclosure are stabilized against nucleolytic degradation such as by the incorporation of a modification (e.g., a nucleotide modification). In some embodiments, donor polynucleotides of the disclosure include a phosphorothioate at least the first, second, and/or third internucleotide linkage at the 5' and/or 3' end of the nucleotide sequence. In some embodiments, donor polynucleotides of the disclosure include one or more 2'-modified nucleotides, e.g., 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). In some embodiments, donor polynucleotides of the disclosure include a phosphorothioate and a 2'-modified nucleotide as described herein.

Any of the modified chemistries described herein can be combined with each other, and that one, two, three, four, five, or more different types of modifications can be included within the same molecule. In some embodiments, the donor polynucleotide comprises 1, 2, 3, 4, 5, 6, 7, 8, 9, 10 or modifications.

In some aspects, the insertion of a donor polynucleotide into a DSB is determined by a suitable method known in the art. For example, after the insertional event, the nucleotide sequence of PCR amplicons generated using PCR primer that flank the DSB site is analyzed for the presence of the nucleotide sequence comprising the donor polynucleotide. Next-generation sequencing (NGS) techniques are used to determine the extent of donor polynucleotide insertion into a DSB analyzing PCR amplicons for the presence or absence of the donor polynucleotide sequence. Further, since each donor polynucleotide is a linear, dsDNA molecule, which can insert in either of two orientations, NGS analysis can be used to determine the extent of insertion of the donor polynucleotide in either direction.

In some aspects, the insertion of the donor polynucleotide and its ability to correct a mutation is determined by nucleotide sequence analysis of mRNA transcribed from the gDNA into which the donor polynucleotide is inserted. An mRNA transcribed from gDNA containing an inserted donor polynucleotide is analyzed by a suitable method known in the art. For example, conversion of mRNA extracted from cells treated or contacted with a donor polynucleotide or system provided by the disclosure is enzymatically converted into cDNA, which is further by analyzed by NGS analysis to determine the extent of mRNA molecule comprising the corrected mutation.

In other aspects, the insertion of a donor polynucleotide and its ability to correct a mutation is determined by protein sequence analysis of a polypeptide translated from an mRNA transcribed from the gDNA into which the donor polynucleotide is inserted. In some embodiments, a donor polynucleotide corrects or induces a mutation by the incorporation of a codon into an exon that makes an amino acid change in a gene comprising a gDNA molecule, wherein translation of an mRNA from the gene containing the inserted donor polynucleotide generates a polypeptide comprising the amino acid change. The amino acid change in the polypeptide is determined by protein sequence analysis using techniques including, but not limited to, Sanger sequencing, mass spectrometry, functional assays that measure an enzymatic activity of the polypeptide, or immunoblotting using an antibody reactive to the amino acid change.

III. Target Sites

In some embodiments, the Cas nucleases (e.g., SpCas9 polypeptide) described herein are directed to and cleave (e.g., introduce a DSB) in a target nucleic acid molecule (e.g., genomic DNA). In some embodiments, a Cas nuclease (e.g., SpCas9 polypeptide) is directed by a gRNA to a target site of a target nucleic acid molecule (e.g., gDNA), where the guide RNA hybridizes with the complementary strand of the target sequence and the Cas nuclease cleaves the target nucleic acid at the target site. In some embodiments, the complementary strand of the target sequence is fully or partially complementary to the targeting sequence (e.g., spacer sequence) of the guide RNA.

In some embodiments, the target sequence comprises 18-24 nucleotides in length. In some embodiments, the target sequence comprises 19-21 nucleotides in length. In some embodiments, the target sequence comprises 20 nucleotides in length.

The target nucleic acid molecule is any DNA molecule that is endogenous or exogenous to a cell. As used herein, the term "endogenous sequence" refers to a sequence that is native to the cell. In some embodiments, the target nucleic acid molecule is a genomic DNA (gDNA) molecule or a chromosome from a cell or in the cell. In some embodiments, the target sequence of the target nucleic acid molecule is a genomic sequence from a cell or in the cell. In other embodiments, the cell is a eukaryotic cell. In some embodiments, the eukaryotic cell is a mammalian cell. In some embodiments, the eukaryotic cell is a rodent cell. In some embodiments, the eukaryotic cell is a non-human primate cell. In some embodiments, the eukaryotic cell is a human cell. In some embodiments, the target sequence is a viral sequence. In some embodiments, the target sequence is a synthesized sequence. In some embodiments, the target sequence is on a eukaryotic chromosome, such as a human chromosome.

In some embodiments, the target sequence is located in a coding sequence of a gene, an intron sequence of a gene, a transcriptional control sequence of a gene, a translational control sequence of a gene, or a non-coding sequence between genes. In some embodiments, the gene is a protein coding gene. In other embodiments, the gene is a non-coding RNA gene. In some embodiments, the target sequence comprises all or a portion of a disease-associated gene. In some embodiments, the target sequence is located in a human gene selected from: transferrin (TF), albumin (ALB), serpin family A member 1 (SERPINA1), glucose-6-phosphatase catalytic subunit (G6PC), proprotein convertase subtilisin/kexin type 9 (PCSK9), alanine glyoxylate aminotransferase (AGXT), rhodopsin (RHO), guanylate cyclase 2D (GUCY2D), usherin (USH2A), and recombination activating 1 (RAG1).

In some embodiments, the target sequence is located in a non-genic functional site in the genome that controls aspects of chromatin organization, such as a scaffold site or locus control region. In some embodiments, the target sequence is a genetic safe harbor site, i.e., a locus that facilitates safe genetic modification.

In some embodiments, the target sequence is adjacent to a protospacer adjacent motif (PAM), a short sequence recognized by a CRISPR/Cas9 complex. In the PAM sequence comprises NGG (wherein N is defined as any nucleotide). In some embodiments, the PAM sequence is NGG.

IV. Vectors

In some embodiments, the donor polynucleotide is provided by a vector. In some embodiments, the vector may be a DNA vector. In some embodiments, the vector may be circular. In other embodiments, the vector may be linear. Non-limiting exemplary vectors include plasmids, phagemids, cosmids, artificial chromosomes, minichromosomes, transposons, viral vectors, and expression vectors.

In some embodiments, the vector is a recombinant adeno-associated virus (AAV) vector. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 1.

TABLE 1

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

In some embodiments, the method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

AAV vector serotypes can be matched to target cell types. For example, the following exemplary cell types can be transduced by the indicated AAV serotypes among others. See Table 2.

TABLE 2

| Tissue/Cell Type | Serotype |
| --- | --- |
| Liver | AAV3, AAV5, AAV8, AAV9 |
| Skeletal muscle | AAV1, AAV7, AAV6, AAV8, AAV9 |
| Central nervous system | AAV5, AAV1, AAV4, AAV8, AAV9 |
| RPE | AAV5, AAV4, AAV2, AAV8, AAV9, AAVrh8R |
| Photoreceptor cells | AAV5, AAV8, AAV9, AAVrh8R |
| Lung | AAV9, AAV5 |
| Heart | AAV8 |
| Pancreas | AAV8 |
| Kidney | AAV2, AAV8 |

In addition to adeno-associated viral vectors, other viral vectors can be used. Such viral vectors include, but are not limited to, adenovirus, lentivirus, alphavirus, enterovirus, pestivirus, baculovirus, herpesvirus, Epstein Barr virus, papovavirus, poxvirus, vaccinia virus, and herpes simplex virus.

Nucleic Acid Modifications

In some embodiments, a nucleic acid of the disclosure (e.g., gRNA and/or mRNA) comprises one or more modified nucleobases, nucleosides, nucleotides or internucleoside linkages. In some embodiments, modified nucleic acids disclosure (e.g., gRNA and/or mRNA) have useful properties, including enhanced stability, intracellular retention, enhanced translation, and/or the lack of a substantial induction of the innate immune response of a cell into which the nucleic acid is introduced, as compared to a reference unmodified nucleic acid. Therefore, use of modified nucleic acids (e.g., gRNA and/or mRNA) may enhance the efficiency of protein production (e.g., SpCas9 expression from an mRNA of the disclosure), intracellular retention of the nucleic acids, efficiency of a genome editing system comprising the nucleic acid, as well as possess reduced immunogenicity.

In some embodiments, a gRNA and/or mRNA of the disclosure comprises one or more (e.g., 1, 2, 3, 4, 5, 6, 7, 8, 9, 10, 20, 30, 40, 50, 60, 70, 80, 90, 100, or more) different modified nucleobases, nucleosides, nucleotides or internucleoside linkages. In some embodiments, the modified nucleic acid (e.g., gRNA, and/or mRNA) has reduced degradation in a cell into which the nucleic acid is introduced, relative to a corresponding unmodified nucleic acid.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine (mcm⁵U), 5-methoxycarbonylmethyl-2-thio-uridine (mcm⁵s²U), 5-aminomethyl-2-thio-uridine (nm⁵s²U), 5-methylaminomethyl-uridine (mnm⁵U), 5-methylaminomethyl-2-thio-uridine (mnm⁵s²U), 5-methylaminomethyl-2-seleno-uridine (mnm⁵se²U), 5-carbamoylmethyl-uridine (ncm⁵U), 5-carboxymethylaminomethyl-uridine (cmnm⁵U), 5-carboxymethylaminomethyl-2-thio-uridine (cmnm⁵s²U), 5-propynyl-uridine, 1-propynyl-pseudouridine, 5-taurinomethyl-uridine (τm⁵U), 1-taurinomethyl-pseudouridine, 5-taurinomethyl-2-thio-uridine(τm⁵s²U), 1-taurinomethyl-4-thio-pseudouridine, 5-methyl-uridine (m⁵U, i.e., having the nucleobase deoxythymine), 1-methyl-pseudouridine (m¹ψ), 5-methyl-2-thio-uridine (m⁵s²U), 1-methyl-4-thio-pseudouridine (m¹s⁴ψ), 4-thio-1-methyl-pseudouridine, 3-methyl-pseudouridine (m³ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m⁵D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp³U), 1-methyl-3-(3-amino-3-carboxypropyl)pseudouridine (acp³ ψ), 5-(isopentenylaminomethyl)uridine (inm⁵U), 5-(isopentenylaminomethyl)-2-thio-uridine (inm⁵s²U), α-thio-uridine, 2'-O-methyl-uridine (Um), 5,2'-O-dimethyl-uridine (m⁵Um), 2'-O-methyl-pseudouridine (ψm), 2-thio-2'-O-methyl-uridine (s²Um), 5-methoxycarbonylmethyl-2'-O-methyl-uridine (mcm⁵Um), 5-carbamoylmethyl-2'-O-methyl-uridine (ncm⁵Um), 5-carboxymethylaminomethyl-2'-O-methyl-uridine (cmnm⁵Um), 3,2'-O-dimethyl-uridine (m³Um), and 5-(isopentenylaminomethyl)-2'-O-methyl-uridine (inm⁵Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m³C), N4-acetyl-cytidine (ac⁴C), 5-formyl-cytidine (f⁵C), N4-methyl-cytidine (m⁴C), 5-methyl-cytidine (m⁵C), 5-halo-cytidine (e.g., 5-iodo-cytidine), 5-hydroxymethyl-cytidine (hm⁵C), 1-methyl-pseudoisocytidine, pyrrolo-cytidine, pyrrolo-pseudoisocytidine, 2-thio-cytidine (s²C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k₂C), α-thio-cytidine, 2'-O-methyl-cytidine (Cm), 5,2'-O-dimethyl-cytidine (m⁵Cm), N4-acetyl-2'-O-methyl-cytidine (ac⁴Cm), N4,2'-O-dimethyl-cytidine (m⁴Cm), 5-formyl-2'-O-methyl-cytidine (f⁵Cm), N4,N4,2'-O-trimethyl-cytidine (m⁴₂Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m¹A), 2-methyl-adenine (m²A), N6-methyl-adenosine (m⁶A), 2-methylthio-N6-methyl-adenosine (ms²m⁶A), N6-isopentenyl-adenosine (i⁶A), 2-methylthio-N6-isopentenyl-adenosine (ms²i⁶A), N6-(cis-hydroxyisopentenyl)adenosine (io⁶A), 2-methylthio-N6-(cis-hydroxyisopentenyl)adenosine (ms²io⁶A), N6-glycinylcarbamoyl-adenosine (g⁶A), N6-threonylcarbamoyl-adenosine (t⁶A), N6-methyl-N6-threonylcarbamoyl-adenosine (m⁶t⁶A), 2-methylthio-N6-threonylcarbamoyl-adenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms²hn⁶A), N6-acetyl-adenosine (ac⁶A), 7-methyl-adenine, 2-methylthio-adenine, 2-methoxy-adenine, α-thio-adenosine, 2'-O-methyl-adenosine (Am), N6,2'-O-dimethyl-adenosine (m⁶Am), N6,N6,2'-O-trimethyl-adenosine (m⁶₂Am), 1,2'-O-dimethyl-adenosine (m¹Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-aminopentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine (m¹), wyosine (imG), methylwyosine (mimG), 4-demethyl-wyosine (imG-14), isowyosine (imG2), wybutosine (yW), peroxywybutosine (o₂yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ₀), 7-aminomethyl-7-deaza-guanosine (preQ₁), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m¹G), N2-methyl-guanosine (m²G), N2,N2-dimethyl-guanosine (m²₂G), N2,7-dimethyl-guanosine (m²,⁷G), N2, N2,7-dimethyl-guanosine (m²,²,⁷G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m¹Gm), N2,7-dimethyl-2'-O-methyl-guanosine (m²,⁷Gm), 2'-O-methyl-inosine (Im), 1,2'-O-dimethyl-inosine (m¹Im), 2'-O-ribosylguanosine (phosphate) (Gr(p)) , 1-thio-guanosine, O6-methyl-guanosine, 2'-F-ara-guanosine, and 2'-F-guanosine.

In some embodiments, a nucleic acid (e.g., mRNA and/or gRNA) of the disclosure includes a combination of one or more of the aforementioned modified nucleobases (e.g., a combination of 2, 3 or 4 of the aforementioned modified nucleobases).

In some embodiments, the modified nucleobase is pseudouridine (ψ), N1-methylpseudouridine (m¹ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine , 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, a nucleic acid (e.g., mRNA and/or gRNA) of the disclosure includes a combination of one or more of the aforementioned modified nucleobases (e.g., a combination of 2, 3 or 4 of the aforementioned modified nucleobases).

In some embodiments, the modified nucleobase is a modified cytosine. Exemplary nucleobases and nucleosides having a modified cytosine include N4-acetyl-cytidine ($ac^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, 2-thio-cytidine ($s^2C$), 2-thio-5-methyl-cytidine. In some embodiments, a nucleic acid (e.g., mRNA and/or gRNA) of the disclosure includes a combination of one or more of the aforementioned modified nucleobases (e.g., a combination of 2, 3 or 4 of the aforementioned modified nucleobases).

In some embodiments, the modified nucleobase is a modified adenine. Exemplary nucleobases and nucleosides having a modified adenine include 7-deaza-adenine, 1-methyl-adenosine ($m^1A$), 2-methyl-adenine ($m^2A$), N6-methyl-adenosine ($m^6A$). In some embodiments, a nucleic acid (e.g., mRNA and/or gRNA) of the disclosure includes a combination of one or more of the aforementioned modified nucleobases (e.g., a combination of 2, 3 or 4 of the aforementioned modified nucleobases).

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 7-deaza-guanosine, 7-cyano-7-deaza-guanosine ($preQ_0$), 7-aminomethyl-7-deaza-guanosine ($preQ_1$), 7-methyl-guanosine ($m^7G$), 1-methyl-guanosine ($m^1G$), 8-oxo-guanosine, 7-methyl-8-oxo-guanosine. In some embodiments, a nucleic acid (e.g., mRNA and/or gRNA) of the disclosure includes a combination of one or more of the aforementioned modified nucleobases (e.g., a combination of 2, 3 or 4 of the aforementioned modified nucleobases).

In some embodiments, the modified nucleobase is 1-methyl-pseudouridine ($m^1\psi$), 5-methoxy-uridine ($mo^5U$), 5-methyl-cytidine ($m^5C$), pseudouridine ($\psi$), α-thio-guanosine, or α-thio-adenosine. In some embodiments, a nucleic acid (e.g., mRNA and/or gRNA) of the disclosure includes a combination of one or more of the aforementioned modified nucleobases (e.g., a combination of 2, 3 or 4 of the aforementioned modified nucleobases).

In certain embodiments, a nucleic acid (e.g., mRNA and/or gRNA) of the disclosure is uniformly modified (i.e., fully modified, modified through-out the entire sequence) for a particular modification. For example, an mRNA can be uniformly modified with N1-methylpseudouridine ($m^1\psi$) or 5-methyl-cytidine ($m^5C$), meaning that all uridines or all cytosine nucleosides in the mRNA sequence are replaced with N1-methylpseudouridine ($m^1\psi$) or 5-methyl-cytidine ($m^5C$). Similarly, a nucleic acid (e.g., mRNA and/or gRNA) of the disclosure can be uniformly modified for any type of nucleoside residue present in the sequence by replacement with a modified residue such as those set forth above.

Methods of Making Nucleic Acids of the Disclosure

The nucleic acids (e.g., mRNA and/or gRNA) of the disclosure are produced by any suitable means available in the art, including but not limited to in vitro transcription (IVT), synthetic and/or chemical synthesis methods, or a combination thereof. Enzymatic (IVT), solid-phase, liquid-phase, combined synthetic methods, small region synthesis, and ligation methods are utilized.

In some embodiments, one or more nucleic acids (e.g., mRNA and/or gRNA) of the disclosure are synthesized by enzymatic methods (e.g., in vitro transcription, IVT). In some embodiments, one or more nucleic acids (e.g., mRNA and/or gRNA) of the disclosure are made using IVT enzymatic synthesis methods. Methods of making polynucleotides by IVT are known in the art and are described in International Application PCT/US2013/30062. Accordingly, the present disclosure also includes polynucleotides, e.g., DNA, constructs and vectors that are used to in vitro transcribe a nucleic acid described herein.

In some aspects, enzymatic or chemical ligation methods are used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

In some embodiments, one or more nucleic acids (e.g., mRNA and/or gRNA) of the disclosure are chemically synthesized by any means described in the art (see e.g., WO/2005/01248). While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together.

In some embodiments, one or more nucleic acid modifications, such as those described herein, are introduced during or after chemical synthesis and/or enzymatic generation of the nucleic acids, e.g., modifications that enhance stability, reduce the likelihood or degree of innate immune response, and/or enhance other attributes, as described in the art.

In some embodiments, non-natural modified nucleobases are introduced into a nucleic acid (e.g., mRNA and/or gRNA) of the disclosure, during synthesis or post-synthesis. In certain embodiments, modifications are on internucleoside linkages, purine or pyrimidine bases, or sugar. In particular embodiments, the modification is introduced at the terminal of a polynucleotide; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Nanoparticle Compositions

In some aspects, the disclosure provides nanoparticle compositions (e.g., lipid nanoparticles, LNPs) comprising an mRNA, one or more gRNAs, a donor polynucleotide, a system, or components of a system described herein. The mRNA, one or more gRNAs, a donor polynucleotide, a system, or components of a system may be formulated, individually or combined together, in nanoparticles or other delivery vehicles, (e.g., polymeric nanoparticles) to facilitate cellular uptake and/or to protect them from degradation when delivered to a subject (e.g., a patient with a mutation).

In some embodiments, a nanoparticle composition comprises a lipid. Lipid nanoparticles include, but are not limited to, liposomes and micelles. Any of a number of lipids may be present, including cationic and/or ionizable lipids, anionic lipids, neutral lipids, amphipathic lipids, conjugated lipids (e.g., PEGylated lipids), and/or structural lipids. Such lipids can be used alone or in combination.

Nanoparticles are ultrafine particles typically ranging between 1 and 100 to 500 nanometers (nm) in size with a surrounding interfacial layer and often exhibiting a size-related or size-dependent property. Nanoparticle compositions are myriad and encompass lipid nanoparticles (LNPs), liposomes (e.g., lipid vesicles), and lipoplexes. For example, a nanoparticle composition can be a liposome having a lipid bilayer with a diameter of 500 nm or less. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

As used herein, "size" or "mean size" in the context of nanoparticle compositions refers to the mean diameter of a nanoparticle composition.

In one embodiment, the polynucleotide encoding a polypeptide of interest are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

In some embodiments, the pKa of the nanoparticle is about 5-8. In some embodiments, the pKa of the nanoparticle is about 5. In some embodiments, the pKa of the nanoparticle is about 6. In some embodiments, the pKa of the nanoparticle is about 7. In some embodiments, the pKa of the nanoparticle is about 8.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

In some embodiments, the nanoparticle composition comprises a site-directed endonuclease mRNA, such as a SpCas9 mRNA, and gRNAs targeting one or more target sequences. In some embodiments, the SpCas9 mRNA and gRNAs are each separately formulated for delivery, e.g., in lipid nanoparticles. In some embodiments, the SpCas9 mRNA and gRNAs are co-formulated for delivery, e.g., in a lipid nanoparticle. In some embodiments, the nanoparticle composition further comprises a donor polynucleotide, either formulated individually or co-formulated with one or more components of the CRISPR/Cas system.

In some aspects, the disclosure provides lipid-based nanoparticle (LNP) compositions comprising: (a) one or more nucleic acid molecules (e.g., mRNA, gRNA, and/or donor polynucleotide) described herein; and (b) one or more lipid moieties selected from the group consisting of amino lipids, helper lipids, structural lipids, phospholipids, ionizable lipids, PEG lipids, lipoid, and cholesterol or cholesterol derivatives. In some aspects, the disclosure provides lipid-based nanoparticle (LNP) compositions comprising: (a) one or more nucleic acid molecules (e.g., mRNA, gRNA, and/or donor polynucleotide) described herein; and (b) one or more lipid moieties selected from the group consisting of ionizable lipids, amino lipids, anionic lipids, neutral lipids, amphipathic lipids, helper lipids, structural lipids, PEG lipids, and lipoids, and optionally (c) targeting moieties.

I. LNP Components

A. Ionizable lipids

In some embodiments, the LNP composition disclosed herein comprises one or more one or more ionizable lipids. As used herein, the term "ionizable lipid" has its ordinary meaning in the art and may refer to a lipid comprising one or more charged moieties. In some embodiments, an ionizable lipid may be positively charged or negatively charged. In principle, there are no specific limitations concerning the ionizable lipids of the LNP compositions disclosed herein. In some embodiments, the one or more ionizable lipids are selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3ü)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3ü)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3ü)-cholest-5-en-3-yloxy]octyl}oxy)-N,N-dimethyl-3-[(9Z,12Z)-octadeca-9,12-dien-1-y loxy]propan-1-amine (Octyl-CLinDMA (2S)). In one embodiment, the ionizable lipid may be selected from, but not limited to, an ionizable lipid described in International Publication Nos. WO2013086354 and WO2013116126.

In some embodiments, the lipid nanoparticle may include one or more (e.g., 1, 2, 3, 4, 5, 6, 7, or 8) cationic and/or ionizable lipids. Such cationic and/or ionizable lipids include, but are not limited to, 3-(didodecylamino)-N1,N1,4-tridodecyl-1-piperazineethanamine (KL10), N1-[2-(dido- decylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA (2S)).N,N-dioleyl-N,N-dimethylammonium chloride ("DODAC"); N-(2,3-dioleyloxy)propyl-N,N--N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3-β-(N--(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethyl-ammonium trifluoracetate ("DOSPA"), dioctadecylamidoglycyl carboxyspermine ("DOGS"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic and/or ionizable lipids can be used, such as, e.g., LIPOFECTIN® (including DOTMA and DOPE, available from GIBCO/BRL), and LIPOFECTAMINE® (including DOSPA and DOPE, available from GIBCO/BRL). KL10, KL22, and KL25 are described, for example, in U.S. Pat. No. 8,691,750.

B. Amino Lipids

In some embodiments, the LNP composition disclosed herein comprise one or more amino lipids. The terms "amino lipid" and "cationic lipid" are used interchangeably herein to include those lipids and salts thereof having one, two, three, or more fatty acid or fatty alkyl chains and a pH-titratable amino head group (e.g., an alkylamino or dialkylamino head group). In principle, there are no specific limitations concerning the amino lipids of the LNP compositions disclosed herein. The cationic lipid is typically protonated (i.e., positively charged) at a pH below the pKa of the cationic lipid and is substantially neutral at a pH above the pKa. The cationic lipids can also be termed titratable cationic lipids. In some embodiments, the one or more cationic lipids include: a protonatable tertiary amine (e.g., pH-titratable) head group; alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DOTMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, y-DLen-C2-DMA, C12-200, cKK-E12, cKK-A12, cKK-O12, DLin-MC2-DMA (also known as MC2), and DLin-MC3-DMA (also known as MC3).

C. Anionic Lipids

Anionic lipids suitable for use in lipid nanoparticles include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

D. Neutral Lipids

Neutral lipids (including both uncharged and zwitterionic lipids) suitable for use in lipid nanoparticles include, but are not limited to, diacylphosphatidylcholine, diacylphosphatidylethanolamine, ceramide, sphingomyelin, dihydrosphingomyelin, cephalin, sterols (e.g., cholesterol) and cerebrosides. In some embodiments, the lipid nanoparticle comprises cholesterol. Lipids having a variety of acyl chain groups of varying chain length and degree of saturation are available or may be isolated or synthesized by well-known techniques. Additionally, lipids having mixtures of saturated and unsaturated fatty acid chains and cyclic regions can be used. In some embodiments, the neutral lipids used in the disclosure are DOPE, DSPC, DPPC, POPC, or any related phosphatidylcholine. In some embodiments, the neutral lipid may be composed of sphingomyelin, dihydrosphingomyeline, or phospholipids with other head groups, such as serine and inositol.

E. Amphipathic Lipids

In some embodiments, amphipathic lipids are included in nanoparticles. Exemplary amphipathic lipids suitable for use in nanoparticles include, but are not limited to, sphingolipids, phospholipids, fatty acids, and amino lipids.

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular amphipathic lipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural amphipathic lipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the LNP composition disclosed herein comprises one or more phospholipids. In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

Other phosphorus-lacking compounds, such as sphingolipids, glycosphingolipid families, diacylglycerols, and β-acyloxyacids, may also be used. Additionally, such amphipathic lipids can be readily mixed with other lipids, such as triglycerides and sterols.

F. Helper lipids

In some embodiments, the LNP composition disclosed herein comprise one or more helper lipids. The term "helper lipid" as used herein refers to lipids that enhance transfection (e.g., transfection of an LNP comprising an mRNA that encodes a site-directed endonuclease, such as a SpCas9 polypeptide). In principle, there are no specific limitations concerning the helper lipids of the LNP compositions disclosed herein. Without being bound to any particular theory, it is believed that the mechanism by which the helper lipid enhances transfection includes enhancing particle stability. In some embodiments, the helper lipid enhances membrane fusogenicity. Generally, the helper lipid of the LNP compositions disclosure herein can be any helper lipid known in the art. Non-limiting examples of helper lipids suitable for the compositions and methods include steroids, sterols, and alkyl resorcinols. Particularly helper lipids suitable for use in the present disclosure include, but are not limited to, saturated phosphatidylcholine (PC) such as distearoyl-PC (DSPC) and dipalymitoyl-PC (DPPC), dioleoylphosphatidylethanolamine (DOPE), 1,2-dilinoleoyl-sn-glycero-3-phosphocholine (DLPC), cholesterol, 5-heptadecylresorcinol, and cholesterol hemisuccinate. In some embodiments, the helper lipid of the LNP composition includes cholesterol.

G. Structural Lipids

In some embodiments, the LNP composition disclosed herein comprises one or more structural lipids. As used herein, the term "structural lipid" refers to sterols and also to lipids containing sterol moieties. Without being bound to any particular theory, it is believed that the incorporation of structural lipids into the LNPs mitigates aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In some embodiments, the structural lipid is cholesterol. In certain embodiments, the structural lipid is an analog of cholesterol.

H. PEG-Lipids

The lipid component of a lipid nanoparticle composition may include one or more molecules comprising polyethylene glycol, such as PEG or PEG-modified lipids. In some embodiments, the LNP composition disclosed herein comprise one or more polyethylene glycol (PEG) lipid. The term "PEG-lipid" refers to polyethylene glycol (PEG)-modified lipids. Such lipids are also referred to as PEGylated lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines For example, a PEG lipid can be PEG-c-DOMG, PEG-DMG, PEG-DLPE, PEG-DMPE, PEG-DPPC, or a PEG-DSPE lipid. In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example a mPEG-NH$_2$, has a size of about 1000, 2000, 5000, 10,000, 15,000 or 20,000 daltons. In some embodiment, the PEG-lipid is PEG2k-DMG. In some embodiments, the one or more PEG lipids of the LNP composition comprises PEG-DMPE. In some embodiments, the one or more PEG lipids of the LNP composition comprises PEG-DMG.

In some embodiments, an LNP composition comprise one or more nucleic acid molecules described herein. In some embodiments, the LNP composition comprises an mRNA described herein (e.g., an mRNA encoding a site-directed endonuclease, such as a SpCas9 polypeptide). In some embodiments, the LNP compositions comprise one or more gRNA molecules (e.g., one, two, three, or four unique gRNA molecules) described herein. In some embodiments, the LNP composition comprises a donor polynucleotide described herein. In some embodiments, the LNP composition comprises an mRNA described herein (e.g., an mRNA encoding a site-directed endonuclease, such as a SpCas9 polypeptide) and one or more gRNA molecules (e.g., one, two, three, or four unique gRNA molecules) described herein.

In some embodiments, the ratio between the lipid components and the nucleic acid molecules (e.g., mRNA, gRNA, and/or donor polynucleotide) of the LNP composition, e.g., the weight ratio, is sufficient for (i) formation of LNPs with desired characteristics, e.g., size, charge, and (ii) delivery of a sufficient dose of nucleic acid at a dose of the lipid component(s) that is tolerable for in vivo administration as readily ascertained by one of skill in the art.

I. Targeting Moieties

In certain embodiments, it is desirable to target a nanoparticle, e.g., a lipid nanoparticle, using a targeting moiety that is specific to a cell type and/or tissue type. In some embodiments, a nanoparticle may be targeted to a particular cell, tissue, and/or organ using a targeting moiety. In particular embodiments, a nanoparticle comprises a targeting moiety. Exemplary non-limiting targeting moieties include ligands, cell surface receptors, glycoproteins, vitamins (e.g., riboflavin) and antibodies (e.g., full-length antibodies, antibody fragments (e.g., Fv fragments, single chain Fv (scFv) fragments, Fab' fragments, or F(ab')2 fragments), single domain antibodies, camelid antibodies and fragments thereof, human antibodies and fragments thereof, monoclonal antibodies, and multispecific antibodies (e.g., bispecific antibodies)). In some embodiments, the targeting moiety may be a polypeptide. The targeting moiety may include the entire polypeptide (e.g., peptide or protein) or fragments thereof. A targeting moiety is typically positioned on the outer surface of the nanoparticle in such a manner that the targeting moiety is available for interaction with the target, for example, a cell surface receptor. A variety of different targeting moieties and methods are known and available in the art, including those described, e.g., in Sapra et al., Prog. Lipid Res. 42(5):439-62, 2003 and Abra et al., J. Liposome Res. 12:1-3, 2002.

In some embodiments, a lipid nanoparticle (e.g., a liposome) may include a surface coating of hydrophilic polymer chains, such as polyethylene glycol (PEG) chains (see, e.g., Allen et al., Biochimica et Biophysica Acta 1237: 99-108, 1995; DeFrees et al., Journal of the American Chemistry Society 118: 6101-6104, 1996; Blume et al., Biochimica et Biophysica Acta 1149: 180-184,1993; Klibanov et al., Journal of Liposome Research 2: 321-334, 1992; U.S. Pat. No. 5,013,556; Zalipsky, Bioconjugate Chemistry 4: 296-299, 1993; Zalipsky, FEBS Letters 353: 71-74, 1994; Zalipsky, in Stealth Liposomes Chapter 9 (Lasic and Martin, Eds) CRC Press, Boca Raton Fla., 1995). In one approach, a targeting moiety for targeting the lipid nanoparticle is linked to the polar head group of lipids forming the nanoparticle. In another approach, the targeting moiety is attached to the distal ends of the PEG chains forming the hydrophilic polymer coating (see, e.g., Klibanov et al., Journal of Liposome Research 2: 321-334, 1992; Kirpotin et al., FEBS Letters 388: 115-118, 1996).

Standard methods for coupling the targeting moiety or moieties may be used. For example, phosphatidylethanolamine, which can be activated for attachment of targeting moieties, or derivatized lipophilic compounds, such as lipid-derivatized bleomycin, can be used. Antibody-targeted liposomes can be constructed using, for instance, liposomes that incorporate protein A (see, e.g., Renneisen et al., J. Bio. Chem., 265:16337-16342, 1990 and Leonetti et al., Proc. Natl. Acad. Sci. (USA), 87:2448-2451, 1990). Other examples of antibody conjugation are disclosed in U.S. Pat. No. 6,027,726. Examples of targeting moieties can also include other polypeptides that are specific to cellular components, including antigens associated with neoplasms or tumors. Polypeptides used as targeting moieties can be attached to the liposomes via covalent bonds (see, for example Heath, Covalent Attachment of Proteins to Liposomes, 149 Methods in Enzymology 111-119 (Academic Press, Inc. 1987)). Other targeting methods include the biotin-avidin system.

In some embodiments, a lipid nanoparticle includes a targeting moiety that targets the lipid nanoparticle to a cell including, but not limited to, hepatocytes, colon cells, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells (including primary tumor cells and metastatic tumor cells). In particular embodiments, the targeting moiety targets the lipid nanoparticle to a hepatocyte.

J. Lipidoids

The lipid nanoparticles described herein may be lipidoid-based. The synthesis of lipidoids has been extensively described and formulations containing these compounds are particularly suited for delivery of polynucleotides (see Mahon et al., Bioconjug Chem. 2010 21:1448-1454; Schroeder et al., J Intern Med. 2010 267:9-21; Akinc et al., Nat. Biotechnol. 2008 26:561-569; Love et al., Proc Natl Acad Sci USA. 2010 107:1864-1869; Siegwart et al., Proc Natl Acad Sci USA. 2011 108:12996-3001)

According to the present invention, complexes, micelles, liposomes or particles (e.g. nanoparticles) can be prepared containing these lipidoids and therefore, result in an effective delivery of an mRNA or system as described herein, as determined by, for example, the expression and/or activity of the site-directed endonuclease encoded by the mRNA and/or the editing efficiency of the system, following the injection via localized and systemic routes of administration. Pharmaceutical compositions comprising lipidoid complexes can be administered by various means disclosed herein.

The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see e.g., Akinc et al., Mol Ther. 2009 17:872-879), use of lipidoid oligonucleotides to deliver the formulation to other cells types including, but not limited to, endothelial cells, myeloid cells, and muscle cells may not be similarly size-limited.

In one aspect, effective delivery to myeloid cells, such as monocytes, lipidoid formulations may have a similar component molar ratio. Different ratios of lipidoids and other components including, but not limited to, a neutral lipid (e.g., diacylphosphatidylcholine), cholesterol, a PEGylated lipid (e.g., PEG-DMPE), and a fatty acid (e.g., an omega-3 fatty acid) may be used to optimize the formulation of the mRNA or system for delivery to different cell types including, but not limited to, hepatocytes, myeloid cells, muscle cells, etc. Exemplary lipidoids include, but are not limited to, DLin-DMA, DLin-K-DMA, DLin-KC2-DMA, 98N12-5, C12-200 (including variants and derivatives), DLin-MC3-DMA and analogs thereof. The use of lipidoid formulations for the localized delivery of nucleic acids to cells (such as, but not limited to, adipose cells and muscle cells) via either subcutaneous or intramuscular delivery, may also not require all of the formulation components which may be required for systemic delivery, and as such may comprise the lipidoid and the mRNA or system.

In a further embodiment, combinations of different lipidoids may be used to improve the efficacy of an mRNA or system described herein.

According to the present disclosure, an mRNA or system described herein may be formulated by mixing the mRNA or system, or individual components of the system, with the lipidoid at a set ratio prior to addition to cells. In vivo formulations may require the addition of extra ingredients to facilitate circulation throughout the body. After formation of the particle, a mRNA, system, or individual components of a system is added and allowed to integrate with the complex. The encapsulation efficiency is determined using a standard dye exclusion assays.

In vivo delivery of mRNA and/or systems may be affected by many parameters, including, but not limited to, the formulation composition, nature of particle PEGylation, degree of loading, oligonucleotide to lipid ratio, and biophysical parameters such as particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), MD1, DLin-DMA, DLin-K-DMA, DLin-KC2-DMA and DLin-MC3-DMA can be tested for in vivo activity. The lipidoid referred to herein as "98N12-5" is disclosed by Akinc et al., Mol Ther. 2009 17:872-879). The lipidoid referred to herein as "C12-200" is disclosed by Love et al., Proc Natl Acad Sci USA. 2010 107:1864-1869 and Liu and Huang, Molecular Therapy. 2010 669-670.

The ability of a lipidoid-formulated mRNA or system to alter a nucleotide sequence in a gDNA (e.g., correct or induce a mutation) in vitro or in vivo can be determined by any technique known in the art or described herein (e.g., next-generation DNA sequencing).

K. Other Components

The nanoparticles disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

II. Preparation of LNPs

The LNPs of the present disclosure, in which a nucleic acid described herein (e.g., mRNA, gRNA, and/or donor polynucleotide) is entrapped within the lipid portion of the particle and is protected from degradation, can be formed by any method known in the art including, but not limited to, a continuous mixing method, a direct dilution process, and an in-line dilution process. Additional techniques and methods suitable for the preparation of the LNPs described herein include coacervation, microemulsions, supercritical fluid technologies, phase-inversion temperature (PIT) techniques.

In some embodiments, the LNPs of the present disclosure are produced via a continuous mixing method, e.g., a process that includes providing an aqueous solution a nucleic acid described herein (e.g., mRNA, gRNA, and/or donor polynucleotide) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid molecule within the lipid vesicle. This process and the apparatus for carrying out this process are known in the art. More information in this regard can be found in, for example, U.S. Patent Publication No. 20040142025, the disclosure of which is herein incorporated by reference. The action of continuously introducing lipid and buffer solutions into a mixing environment, such as in a mixing chamber, causes a continuous dilution of the lipid solution with the buffer solution, thereby producing a lipid vesicle substantially instantaneously upon mixing. By mixing the aqueous solution comprising a nucleic acid molecule with the organic lipid solution, the organic lipid solution undergoes a continuous stepwise dilution in the presence of the buffer solution (e.g., aqueous solution) to produce a nucleic acid-lipid particle.

In some embodiments, the LNPs of the present disclosure are produced via a direct dilution process that includes forming a lipid vesicle (e.g., liposome) solution and immediately and directly introducing the lipid vesicle solution into a collection vessel containing a controlled amount of dilution buffer. In some embodiments, the collection vessel includes one or more elements configured to stir the contents of the collection vessel to facilitate dilution. In some embodiments, the amount of dilution buffer present in the collection vessel is substantially equal to the volume of lipid vesicle solution introduced thereto.

In some embodiments, the LNPs of the present disclosure are produced via an in-line dilution process in which a third reservoir containing dilution buffer is fluidly coupled to a second mixing region. In these embodiments, the lipid vesicle (e.g., liposome) solution formed in a first mixing region is immediately and directly mixed with dilution buffer in the second mixing region. These processes and the apparatuses for carrying out direct dilution and in-line dilution processes are known in the art. More information in this regard can be found in, for example, U.S. Patent Publication No. 20070042031, the disclosure of which is herein incorporated by reference.

Pharmaceutical Compositions

The present disclosure includes pharmaceutical compositions comprising an mRNA, one or more gRNAs, and/or a donor polynucleotide described herein, in combination with one or more pharmaceutically acceptable excipient, carrier or diluent.

Exemplary pharmaceutically acceptable excipients such as carriers, solvents, stabilizers, adjuvants, diluents, etc., depending upon the particular mode of administration and dosage form. Contemplated pharmaceutical compositions can be generally formulated to achieve a physiologically compatible pH, and range from a pH of about 3 to a pH of about 11, about pH 3 to about pH 7, depending on the formulation and route of administration. In alternative examples, the pH can be adjusted to a range from about pH 5.0 to about pH 8. In some examples, the compositions comprise a therapeutically effective amount of at least one compound as described herein, together with one or more pharmaceutically acceptable excipients.

Suitable excipients can include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Pharmaceutical compositions can be formulated into preparations in solid, semisolid, liquid or gaseous forms, such as tablets, capsules, powders, granules, ointments, solutions, suppositories, injections, inhalants, gels, microspheres, and aerosols. As such, administration of a gRNA and/or mRNA and/or donor polynucleotide described herein can be achieved in various ways, including oral, buccal, rectal, parenteral, intraperitoneal, intradermal, transdermal, intratracheal, intraocular, etc., administration. The active agent can be systemic after administration or can be localized using regional administration, intramural administration, or use of an implant that acts to retain the active dose at the site of implantation. The active agent can be formulated for immediate activity or it can be formulated for sustained release.

In some cases, the components of the composition are individually pure, e.g., each of the components is at least about 75%, at least about 80%, at least about 90%, at least about 95%, at least about 98%, at least about 99%, or at least 99%, pure. In some cases, the individual components of a composition are pure before being added to the composition.

In some embodiments, the mRNA, one or more gRNA, and/or donor polynucleotides is encapsulated in a nanoparticle, e.g., a lipid nanoparticle. In some embodiments, the gRNA is encapsulated in a nanoparticle, e.g., a lipid nanoparticle. In some embodiments, the mRNA encoding a Cas nuclease (e.g. SpCas9) described herein is encapsulated in a nanoparticle, e.g., lipid nanoparticle. In particular embodiments, an mRNA encoding a Cas nuclease (e.g., SpCas9 polypeptide) described herein or lipid nanoparticle encapsulating an mRNA described herein is present in a pharmaceutical composition.

In particular embodiments, the mRNA encoding the site-directed endonuclease or nanoparticle encapsulating the mRNA encoding the site-directed endonuclease is present in a pharmaceutical composition. In various embodiments, the mRNA present in the pharmaceutical composition is encapsulated in a nanoparticle, e.g., a lipid nanoparticle. In some embodiments, the mRNA encoding the site-directed endonuclease and gRNA is encapsulated in a nanoparticle. In some embodiments, the mRNA encoding the site-directed endonuclease and gRNA is encapsulated in a nanoparticle at a mRNA:gRNA weight ratio of about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1 (wt/wt). In some embodiments, the mRNA:gRNA weight ratio is about 1:1.

In one embodiment, the lipid nanoparticles can comprise polynucleotides (e.g., donor polynucleotide) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles can comprise the donor polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

Typically, an effective amount of a CRISPR/Cas system comprising an mRNA described herein, and/or one or more guide RNAs and/or donor polynucleotide can be provided. The amount of recombination can be measured by any convenient method, e.g. as described above, and known in the art. The calculation of the effective amount or effective dose of a CRISPR/Cas system comprising an mRNA described herein, and/or one or more guide RNAs and/or donor polynucleotide to be administered is within the skill of one of ordinary skill in the art, and can be routine to those persons skilled in the art. The final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression of the disease condition as required. Utilizing LD50 animal data, and other information available for the agent, a clinician can determine the maximum safe dose for an individual, depending on the route of administration. For instance, an intravenously administered dose can be more than an intrathecally administered dose, given the greater body of fluid into which the therapeutic composition is being administered. Similarly, compositions which are rapidly cleared from the body can be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a CRISPR/Cas system comprising an mRNA described herein, and/or one or more guide RNA and/or donor polynucleotide can be obtained from a suitable commercial source. As a general proposition, the total pharmaceutically effective amount of a CRISPR/Cas system comprising an mRNA described herein, and/or one or more guide RNA and/or donor polynucleotide administered parenterally per dose will be in a range that can be measured by a dose response curve.

Therapies based on a CRISPR/Cas system comprising an mRNA described herein, and/or one or more guide RNA and/or donor polynucleotide to be used for therapeutic administration, must be sterile. Sterility is readily accomplished by filtration through sterile filtration membranes (e.g., 0.2 µm membranes). Therapeutic compositions can be generally placed into a container having a sterile access port, for example, an intravenous solution bag or vial having a stopper pierceable by a hypodermic injection needle. The therapies based on a CRISPR/Cas system comprising an mRNA described herein, and/or one or more guide RNA and/or donor polynucleotide can be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous solution of compound, and the resulting mixture is lyophilized. The infusion solution can be prepared by reconstituting the lyophilized compound using bacteriostatic Water-for-Injection.

Methods of Use

Provided herein are cellular, ex vivo and in vivo methods for using the CRISPR/Cas systems, the delivery systems, or pharmaceutical compositions provided herein, to create permanent changes in one or more target genes in the genome. Such methods use a Cas nuclease (e.g., SpCas9 polypeptide) encoded by an mRNA described herein, one or more gRNAs, and optionally a donor polynucleotide, to permanently delete (excise), insert, or replace (delete and insert) exons and/or introns in target genes in the genome.

In some aspects, the disclosure provides methods for inducing a double-stranded break (DSB) in a target gene in a cell. The method includes contacting the cell with: (i) the mRNA provided herein and at least one gRNA directed to the target gene; (ii) the system provided herein; or (iii) the pharmaceutical composition provided herein, wherein the mRNA is translated when the mRNA, the system, or the composition contacts the cell and provides a site-directed endonuclease that combines with the gRNA to induce a DSB at a site in the target gene.

In some aspects, the disclosure provides methods for correcting a mutation in a target gene in a cell. The method includes contacting the cell with the mRNA provided herein, at least one gRNA directed to the target gene, and a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) DNA repair pathway inserts the donor polynucleotide into the DSB at a location proximal to the mutation, thereby correcting the mutation.

In some aspects, the disclosure provides methods for treating, preventing, reducing the risk or likelihood of developing (e.g., reducing the susceptibility to), delaying the onset of, and/or ameliorating one or more symptoms associated with a health condition or a disease in a mammal (e.g., human) in need thereof, the method including administering to the mammal a therapeutically effective amount of an mRNA, a CRISPR/Cas system, a delivery system, or a pharmaceutical composition described herein.

In some embodiments, the cell is a eukaryotic cell. Non-limiting examples of eukaryotic cells include yeast cells, plant cells, insect cells, cells from an invertebrate animal, cells from a vertebrate animal, mammalian cells, rodent cells, mouse cells, rat cells, and human cells. In some embodiments, the eukaryotic cell may be a mammalian cell. In some embodiments, the eukaryotic cell may be a rodent cell. In some embodiments, the eukaryotic cell may be a non-human primate cell. In some embodiments, the eukaryotic cell may be a human cell. Similarly, the target sequence may be from any such cells or in any such cells.

The mRNA, system, or pharmaceutical composition described herein may be introduced into the cell via any methods known in the art, such as, e.g., viral or bacteriophage infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, shear-driven cell permeation, fusion to a cell-penetrating peptide followed by cell contact, microinjection, and nanoparticle-mediated delivery. In some embodiments, the vector system may be introduced into the cell via viral infection.

In some aspects, the disclosure provides methods of treating a patient with a disease by inducing a DSB in a target gene in a cell. The method includes isolating a cell from the patient, and contacting the cell with: (i) the mRNA provided herein and at least one gRNA directed to the target gene; (ii) the system provided herein; or (iii) the pharmaceutical composition provided herein, wherein the mRNA is translated when the mRNA, system, or composition contacts the cell and provides a site-directed endonuclease that combines with the gRNA to induce a DSB at a site in the target gene.

In some aspects, the disclosure provides methods of treating a patient with a disease by inducing a DSB in a target gene in a cell. The method includes administering to the patient an effective amount of: (i) the mRNA provided herein and at least one gRNA directed to the target gene; (ii) the system provided herein; or (iii) the pharmaceutical composition provided herein, wherein the mRNA is translated when the mRNA, system, or composition contacts the cell and provides a site-directed endonuclease that combines with the gRNA to induce a DSB at a site in the target gene.

In some aspects, the disclosure provides methods of treating a patient with a disease by correcting a mutation in a target gene in a cell. The method includes isolating a cell from the patient; and contacting the cell with the mRNA provided herein, at least one gRNA directed to the target gene, and a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) DNA repair pathway inserts the donor polynucleotide into the DSB at a location proximal to the mutation, thereby correcting the mutation.

In some aspects, the disclosure provides methods of treating a patient with a disease by correcting a mutation in a target gene in a cell. The method includes administering to the patient an effective amount of the mRNA provided herein, at least one gRNA directed to the target gene, and a donor polynucleotide, wherein the mRNA is translated when the mRNA contacts the cell and provides a site-directed endonuclease that combines with the gRNA to induce a DSB at a site in or near the mutation in the target gene, and wherein a non-homologous end-joining (NHEJ) DNA repair pathway inserts the donor polynucleotide into the DSB at a location proximal to the mutation, thereby correcting the mutation.

As used herein, the terms "administration" and "administering," refers to the delivery of an mRNA or CRISPR/Cas system described herein, e.g., via a delivery system described herein, or a pharmaceutical composition thereof, by an administration route comprising, but not limited to, oral, intravenous, intra-arterial, intramuscular, intraperitoneal, subcutaneous, intramuscular, and topical administration, or combinations thereof. The term includes, but is not limited to, administering by a medical professional and self-administering.

In some aspects, the methods comprise administration of an mRNA, CRISPR/Cas system, delivery system, or pharmaceutical composition described herein, as an ex vivo cell-based therapy. For example, a patient specific iPS cell line is created. Then, the chromosomal DNA of these iPS cells is corrected using the materials and methods described herein. Next, the corrected iPSCs are differentiated. Finally, the progenitor cells are implanted into the patient. There are many advantages to this ex vivo approach. One advantage of an ex vivo cell therapy approach is the ability to conduct a comprehensive analysis of the therapeutic prior to administration. All nuclease-based therapeutics have some level of off-target effects. Performing gene correction ex vivo allows one to fully characterize the corrected cell population prior to implantation. Another advantage of ex vivo cell therapy relates to genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability.

In some aspects, the methods comprise administration of an mRNA, CRISPR/Cas system, delivery system, or pharmaceutical composition described herein, as an in vivo based therapy. In this method, the chromosomal DNA of the cells in the patient is corrected using the materials and methods described herein. An advantage of in vivo gene therapy is the ease of therapeutic production and administration.

In some embodiments, the methods comprise administering an mRNA, CRISPR/Cas system, delivery system, or pharmaceutical composition described herein to a patient in need thereof. In some embodiments, the method is used as a single therapy or in combination with other therapies known in the art.

In some embodiments, the patient may have a mutation (such as, e.g., insertion, deletion, substitution, chromosome translocation) in a disease-associated gene. In some embodiments, administration of the mRNA, CRISPR/Cas system, delivery system, or pharmaceutical composition may result in a mutation comprising an insertion, deletion, or substitution of one or more nucleotides of the disease-associated gene in the patient. Certain embodiments may include methods of repairing the patient's mutation in the disease-associated gene. In some embodiments, the mutation may result in one or more amino acid changes in a protein expressed from the disease-associated gene. In some embodiments, the mutation may result in one or more nucleotide changes in an RNA expressed from the disease-associated gene. In some embodiments, the mutation may alter the expression level of the disease-associated gene. In some embodiments, the mutation may result in increased or decreased expression of the gene. In some embodiments, the mutation may result in gene knockdown in the patient. In some embodiments, the administration of the mRNA, CRISPR/Cas system, delivery system, or pharmaceutical composition may result in the correction of the patient's mutation in the disease-associated gene. In some embodiments, the administration of the mRNA, CRISPR/Cas system, delivery system, or pharmaceutical composition may result in gene knockout in the patient. In some embodiments, the administration of the mRNA, CRISPR/Cas system, delivery system, or pharmaceutical composition may result in replacement of an exon sequence, an intron sequence, a transcriptional control sequence, a translational control sequence, or a non-coding sequence of the disease-associated gene.

In some embodiments, the administration of the mRNA, CRISPR/Cas system, delivery system, or pharmaceutical composition may result in integration of an exogenous sequence (e.g., a donor polynucleotide sequence) into the patient's genomic DNA. In some embodiments, the exogenous sequence may comprise a protein or RNA coding sequence operably linked to an exogenous promoter sequence such that, upon integration of the exogenous sequence into the patient's genomic DNA, the patient is capable of expressing the protein or RNA encoded by the integrated sequence. The exogenous sequence may provide a supplemental or replacement protein coding or non-coding sequence. For example, the administration of the mRNA, CRISPR/Cas system, delivery system, or pharmaceutical composition may result in the replacement of the mutant portion of the disease-associated gene in the patient. In some embodiments, the mutant portion may include an exon of the disease-associated gene. In other embodiments, the integration of the exogenous sequence may result in the expression of the integrated sequence from an endogenous promoter sequence present on the patient's genomic DNA. For example, the administration of the mRNA, CRISPR/Cas system, delivery system, or pharmaceutical composition may result in supply of a functional gene product of the disease-associated gene to rectify the patient's mutation. In yet other embodiments, the administration of the mRNA, CRISPR/Cas system, delivery system, or pharmaceutical composition may result in integration of an exon sequence, an intron sequence, a transcriptional control sequence, a translational control sequence, or a non-coding sequence into the patient's genomic DNA.

Additional embodiments of the invention also encompass methods of treating the patient in a tissue-specific manner Non-limiting examples of suitable tissues for treatment by the methods include the immune system, neuron, muscle, pancreas, blood, kidney, bone, lung, skin, liver, and breast tissues.

Kits

The present disclosure provides kits for carrying out the methods described herein. A kit can include an mRNA described herein, one or more gRNA, and optionally a donor polynucleotide, sufficient to carry out the aspects of the methods described herein. Components of a kit can be in separate containers, or combined in a single container.

In some embodiments, a kit comprises an mRNA described herein and instructions for use with one or more gRNAs, and optionally a donor polynucleotide, for editing a target gene in a cell. In some embodiments, the kit is for inducing a DSB in a target gene in a cell. The kit can include a container comprising an mRNA provided herein, the system provided herein, or the pharmaceutical composition provided herein, and a package insert comprising instructions for use.

Any kit described above can further comprise one or more additional reagents, where such additional reagents are selected from a buffer, a buffer for introducing a nucleic acid or delivery system described herein into a cell, a wash buffer, a control reagent, a control vector, a control RNA polynucleotide, a reagent for in vitro production of the polypeptide (e.g., SpCas9 polypeptide) from an mRNA described herein, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the SpCas9 polypeptide encoded by an mRNA described herein, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a," "an," and "the" include plural references unless the context clearly dictates otherwise. For example, the term "a cell" includes one or more cells, comprising mixtures thereof. "A and/or B" is used herein to include all of the following alternatives: "A," "B," "A or B," and "A and B."

The term "about," as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

It is understood that aspects and embodiments of the disclosure described herein include "comprising," "consisting," and "consisting essentially of" aspects and embodiments.

The terms "individual," "subject," "host," and "patient," are used interchangeably herein and refer to any mammalian subject, such as human (e.g., human subjects), non-human mammals and non-human primates, for whom diagnosis, treatment, or therapy is desired, particularly humans.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein. In some embodiments, a nucleic acid molecule of the disclosure is an mRNA described herein, such as an mRNA encoding a site-directed endonuclease, such as a SpCas9 polypeptide described herein. In some embodiments, a nucleic acid molecule of the disclosure is a gRNA described herein. In some embodiments, a nucleic acid molecule of the disclosure is a donor polynucleotide described herein.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, or mafft.cbrc.jp/alignment/software/. See, e.g., Altschul et al. (1990), J. Mol. Biol. 215:403-10. Sequence alignments standard in the art are used according to the disclosure to determine nucleotides in an mRNA described herein that "correspond to" nucleotides in another mRNA. The nucleotides of the first mRNA that correspond to nucleotides of the second mRNA appear at the same position in alignments of the sequences.

A DNA sequence that "encodes" a particular RNA is a DNA nucleic acid sequence that is transcribed into RNA. A DNA polynucleotide can encode an RNA (mRNA) that is translated into protein, or a DNA polynucleotide can encode an RNA that is not translated into protein (e.g. tRNA, rRNA, or a guide RNA; also called "non-coding" RNA or "ncRNA"). A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The term "recombinant" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector (e.g., an AAV). As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence.

The term "operably linked," as used herein, denotes a physical or functional linkage between two or more elements, e.g., polypeptide sequences or polynucleotide sequences, which permits them to operate in their intended fashion. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements are contiguous or non-contiguous.

As used herein, the term "genomic DNA (gDNA)" refers to the DNA of a genome of an organism including, but not limited to, the DNA of the genome of a bacterium, fungus, archea, plant or animal As used herein, the term "manipulating" or "editing" DNA encompasses binding, or cleaving (i.e., cutting) one or both strands of the DNA, or encompasses modifying the DNA or a polypeptide associated with the DNA. Manipulating or editing DNA can silence, activate, or modulate (either increase or decrease) the expression of an RNA or polypeptide encoded by the DNA.

As used herein, the terms "nuclease" and "endonuclease" are used interchangeably herein to mean an enzyme which possesses endonucleolytic catalytic activity for polynucleotide cleavage. The term includes site-specific endonucleases such as site-specific endonucleases of clustered, regularly interspaced, short palindromic repeat (CRISPR) systems such as, e.g., Cas polypeptides, e.g., a SpCas9 polypeptide.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

A "target DNA" as used herein is a DNA polynucleotide that comprises a "target site" or "target sequence." The terms "target site," "target sequence," "target protospacer DNA, " or "protospacer-like sequence" are used interchangeably herein to refer to a nucleic acid sequence present in a target DNA to which a DNA-targeting segment (e.g., spacer or spacer sequence) of a guide RNA will bind, provided sufficient conditions for binding exist. For example, the target site (or target sequence) 5'-GAGCATATC-3' within a target DNA is targeted by (or is bound by, or hybridizes with, or is complementary to) the RNA sequence 5'-GAUAUG-CUC-3'. Suitable DNA/RNA binding conditions include physiological conditions normally present in a cell. Other suitable DNA/RNA binding conditions (e.g., conditions in a cell-free system) are known in the art; see, e.g., Sambrook, supra. The target DNA can be a double-stranded DNA. The strand of the target DNA that is complementary to and hybridizes with the guide RNA is referred to as the "complementary strand" and the strand of the target DNA that is complementary to the "complementary strand" (and is therefore not complementary to the guide RNA) is referred to as the "noncomplementary strand" or "non-complementary strand." The target DNA can be within a target gene.

By "site-directed endonuclease," it is meant a polypeptide (e.g., Cas9 polypeptide, SpCas9 polypeptide) that binds gRNA and is targeted to a specific DNA sequence. A site-directed endonuclease as described herein is targeted to a specific DNA sequence by the RNA molecule (e.g., gRNA) to which it is bound. The RNA molecule comprises a sequence that binds, hybridizes to, or is complementary to a target sequence within the target DNA, thus targeting the bound polypeptide (e.g., Cas9 polypeptide, SpCas9 polypeptide) to a specific location within the target DNA (the target sequence). By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain aspects, a complex comprising a guide RNA and a site-directed modifying polypeptide is used for targeted double-stranded DNA cleavage.

As used herein, the term "SpCas9 polypeptide" refers to a Cas9 polypeptide derived from S. pyogenes. As used herein, the term "SpCas9 mRNA" refers to an mRNA encoding a SpCas9 polypeptide.

As used herein, "homology-directed repair (HDR)" refers to the specialized form DNA repair that takes place, for example, during repair of double-strand breaks in cells. This process requires nucleotide sequence homology, uses a "donor" molecule to template repair of a "target" molecule (e.g., the one that experienced the double-strand break), and leads to the transfer of genetic information from the donor to the target. Homology-directed repair may result in an alteration of the sequence of the target molecule (e.g., insertion, deletion, mutation), if the donor polynucleotide differs from the target molecule and part or all of the sequence of the donor polynucleotide is incorporated into the target DNA. In some embodiments, the donor polynucleotide, a portion of the donor polynucleotide, a copy of the donor polynucleotide, or a portion of a copy of the donor polynucleotide integrates into the target DNA.

As used herein, the term "non-homologous end joining (NHEJ)" refers to the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

The terms "treatment," "treating," and the like are used herein to generally mean obtaining a desired pharmacologic and/or physiologic effect. The effect is prophylactic in terms of completely or partially preventing a disease or symptom thereof and/or is therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which is predisposed to acquiring the disease or symptom but has not yet been diagnosed as having it; (b) inhibiting the disease or symptom, e.g., arresting its development; or (c) relieving the disease, e.g., causing regression of the disease. The therapeutic agent is administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The therapy will desirably be administered during the symptomatic stage of the disease, and in some cases after the symptomatic stage of the disease.

EXAMPLES

The present disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

The practice of the present disclosure will employ, unless otherwise indicated, techniques of molecular biology, microbiology, cell biology, biochemistry, nucleic acid chemistry, and immunology, which are known to those skilled in the art. Such techniques are explained in the literature, such as, Molecular Cloning: A Laboratory Manual, fourth edition (Sambrook et al., 2012) and Molecular Cloning: A Laboratory Manual, third edition (Sambrook and Russel, 2001), (jointly referred to herein as "Sambrook"); Current Protocols in Molecular Biology (F.M. Ausubel et al., eds., 1987, including supplements through 2014); PCR: The Polymerase Chain Reaction, (Mullis et al., eds., 1994); Beaucage et al. eds., Current Protocols in Nucleic Acid Chemistry, John Wiley & Sons, Inc., New York, 2000, (including supplements through 2014), Gene Transfer and Expression in Mammalian Cells (Makrides, ed., Elsevier Sciences B.V., Amsterdam, 2003); and Current Protocols in Immunology (Horgan K and S. Shaw (1994), including supplements through 2014). As appropriate, procedures involving the use of commercially available kits and reagents are generally carried out in accordance with manufacturer defined protocols and/or parameters unless otherwise noted.

Example 1: Preparation of Optimized mRNA Encoding a Site-Specific Endonuclease

Messenger RNA (mRNA) encoding a site-directed endonuclease is a valuable tool for use in gene-editing systems. However, administration of exogenous mRNA can activate host innate immune response pathways, which is detrimental to mRNA expression and can result in a potentially toxic inflammatory response. Uridine-rich motifs present in exogenous mRNA have been shown to induce innate immune activation, for example, by stimulating RIG-1 (retinoic acid-inducible gene I) pattern recognition receptor (see, e.g., Chiang, et al (2015) *J. VIROL.* 89:8011; Runge, et al (2014) *PLoS PATHOG.* 10:e1004081; Saito, et al (2008) *NATURE* 454:523). Thus, it was evaluated if mRNA with uridine depletion and/or chemical modification of uridine would provide efficient translation of an encoded Cas9 site-directed endonuclease while reducing undesirable immune activation.

Towards this end, a parent mRNA (i.e., reference mRNA) for generating SpCas9 (SEQ ID NO: 6) was prepared. The parent mRNA included a synthetic 5' UTR, an open-reading frame (ORF) encoding an N-terminal nuclear localization signal derived from SV40 (SEQ ID NO: 8), SpCas9 (SEQ ID NO: 6), and a C-terminal NLS derived from nucleoplasmin (SEQ ID NO: 7), a 3' UTR, and a poly-A-tail. The parent mRNA was cloned into an mRNA expression vector, which contained a T7 RNA polymerase promoter. A transcription template was generated by PCR.

Sequence modified versions of the parent mRNA were prepared. This included "RNA-009", which was prepared as a codon-optimized version of the parent mRNA using an algorithm designed by Atum (Newark, CA). Additionally, a uridine-depleted version of RNA-009 was prepared ("RNA-013") using an algorithm designed by Geneious (San Diego, CA). Furthermore, "RNA-012" was prepared as a codon-optimized and uridine-depleted version of the parent mRNA using the Geneious algorithm The nucleotide sequences of the parent mRNA and RNA-009 (including ORF, 5' UTR, and 3' UTR) are identified in Table 3.

TABLE 3

Sequences of mRNA encoding SpCas9

| Sequence Name | DNA SEQ ID NO: | RNA SEQ ID NO: | Amino Acid SEQ ID NO: |
|---|---|---|---|
| Parent mRNA | | | |
| Full-length mRNA | 16 | 17 | — |
| RNA-009 (Sequence Optimtzed from Parent mRNA) | | | |
| Full-length mRNA | 1 | 2 | — |
| 5' UTR | 9 | 10 | — |
| Coding Region | 3 | 4 | 5 |
| 3' UTR | 11 | 12 | — |
| Poly-A Tail | 13 | 13 | — |

The base content of the parent mRNA, RNA-009, RNA-012, and RNA-013 was quantified and provided in Table 4. While the RNA-009 had increased uridine content compared to the parent mRNA, RNA-012 and RNA-013 had reduced uridine content relative to both.

TABLE 4

Percent Nucleotide Base Content of SpCas9 mRNA

| Nucleotide | Parent mRNA | RNA-009 | RNA-012 | RNA-013 |
|---|---|---|---|---|
| A | 30.8 | 30.7 | 28.0 | 28.0 |
| C | 26.8 | 25.8 | 29.2 | 29.2 |
| G | 27.1 | 25.6 | 30.1 | 30.2 |
| U | 15.2 | 17.9 | 12.7 | 12.6 |

Additionally, the parent mRNA and RNA-009, RNA-012, and RNA-013 were aligned and sequence similarity was determined. As shown in Table 5, RNA-009 shared 84.3% sequence similarity with the parent mRNA, while the codon-optimized and uridine depleted RNA-012 and RNA-013 shared 99.6% sequence similarity (corresponding to a difference in approximately 16 nucleotides).

TABLE 5

Percent Pairwise Sequence Identity of SpCas9 mRNA Coding Regions

| Parent mRNA | RNA-009 | RNA-012 | RNA-013 | |
|---|---|---|---|---|
| 100 | 84.3 | 92.4 | 92.0 | Parent mRNA |
| 84.3 | 100 | 86.0 | 85.8 | RNA-009 |
| 92.4 | 86.0 | 100 | 99.6 | RNA-012 |
| 92.0 | 85.8 | 99.6 | 100 | RNA-013 |

Preparation of mRNA transcripts from parent mRNA, RNA-009, RNA-012, and RNA-013 mRNA constructs was performed using T7 RNA polymerase in vitro transcription (IVT) with co-transcriptional capping using a m$^7$GpppG Cap-1. For unmodified mRNA, transcription was performed using a mixture of adenosine triphosphate (ATP), cytidine triphosphate (CTP), guanosine triphosphate (GTP), and uridine triphosphate (UTP). For chemically modified mRNA, transcription was performed with a UTP analog in place of UTP. The mRNA prepared are depicted in Table 6. The mRNA transcripts were purified using a combination of chromatographic techniques to enrich for full-length product and remove reaction byproducts, sequentially.

TABLE 6

Base Modifications of SpCas9 mRNA Constructs

| mRNA | Uridine Base Modification |
|---|---|
| RNA-009u | Unmodified |
| RNA-009n | N1-methylpseudouridine |
| RNA-009p | Pseudouridine |
| RNA-009m | 5-methoxyuridine |
| RNA-012u | Unmodified |
| RNA-012n | N1-methylpseudouridine |
| RNA-013n | N1-methylpseudouridine |

Example 2: Evaluation of Optimized mRNA for Editing the Transferrin Gene Locus in Mice In vivo editing efficiency and tolerability of sequence optimized SpCas9 RNA-009 (SEQ ID NO: 2) was evaluated in C57BL/6 mice. The RNA-009 transcripts contained either unmodified uridine (RNA-009u) or modified uridine (RNA-009m or RNA-009n) and were prepared as described in Example 1.

Editing of a target gene sequence in the transferrin gene locus was evaluated. For in vivo administration, the SpCas9 mRNA and mTF_T2 sgRNA were co-formulated as lipid nanoparticles ("RNA-LNP") at a 1:1 mRNA:gRNA weight ratio. The LNPs were diluted in PBS to deliver the desired dose in a volume of 10 mL per kg of body weight.

C57BL/6 mice were administered the co-formulated RNA-LNP by intravenous tail vein injection at a dose of 0.4 mpk (N=4 per group). The dosage is expressed in mg of encapsulated RNA (mg of SpCas9 mRNA +mg of mTF_T2 sgRNA) administered per kg of body weight ("mpk"). Negative control mice were administered an equivalent volume of PBS by intravenous tail vein injection.

To evaluate editing efficiency, liver tissue was isolated from sacrificed mice at approximately 96 hours post-administration. The tissue was homogenized and genomic DNA was extracted using a Qiagen DNeasy Blood and Tissue Kit (Cat #69506) according to the manufacturer's protocol. The target sequence in the transferrin gene locus was amplified by PCR and sequenced. Indels were measured by TIDE analysis software as described by Brinkman et al., Nucleic Acids Res. 2014 December 16; 42(22):e168. As shown in FIG. 1, RNA-009 with N1-methylpseudouridine (RNA-009n) had improved editing efficiency compared to RNA-009 with unmodified uridine (RNA-009u) or RNA-009 with 5-methoxy uridine (RNA-009m).

Figure 2A:
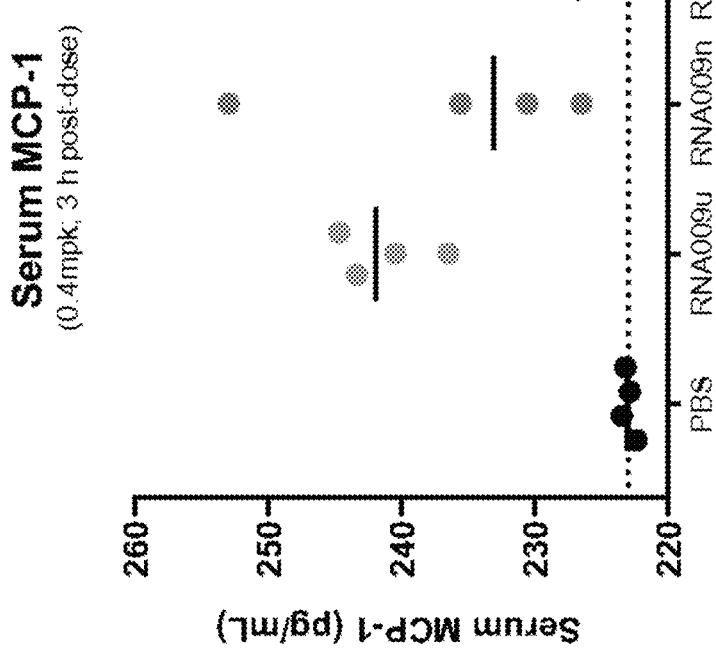
FIGS. 2A-2B provide graphs quantifying levels of IL-6 (FIG. 2A) and MCP-1 (FIG. 2B) in serum isolated from the mice of FIG. 1.
Figure 2B:
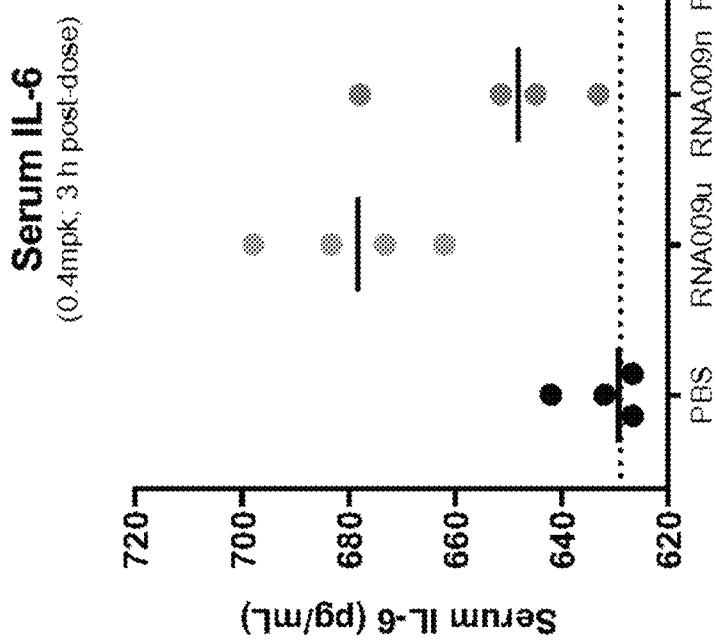

To evaluate tolerability, levels of IL-6 and MCP-1 inflammatory cytokines were measured in serum of mice in response to administration of co-formulated RNA-LNP. Briefly, mouse serum was isolated at 3 hours following administration of co-formulated RNA-LNP. MCP-1 and IL-6 were measured by MSD Mouse MCP-1 Kit and MSD Mouse IL-6 Kit (MESO SCALE DIAGNOSTICS, LLC (MSD)) according to the manufacturer's protocol. Both IL-6 (FIG. 2A) and MCP-1 (FIG. 2B) levels were elevated in mice that received RNA-009u when compared to control mice. However, cytokine levels were reduced for mice that received RNA-009 with uracil base modification (RNA-009n or RNA-009m).

Together, these data indicated RNA-009 incorporating an N1-methylpseudouridine modification provided highly efficient gene editing but did not induce aberrant innate immune activation.

Example 3: Evaluation of Optimized mRNA for Editing the Albumin Locus in Mice In vivo editing efficiency of sequence optimized SpCas9 RNA-009n was compared to SpCas9 parent mRNA in C57BL/6 mice. Parent mRNA and the RNA-009n transcripts were prepared as described in Example 1.

Editing efficiency was evaluated using gRNA targeting a sequence in the albumin gene locus of C57BL/6 mice (mAlbT1). The SpCas9 mRNA and mAlbT1 sgRNA were co-formulated as LNPs as described in Example 2.

C57BL/6 mice were administered co-formulated RNA-LNP containing RNA-009n or parent mRNA (N=4 per group). The mice were administered an intravenous injection by tail vein at a dose of 1.0 mpk. Liver tissue was isolated at approximately 96 hours following LNP administration. Editing efficiency was evaluated by TIDE analysis of liver tissue as described in Example 2. Editing efficiency of RNA-009n was evaluated for three independent mouse cohorts.

The frequency of INDEL formation at the albumin target sequence is shown in Table 7. The INDEL frequency exceeded 30% in each cohort treated with RNA-009n but was significantly lower (approximately 10%) for mice administered parent mRNA.

TABLE 7

In Vivo Editing Efficiency of Albumin Gene Locus in Mice

| mRNA | Frequency of INDELs (%) |
| --- | --- |
| Parent mRNA | 10.0 ± 0.6 |
| RNA-009n | 32.0 ± 3.6 |
|  | 40.3 ± 6.6 |
|  | 36.8 ± 1.2 |

Example 4: Comparison of Optimized mRNA for Editing the Transferrin Gene Locus in Mice In vivo editing efficiency and tolerability of RNA-009n was further compared to RNA-012 and RNA-013 with N1-methylpseudouridine modification (RNA-012n and RNA-013n respectively). The SpCas9 RNA-009n, RNA-012n, and RNA-013n transcripts were prepared as described in Example 1. SpCas9 mRNA and mTF_T2 sgRNA were co-formulated as LNPs as described in Example 2. Co-formulated RNA-LNP was administered by intravenous tail vein injection at a dose of 0.4 mpk. The RNA-LNP was diluted in PBS to enable administration in a volume of 10 mL per kg of body weight. Negative control mice received an intravenous injection of PBS alone.

Figure 3:
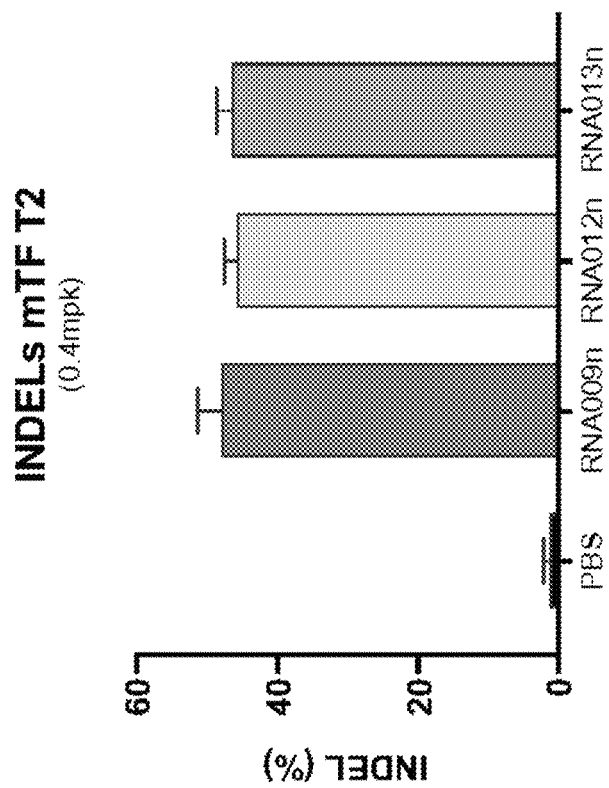
FIG. 3 provides a graph showing frequency of INDELs in liver tissue of mice administered LNPs containing mTF_T2 sgRNA and SpCas9 mRNA that was either RNA-009n, RNA-012n, or RNA-013n. RNA-012n and RNA-013n encoded a sequence optimized, uridine-depleted mRNA sequence and were modified throughout with N1-methylpseudouridine. Comparison was made to control mice administered PBS only.

Editing efficiency was determined by measuring INDEL frequency at the transferrin target gene sequence in liver tissue as described in Example 2. Liver tissue was isolated at approximately 96 hours post-administration of co-formulated RNA-LNP. As shown in FIG. 3, the frequency of INDELs was similar for RNA-009n, RNA-012n, and RNA-013n.

Figure 4A:
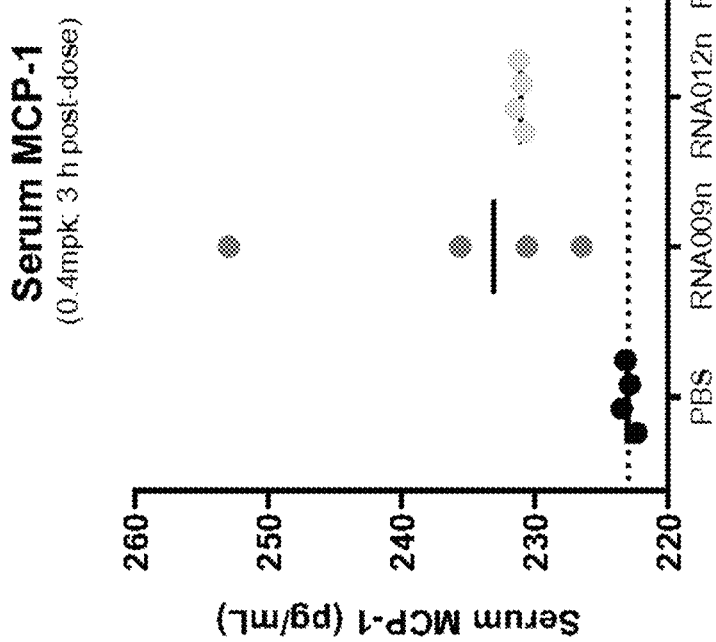
FIGS. 4A-4B provide graphs quantifying levels of IL-6 (FIG. 4A) and MCP-1 (FIG. 4B) in serum isolated from the mice of FIG. 3.
Figure 4B:
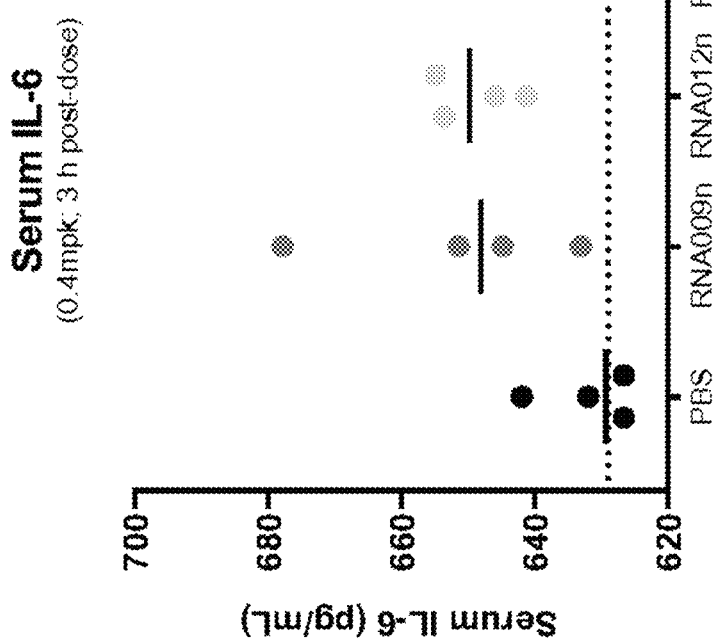

Additionally, tolerability was evaluated by measuring serum cytokine induction following administration of RNA-LNP as described in Example 2. Serum was collected at 3 hours post-administration of co-formulated RNA-LNP. As shown in FIGS. 4A-4B, both IL-6 and MCP-1 levels were comparable for each of the mRNAs evaluated.

These data indicated that the editing efficiency and tolerability of RNA-009n was not further improved with use of a uridine-depleted mRNA, such as that present in RNA-012n or RNA-013n.

Example 5: Effect of mRNA Dose on Gene Editing in Mice

The effect of mRNA dose on editing efficiency of various gene targets was further evaluated for RNA-009n using sgRNA targeting the albumin, C3, or transferrin loci. The RNA-009n transcript was prepared, as described in Example 1, and co-formulated with the sgRNA as LNPs, as described in Example 2. Co-formulated mRNA-LNP was administered by intravenous tail vein injection at a dose of 1.0 mpk, 0.6 mpk, 0.4 mpk, 0.3 mpk, 0.25 mpk, or 0.2 mpk to C57BL/6 mice. Negative control mice received an intravenous injection of PBS alone.

Editing efficiency was determined by measuring INDEL frequency at the albumin (FIG. 5A), C3 (FIG. 5B), and transferrin (FIG. 5C) loci in liver tissue, as described in Example 2. Liver tissue was isolated at approximately 96 hours post-administration of co-formulated RNA-LNP.

Figure 5A:
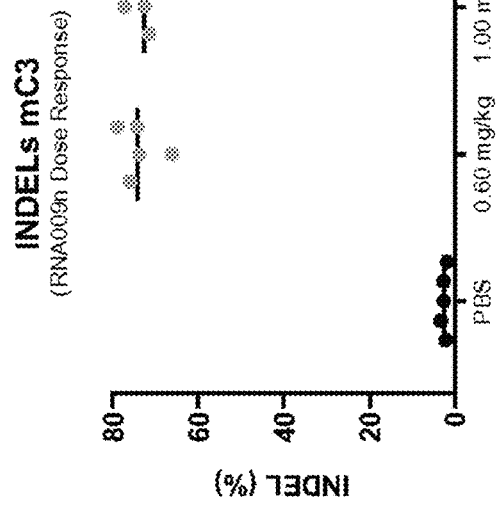
FIGS. 5A-5C provides a graph showing frequency of INDELs in liver tissue of mice administered with various dose levels of LNPs containing RNA-009n mRNA and sgRNA targeting the albumin (FIG. 5A), C3 (FIG. 5B), or transferrin (FIG. 5C) loci.
Figure 5C:
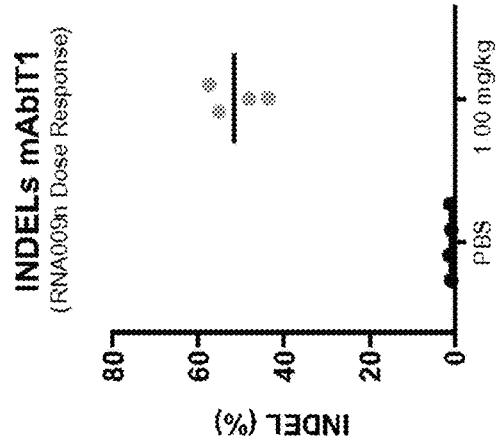
Figure 5B:
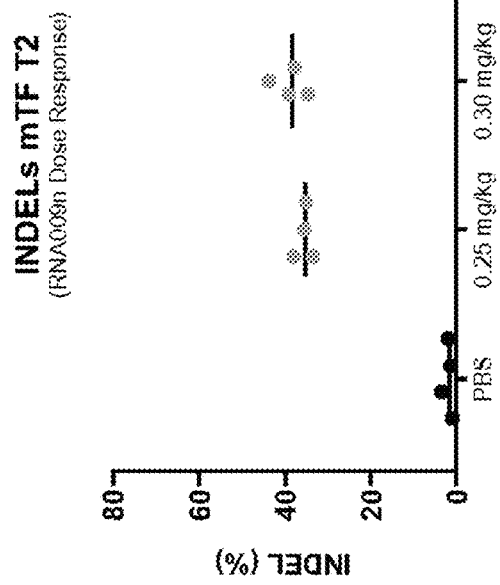

FIG. 5A shows editing efficiency for RNA-009n was high for the 1.0 mpk dose with the frequency of INDELs at the albumin target gene exceeding 40%. As shown in FIG. 5B, editing efficiency for RNA-009n was high for the 1.0 mpk dose and the 0.6 mpk dose, with the frequency of INDELs at the C3 target gene exceeding 70% at each dose. Furthermore, as shown in FIG. 5C, the frequency of INDELs at the transferrin target gene was above 35% for the 0.4 mpk, 0.3 mpk, and 0.25 mpk doses. Together, these data indicate efficient gene editing with RNA-009n.

Figure 6:
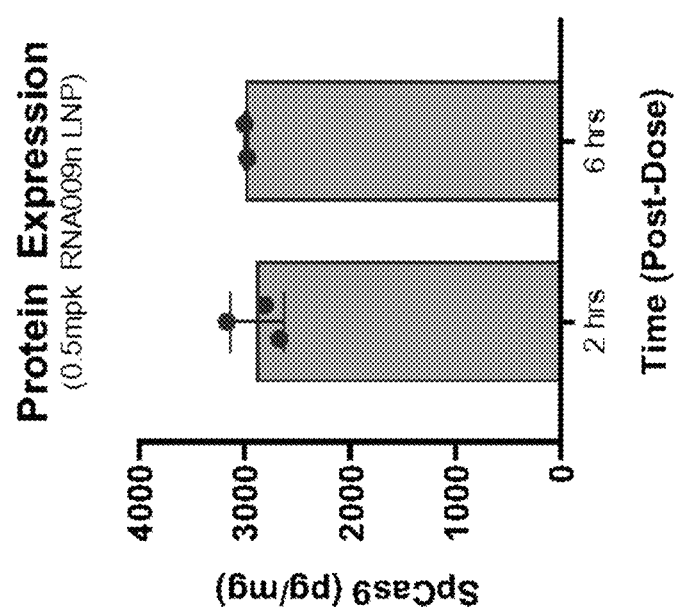
FIG. 6 provides a graph quantifying SpCas9 protein in liver tissue of mice administered LNP containing RNA-009n mRNA. Quantification is shown as pg of SpCas9 per mg of tissue (pg/mg) for 2 and 6 hours following LNP administration.

Furthermore, levels of Cas9 protein produced in liver tissue following administration of RNA-009n was evaluated. RNA-009n was formulated as an LNP preparation without gRNA. The RNA-LNP was administered by intravenous tail vein injection at a dose of 0.5 mg RNA-009n per kg of body weight to C57BL/6 mice. Liver tissue was isolated at 2 hours and 6 hours post administration. The liver tissue was homogenized and the quantity of SpCas9 present per mg of liver tissue was determined by electrochemiluminescence immunoassay. As shown in FIG. 6, SpCas9 levels exceeded 2000 pg/mg at each time point evaluated.

Example 6: Evaluation of Optimized mRNA for Gene Editing in Non-Human Primates In vivo editing efficiency and tolerability of sequence optimized SpCas9 RNA-009 with N1-methylpseudouridine modification was further evaluated in non-human primate (NHPs). The SpCas9 RNA-009n transcripts were compared to unmodified RNA-012 (RNA-012u) or RNA-012 with N1-methylspeurouridine modification (RNA-012n). The RNA-009n, RNA-012u, and RNA-012n transcripts were prepared as described in Example 1.

The mRNA transcripts were evaluated for editing of a target gene sequence in the albumin gene locus. The SpCas9 mRNA and a sgRNA targeting the NHP albumin locus (hT5) were co-formulated as LNPs as described in Example 2. The NHPs were administered the co-formulated RNA-LNP by intravenous injection at a dose of 2 mg RNA (mRNA +gRNA) per kg of body weight (mg/kg).

To evaluate editing efficiency, liver tissue was isolated at 7 days post administration of RNA-LNP. Genomic DNA was extracted, the albumin target gene was amplified by PCR, and INDEL frequency was determined by TIDE analysis as described in Example 2.

Figure 7:
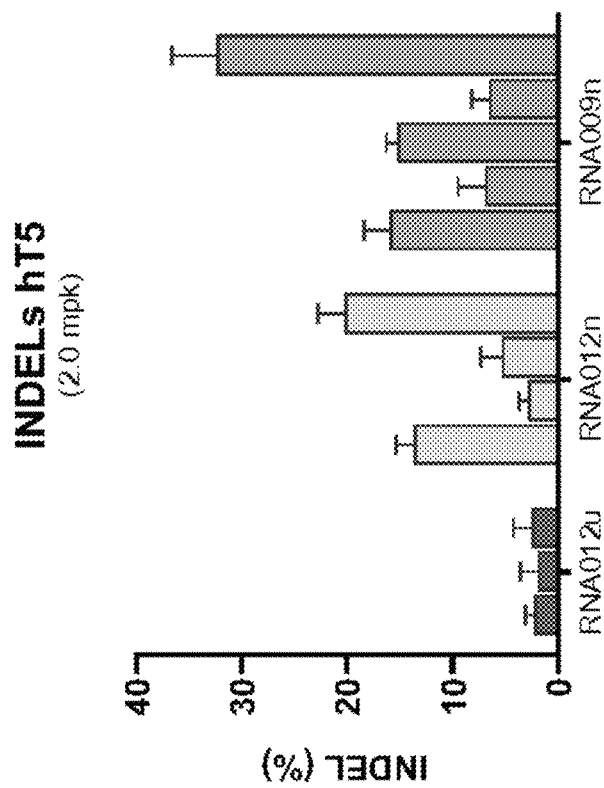
FIG. 7 provides a graph showing frequency of INDELs in liver tissue of non-human primates (NHPs) administered LNPs containing sgRNA targeting NHP albumin gene target (hT5) and SpCas9 mRNA that was RNA-012 with unmodified uracil (RNA-012u), RNA-012n, or RNA-009n.

As shown in FIG. 7, administration of co-formulated RNA-LNP containing RNA-009n resulted in higher editing efficiency compared to RNA-LNP containing RNA-012u. The average INDEL frequency is shown in Table 8.

TABLE 8

In Vivo Editing Efficiency of Albumin Gene Locus in NHPs

| mRNA | # NHP per cohort | Average INDEL frequency (%) |
|---|---|---|
| RNA-012u | 3 | 2.2 ± 0.3 |
| RNA-012n | 4 | 10.5 ± 8.0 |
| RNA-009n | 5 | 15.4 ± 10.5 |

SEQUENCE LISTING

| Name/Description | Type | Sequence | SEQ ID NO |
|---|---|---|---|
| RNA-009 | DNA | AGAGGAAATAAGAGAGAAAAGAAGAGTAAGAAGAAATATAAGAGCCA CCATGGCCCCTAAGAAGAAGAGAAAAGTCGGAATTCACGGAGTCCCC GCCGCCGACAAAAAGTACTCCATTGGCCTTGATATTGGAACCAACTC CGTGGGTTGGGCCGTGATCACTGACGAGTACAAGGTGCCGTCCAAGA AGTTCAAGGTGCTGGGGAACACTGACCGGCACTCAATTAAGAAGAAC CTGATTGGGGCGCTGCTGTTCGACTCCGGAGAAACCGCGGAGGCTAC CCGCCTGAAGCGGACTGCCCGGCGGAGATACACGCGCAGGAAGAACC GGATTTGCTACCTCCAAGAAATCTTCAGCAACGAAATGGCAAAGGTG GACGATTCCTTCTTCCATCGCCTGGAAGAGAGCTTCCTGGTGGAAGA GGACAAGAAGCACGAAAGACACCCGATTTTCGGCAACATCGTGGATG AGGTCGCATACCACGAAAAGTACCCCACCATCTATCATCTTCGGAAG AAGCTGGTCGACTCCACCGATAAGGCCGATCTGCGCCTGATCTACTT GGCGCTGGCTCACATGATTAAGTTCAGAGGACACTTTCTGATAGAGG GCGACCTCAATCCCGATAACTCCGACGTGGATAAGCTGTTCATCCAA CTGGTGCAGACGTACAACCAACTGTTTGAAGAGAATCCAATCAACGC CAGCGGGGTGGACGCCAAGGCCATCCTGTCCGCCCGGCTGTCAAAGT CCAGACGCCTGGAGAATCTCATCGCGCAACTCCCTGGCGAAAAAAAG AACGGACTCTTCGGGAATCTGATTGCTCTGTCCCTGGGGCTCACTCC GAACTTCAAGTCGAACTTCGACCTGGCGGAGGACGCTAAGCTGCAGC TGTCCAAGGACACCTACGATGACGATCTGGATAACCTTCTGGCCCAG ATCGGGGATCAATCAGCCGATCTCTTCCTGGCCGCAAAGAACTTGTC GGATGCTATTCTGCTGAGCGACATTCTGCGGGTCAATACTGAAATCA CCAAGGCGCCCCTGTCGGCCAGCATGATCAAGCGCTACGACGAACAC CACCAAGACCTGACTCTGCTGAAGGCCCTCGTGCGCCAGCAGCTGCC TGAAAAGTACAAGGAGATTTTCTTCGACCAGTCCAAGAACGGATACG CCGGATACATTGACGGAGGGGCCAGCCAGGAGGAATTTTACAAATTC ATCAAGCCCATTCTCGAGAAAATGGACGGAACCGAAGAGTTGCTCGT GAAGCTGAACAGAGAGGATCTCCTCCGGAAGCAGCGGACCTTCGACA ACGGTTCCATCCCGCACCAAATCCACCTGGGCGAATTGCACGCCATC CTCCGGCGGCAGGAAGATTTCTACCCATTCTTGAAGGACAATCGCGA AAAGATCGAAAAGATCTTGACTTTCCGCATCCCGTACTACGTGGGCC CTCTGGCCCGCGGCAACTCCCGCTTCGCTTGGATGACACGGAAGTCC GAGGGAAACCATTACGCCCTGGAACTTCGAGGGAAGTGGTGGACAAGGG GGCGTCCGCCCAGAGCTTCATCGAACGCATGACCAATTTCGACAAGA ACCTCCCGAACGAAAAAGTGCTGCCAAAGCACTCGCTCCTCTACGAA TACTTCACCGTGTACAACGAGCTGACTAAGGTCAAATACGTGACTGA GGGAATGCGGAAGCCGGCCTTCCTGTCGGGAGAGCAGAAGAAGGCCA TAGTGGACTTGCTTTTCAAGACTAACCGGAAGGTCACTGTGAAGCAA CTCAAGGAGGACTACTTCAAGAAGATCGAGTGTTTCGACTCGGTGGA GATCTCGGGTGTCGAGGACCGCTTCAACGCCTCCCTGGGAACTTACC ACGATCTGCTGAAGATCATCAAGGACAAGGACTTCCTCGATAACGAA GAAAATGAGGACATCCTCGAGGATATCGTGCTGACCCTGACCTTGTT CGAGGATAGGGAGATGATCGAGGAGCGGCTCAAGACCTACGCCCACC TGTTTGACGACAAAGTGATGAAGCAACTGAAACGGCGGAGGTATACC GGCTGGGGTCGGCTGTCCCGCAAGCTGATCAACGGGATCAGGGACAA GCAGTCCGGAAAGACCATCCTCGACTTCCTTAAGTCCGACGGATTCG CGAACCGCAACTTCATGCAACTTATCCACGACGACTCGCTGACATTC AAGGAAGATATCCAGAAGGCCCAGGTGTCCGGACAGGGGGACTCGCT TCATGAGCACATCGCTAACCTGGCCGGATCCCCCGCCATAAAAAAGG GCATTCTGCAGACCGTCAAAGTGGTGGATGAGCTGGTCAAGGTCATG | 1 |

| Name/Description | Type | Sequence | SEQ ID NO |
|---|---|---|---|
| | | GGCCGGCATAAGCCGGAAAACATCGTCATCGAGATGGCCCGCGAGAA<br>CCAGACTACGCAGAAGGGCCAGAAGAACTCCCGGGAGCGGATGAAGC<br>GGATTGAAGAGGGCATCAAGGAGCTCGGCAGCCAGATTCTGAAGGAA<br>CATCCCGTGGAAAACACCCAGCTGCAAAACGAAAAGCTCTATTTGTA<br>CTATCTGCAAAACGGACGCGATATGTACGTGGATCAGGAGCTGGACA<br>TTAACAGACTGAGCGACTATGACGTGGATCACATTGTGCCTCAAAGC<br>TTCCTCAAGGACGACTCAATTGACAACAAGGTCCTGACCAGAAGCGA<br>CAAGAACAGAGGAAAGTCGGATAATGTGCCGTCCAAGAAGTGGTCA<br>AGAAGATGAAGAATTACTGGAGACAGCTCCTGAATGCGAAGCTCATT<br>ACCCAGCGGAAGTTCGATAACCTGACCAAGGCCGAAAGGGGTGGACT<br>GTCCGAACTCGACAAAGCTGGCTTCATCAAGCGCCAACTGGTCGAAA<br>CCAGGCAGATCACCAAGCACGTCGCCCAGATTCTGGACAGCCGCATG<br>AACACTAAGTACGACGAGAACGATAAGCTGATCCGCGAAGTGAAGGT<br>CATCACCCTGAAGTCCAAGCTCGTGTCCGACTTTCGGAAGGATTTCC<br>AGTTTTACAAGGTCCGCGAGATCAACAACTACCATCACGCCCACGAC<br>GCGTACCTTAACGCAGTCGTGGGAACGGCTCTTATCAAGAAGTACCC<br>AAAGCTGGAGTCGGAATTTGTGTACGGAGACTACAAAGTGTACGACG<br>TGCGCAAGATGATCGCCAAATCTGAGCAAGAGATCGGGAAGGCAACC<br>GCCAAATACTTCTTCTACTCAAACATTATGAATTTTTTCAAAACTGA<br>GATTACCCTGGCTAACGGAGAAATTCGGAAGCGCCCCCTGATTGAAA<br>CCAACGGAGAAACTGGAGAAATTGTGTGGGACAAGGGACGGGACTTC<br>GCCACCGTCCGCAAGGTCCTCTCAATGCCCCAAGTCAACATCGTGAA<br>AAAGACCGAAGTGCAAACCGGCGGCTTCTCAAAGGAGTCCATCCTGC<br>CTAAGCGCAACAGCGACAAGCTGATTGCCAGGAAGAAGGACTGGGAC<br>CCGAAGAAGTACGGAGGATTTGATTCCCCTACCGTGGCCTACTCCGT<br>GCTCGTGGTGGCCAAAGTGGAAAAGGGGAAATCCAAGAAGCTGAAGT<br>CGGTGAAGGAGCTTTTGGGTATCACCATCATGGAACGCTCCTCGTTC<br>GAAAAGAACCCAATCGATTTCCTGGAAGCTAAGGGTTATAAGGAAGT<br>GAAAAAGGACCTGATTATCAAGCTGCCCAAGTACTCACTGTTCGAGC<br>TGGAAAACGGTCGGAAAAGGATGCTGGCCAGCGCCGGAGAACTCCAG<br>AAGGGAAACGAACTGGCACTGCCGTCCAAATACGTCAACTTCCTCTA<br>CCTTGCATCCCATTACGAAAAACTCAAGGGATCGCCGGAGGACAACG<br>AGCAGAAGCAGCTTTTCGTGGAGCAACACAAGCATTACTTGGACGAG<br>ATCATCGAGCAGATTTCCGAGTTCTCAAAGCGCGTGATCCTGGCCGA<br>CGCAAATCTGGACAAGGTCCTGTCCGCGTACAATAAGCATCGGGACA<br>AGCCTATCCGCGAACAGGCCGAGAACATCATCCATCTGTTCACTCTG<br>ACAAACCTGGGCGCACCCGCCGCGTTCAAGTACTTTGACACCACCAT<br>CGATAGGAAGCGATACACCTCAACTAAGGAAGTGTTGGACGCGACCC<br>TTATCCATCAGTCGATCACCGGGCTGTACGAAACACGGATCGACCTC<br>AGCCAGTTGGGAGGCGACAAGCGCCCTGCGGCTACCAAGAAGGCCGG<br>ACAGGCCAAGAAGAAGAAATGAGCGGCCGCTTAATTAAGCTGCCTTC<br>TGCGGGGCTTGCCTTCTGGCCATGCCCTTCTTCTCTCCCTTGCACCT<br>GTACCTCTTGGTCTTTGAATAAAGCCTGAGTAGGAAGTCTAGAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAA | |
| RNA-009<br>Full-length<br>mRNA<br>5' UTR IN<br>BOLD<br>3' UTR IN<br>BOLD ITALICS<br>POLY-A TAIL<br>IN UNDERLINE | RNA | AGAGGAAAUAAGAGAGAAAAGAAGAGUAAGAAGAAAUAUAAGAGCCA<br>CCAUGGCCCCUAAGAAGAAGAGAAAAGUCGGAAUUCACGGAGUCCCC<br>GCCGCCGACAAAAAGUACUCCAUUGGCCUUGAUAUUGGAACCAACUC<br>CGUGGGUUGGGCCGUGAUCACUGACGAGUACAAGGUGCCGUCCAAGA<br>AGUUCAAGGUGCUGGGGAACACUGACCGGCACUCAAUUAAGAAGAAC<br>CUGAUUGGGGCGCUGCUGUUCGACUCCGGAGAAACCGCGGAGGCUAC<br>CCGCCUGAAGCGGACUGCCCGGCGGAGAUACACGCGCAGGAAGAACC<br>GGAUUUGCUACCUCCAAGAAAUCUUCAGCAACGAAAUGGCAAAGGUG<br>GACGAUUCCUUCUUCCAUCGCCUGGAAGAGAGCUUCCUGGUGGAGA<br>GGACAAGAAGCACGAAAGACACCCGAUUUUCGGCAACAUCGUGGAUG<br>AGGUCGCAUACCACGAAAAGUACCCCACCAUCUAUCAUCUUCGGAAG<br>AAGCUGGUCGACUCCACCGAUAAGGCCGAUCUGCGCCUGAUCUACUU<br>GGCGCUGGCUCACAUGAUUAAGUUCAGAGGACACUUUCUGAUAGAGG<br>GCGACCUCAAUCCCGAUAACUCCGACGUGGAUAAGCUGUUCAUCCAA<br>CUGGUGCAGACGUACAACCAACUGUUUGAAGAGAAUCCAAUCAACGC<br>CAGCGGGGUGGACGCCAAGGCCAUCCUGUCCGCCCGGCUGUCAAAGU<br>CCAGACGCCUGGAGAAUCUCAUCGCGCAACUCCCUGGCGAAAAAAG<br>AACGGACUCUUCGGGAAUCUGAUUGCUCUGUCCCUGGGGCUCACUCC<br>GAACUUCAAGUCGAACUUCGACCUGGCGGAGGACGCUAAGCUGCAGC<br>UGUCCAAGGACACCUACGAUGACGAUCUGGAUAACCUUCUGGCCCAG<br>AUCGGGGAUCAAUACGCCGAUCUCUUCCUGGCCGCAAAGAACUUGUC<br>GGAUGCUAUUCUGCUGAGCGACAUUCUGCGGGUCAAUACUGAAAUCA<br>CCAAGGCGCCCCUGUCCGCAAGCAUGAUCAAGCGCUACGACGAACAC<br>CACCAAGACCUGACUCUGCUGAAGGCCCUCGUGCGCCAGCAGCUGCC<br>UGAAAAGUACAAGGAGAUUUUCUUCGACCAGUCCAAGAACGGAUACG<br>CCGGAUACAUUGACGGAGGGGCCAGCCAGGAGGAAUUUUACAAAUUC<br>AUCAAGCCCAUUCUCGAGAAAAUGGACGGAACCGAAGAGUUGCUCGU<br>GAAGCUGAACAGAGAGGAUCUCCUCCGGAAGCAGCGGACCUUCGACA<br>ACGGUUCCAUCCCGCACCAAAUCCACCUGGGCGAAUUGCACGCCAUC** | 2 |

| Name/Description | Type | Sequence | SEQ ID NO |
|---|---|---|---|
| | | CUCCGGCGGCAGGAAGAUUUCUACCCAUUCUUGAAGGACAAUCGCGA<br>AAAGAUCGAAAAGAUCUUGACUUUCCGCAUCCCGUACUACGUGGGCC<br>CUCUGGCCCGCGGCAACUCCCGCUUCGCUUGGAUGACACGGAAGUCC<br>GAGGAAACCAUUACGCCCUGGAACUUCGAGGAAGUGGUGGACAAGGG<br>GGCGUCCGCCCAGAGCUUCAUCGAACGCAUGACCAAUUUCGACAAGA<br>ACCUCCCGAACGAAAAGUGCUGCCAAAGCACUCGCUCCUCUACGAA<br>UACUUCACCGUGUACAACGAGCUGACUAAGGUCAAAUACGUGACUGA<br>GGGAAUGCGGAAGCCGGCCUUCCUGUCGGGAGAGCAGAAGAAGGCCA<br>UAGUGGACUUGCUUUUCAAGACUAACCGGAAGGUCACUGUGAAGCAA<br>CUCAAGGAGGACUACUUCAAGAAGAUCGAGUGUUUCGACUCGGUGGA<br>GAUCUCGGGUGUCGAGGACCGCUUCAACGCCUCCCUGGGAACUUACC<br>ACGAUCUGCUGAAGAUCAUCAAGGACAAGGACUUCCUCGAUAACGAA<br>GAAAAUGAGGACAUCCUCGAGGAUAUCGUGCUGACCCUGACCUUGUU<br>CGAGGAUAGGGAGAUGAUCGAGGAGCGGCUCAAGACCUACGCCCACC<br>UGUUUGACGACAAAGUGAUGAAGCAACUGAAACGGCGGAGGUAUACC<br>GGCUGGGGUCGGCUGUCCCGCAAGCUGAUCAACGGGAUCAGGGACAA<br>GCAGUCCGGAAAGACCAUCCUCGACUUCCUUAAGUCCGACGGAUUCG<br>CGAACCGCAACUUCAUGCAACUUAUCCACGACGACUCGCUGACAUUC<br>AAGGAAGAUAUCCAGAAGGCCCAGGUGUCCGGACAGGGGGACUCGCU<br>UCAUGAGCACAUCGCUAACCUGGCCGGAUCCCCCGCCAUAAAAAAGG<br>GCAUUCUGCAGACCGUCAAAGUGGUGGAUGAGCUGGUCAAGGUCAUG<br>GGCCGGCAUAAGCCGGAAAACAUCGUCAUCGAGAUGGCCCGCGAGAA<br>CCAGACUACGCAGAAGGGCCAGAAGAACUCCCGGGAGCGGAUGAAGC<br>GGAUUGAAGAGGGCAUCAAGGAGCUCGGCAGCCAGAUUCUGAAGGAA<br>CAUCCCGUGGAAAACACCCAGCUGCAAAACGAAAAGCUCUAUUUGUA<br>CUAUCUGCAAAACGGACGCGAUAUGUACGUGGAUCAGGAGCUGGACA<br>UUAACAGACUGAGCGACUAUGACGUGGAUCACAUUGUGCCUCAAAGC<br>UUCCUCAAGGACGACUCAAUUGACAACAAGGUCCUGACCAGAAGCGA<br>CAAGAACAGAGGGAAAGUCGGAUAAUGUGCCGUCCGAAGAAGUGGUCA<br>AGAAGAUGAAGAAUUACUGGAGACAGCUCCUGAAUGCGAAGCUCAUU<br>ACCCAGCGGAAGUUCGAUAACCUGACCAAGGCCGAAAGGGGUGGACU<br>GUCCGAACUCGACAAAGCUGGCUUCAUCAAGCGCCAACUGGUCGAAA<br>CCAGGCAGAUCACCAAGCACGUCGCCCAGAUUCUGGACAGCCGCAUG<br>AACACUAAGUACGACGAGAACGAUAAGCUGAUCCGCGAAGUGAAGGU<br>CAUCACCCUGAAGUCCAAGCUCGUGUCCGACUUUCGGAAGGAUUUCC<br>AGUUUUACAAGGUCCGCGAGAUCAACAACUACCAUCACGCCCACGAC<br>GCGUACCUUAACGCAGUCGUGGGAACGGCUCUUAUCAAGAAGUACCC<br>AAAGCUGGAGUCGGAAUUUGUGUACGGAGACUACAAAGUGUACGACG<br>UGCGCAAGAUGAUCGCCAAAUCUGAGCAAGAGAUCGGGAAGGCAACC<br>GCCAAAUACUUCUUCUACUCAAACAUUAUGAAUUUUUCAAACUGA<br>GAUUACCCUGGCUAACGGAGAAAUUCGGAAGCGCCCCCUGAUUGAAA<br>CCAACGGAGAAACUGGAGAAAUUGUGUGGGACAAGGGACGGGACUUC<br>GCCACCGUCCGCAAGGUCCUCUCAAUGCCCCAAGUCAACAUCGUGAA<br>AAAGACCGAAGUGCAAACCGGCGGCUUCUCAAAGGAGUCCAUCCUGC<br>CUAAGCGCAACAGCGACAAGCUGAUUGCCAGGAAGAAGGACUGGGAC<br>CCGAAGAAGUACGGAGGAUUUGAUUCCCCUACCGUGGCCUACUCCGU<br>GCUCGUGGUGGCCAAAGUGGAAAAGGGGAAAUCCAAGAAGCUGAAGU<br>CGGUGAAGGAGCUUUUGGGUAUCACCAUCAUGGAACGCUCCUCGUUC<br>GAAAAGAACCCAAUCGAUUUCCUGGAAGCUAAGGGUUAUAAGGAAGU<br>GAAAAAGGACCUGAUUAUCAAGCUGCCAAGUACUCACUGUUCGAGC<br>UGGAAAACGGUCGGAAAGGAUGCUGGCCAGCGCCGGAGAACUCCAG<br>AAGGGAAACGAACUGGCACUGCCGUCCAAAUACGUCAACUUCCUCUA<br>CCUUGCAUCCCAUUACGAAAAACUCAAGGGAUCGCCGGAGGACAACG<br>AGCAGAAGCAGCUUUUCGUGGAGCAACACAAGCAUUACUUGGACGAG<br>AUCAUCGAGCAGAUUCCGAGUUCUCAAAGCGCGUGAUCCUGGCCGA<br>CGCAAAUCUGGACAAGGUCCUGUCCGCGUACAAUAAGCAUCGGGACA<br>AGCCUAUCCGCGAACAGGCCGAGAACAUCAUCCAUCUGUUCACUCUG<br>ACAAACCUGGGCGCACCCGCCGCGUUCAAGUACUUUGACACCACCAU<br>CGAUAGGAAGCGAUACACCUCAACUAAGGAAGUGUUGGACGCGACCC<br>UUAUCCAUCAGUCGAUCACCGGGCUGUACGAAACACGGAUCGACCUC<br>AGCCAGUUGGGAGGCGACAAGCGCCCUGCGGCUACCAAGAAGGCCGG<br>ACAGGCCAAGAAGAAGAAAUGA*GCGGCCGCUUAAUUAAGCUGCCUUC<br>UGCGGGGCUUGCCUUCUGGCCAUGCCCUUCUUCUCUCCCUUGCACCU<br>GUACCUCUUGGUCUUUGAAUAAAGCCUGAGUAGGAAGUCUAG*<u>AAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAA</u> | |
| RNA-009<br>coding region | DNA | ATGGCCCCTAAGAAGAAGAGAAAAGTCGGAATTCACGGAGTCCCCGC<br>CGCCGACAAAAAGTACTCCATTGGCCTTGATATTGGAACCAACTCCG<br>TGGGTTGGGCCGTGATCACTGACGAGTACAAGGTGCCGTCCAAGAAG<br>TTCAAGGTGCTGGGGAACACTGACCGGCACTCAATTAAGAAGAACCT<br>GATTGGGGCGCTGCTGTTCGACTCCGGAGAAACCGCGAGGCTACCC<br>GCCTGAAGCGGACTGCCCGGCGGAGATACACGCGCAGGAAGAACCGG<br>ATTTGCTACCTCCAAGAAATCTTCAGCAACGAAATGGCAAAGGTGGA<br>CGATTCCTTCTTCCATCGCCTGGAAGAGAGCTTCCTGGTGGAAGAGG | 3 |

| Name/ Description | Type | Sequence | SEQ ID NO |
|---|---|---|---|
| | | ACAAGAAGCACGAAAGACACCCGATTTTCGGCAACATCGTGGATGAG | |
| | | GTCGCATACCACGAAAAGTACCCCACCATCTATCATCTTCGGAAGAA | |
| | | GCTGGTCGACTCCACCGATAAGGCCGATCTGCGCCTGATCTACTTGG | |
| | | CGCTGGCTCACATGATTAAGTTCAGAGGACACTTTCTGATAGAGGGC | |
| | | GACCTCAATCCCGATAACTCCGACGTGGATAAGCTGTTCATCCAACT | |
| | | GGTGCAGACGTACAACCAACTGTTTGAAGAGAATCCAATCAACGCCA | |
| | | GCGGGGTGGACGCCAAGGCCATCCTGTCCGCCCGGCTGTCAAAGTCC | |
| | | AGACGCCTGGAGAATCTCATCGCGCAACTCCCTGGCGAAAAAAGAA | |
| | | CGGACTCTTCGGGAATCTGATTGCTCTGTCCCTGGGGCTCACTCCGA | |
| | | ACTTCAAGTCGAACTTCGACCTGGCGGAGGACGCTAAGCTGCAGCTG | |
| | | TCCAAGGACACCTACGATGACGATCTGGATAACCTTCTGGCCCAGAT | |
| | | CGGGGATCAATACGCCGATCTCTTCCTGGCCGAAAGAACTTGTCGG | |
| | | ATGCTATTCTGCTGAGCGACATTCTGCGGGTCAATACTGAAATCACC | |
| | | AAGGCGCCCCTGTCGGCCAGCATGATCAAGCGCTACGACGAACACCA | |
| | | CCAAGACCTGACTCTGCTGAAGGCCCTCGTGCGCCAGCAGCTGCCTG | |
| | | AAAAGTACAAGGAGATTTTCTTCGACCAGTCCAAGAACGGATACGCC | |
| | | GGATACATTGACGGAGGGGCCAGCCAGGAGGAATTTTACAAATTCAT | |
| | | CAAGCCCATTCTCGAGAAAATGGACGGAACCGAAGAGTTGCTCGTGA | |
| | | AGCTGAACAGAGAGGATCTCCTCCGGAAGCAGCGGACCTTCGACAAC | |
| | | GGTTCCATCCCGCACCAAATCCACCTGGGCGAATTGCACGCCATCCT | |
| | | CCGGCGGCAGGAAGATTTCTACCCATTCTTGAAGGACAATCGCGAAA | |
| | | AGATCGAAAAGATCTTGACTTTCCGCATCCCGTACTACGTGGGCCCT | |
| | | CTGGCCCGCGGCAACTCCCGCTTCGCTTGGATGACACGGAAGTCCGA | |
| | | GGAAACCATTACGCCCTGGAACTTCGAGGAAGTGGTGGACAAGGGGG | |
| | | CGTCCGCCCAGAGCTTCATCGAACGCATGACCAATTTCGACAAGAAC | |
| | | CTCCCGAACGAAAAGTGCTGCCAAAGCACTCGCTCCTCTACGAATA | |
| | | CTTCACCGTGTACAACGAGCTGACTAAGGTCAAATACGTGACTGAGG | |
| | | GAATGCGGAAGCCGGCCTTCCTGTCGGGAGAGCAGAAGAAGGCCATA | |
| | | GTGGACTTGCTTTTCAAGACTAACCGGAAGGTCACTGTGAAGCAACT | |
| | | CAAGGAGGACTACTTCAAGAAGATCGAGTGTTTCGACTCGGTGGAGA | |
| | | TCTCGGGTGTCGAGGACCGCTTCAACGCCTCCCTGGGAACTTACCAC | |
| | | GATCTGCTGAAGATCATCAAGGACAAGGACTTCCTCGATAACGAAGA | |
| | | AAATGAGGACATCCTCGAGGATATCGTGCTGACCCTGACCTTGTTCG | |
| | | AGGATAGGGAGATGATCGAGGAGCGGCTCAAGACCTACGCCCACCTG | |
| | | TTTGACGACAAAGTGATGAAGCAACTGAAACGGCGGAGGTATACCGG | |
| | | CTGGGGTCGGCTGTCCCGCAAGCTGATCAACGGGATCAGGGACAAGC | |
| | | AGTCCGGAAAGACCATCCTCGACTTCCTTAAGTCCGACGGATTCGCG | |
| | | AACCGCAACTTCATGCAACTTATCCACGACGACTCGCTGACATTCAA | |
| | | GGAAGATATCCAGAAGGCCCAGGTGTCCGGACAGGGGGACTCGCTTC | |
| | | ATGAGCACATCGCTAACCTGGCCGGATCCCCCGCCATAAAAAAGGGC | |
| | | ATTCTGCAGACCGTCAAAGTGGTGGATGAGCTGGTCAAGGTCATGGG | |
| | | CCGGCATAAGCCGGAAAACATCGTCATCGAGATGGCCCGCGAGAACC | |
| | | AGACTACGCAGAAGGGCCAGAAGAACTCCCGGGAGCGGATGAAGCGG | |
| | | ATTGAAGAGGGCATCAAGGAGCTCGGCAGCCAGATTCTGAAGGAACA | |
| | | TCCCGTGGAAAACACCCAGCTGCAAAACGAAAAGCTCTATTTGTACT | |
| | | ATCTGCAAAACGGACGCGATATGTACGTGGATCAGGAGCTGGACATT | |
| | | AACAGACTGAGCGACTATGACGTGGATCACATTGTGCCTCAAAGCTT | |
| | | CCTCAAGGACGACTCAATTGACAACAAGGTCCTGACCAGAAGCGACA | |
| | | AGAACAGAGGAAAGTCGGATAATGTGCCGTCCGAAGAAGTGGTCAAG | |
| | | AAGATGAAGAATTACTGGAGACAGCTCCTGAATGCGAAGCTCATTAC | |
| | | CCAGCGGAAGTTCGATAACCTGACCAAGGCCGAAAGGGGTGGACTGT | |
| | | CCGAACTCGACAAAGCTGGCTTCATCAAGCGCCAACTGGTCGAAACC | |
| | | AGGCAGATCACCAAGCACGTCGCCCAGATTCTGGACAGCCGCATGAA | |
| | | CACTAAGTACGACGAGAACGATAAGCTGATCCGCGAAGTGAAGGTCA | |
| | | TCACCCTGAAGTCCAAGCTCGTGTCCGACTTTCGGAAGGATTTCCAG | |
| | | TTTTACAAGGTCCGCGAGATCAACAACTACCATCACGCCCACGACGC | |
| | | GTACCTTAACGCAGTCGTGGGAACGGCTCTTATCAAGAAGTACCCAA | |
| | | AGCTGGAGTCGGAATTTGTGTACGGAGACTACAAAGTGTACGACGTG | |
| | | CGCAAGATGATCGCCAAATCTGAGCAAGAGATCGGGAAGGCAACCGC | |
| | | CAAATACTTCTTCTACTCAAACATTATGAATTTTTTCAAAACTGAGA | |
| | | TTACCCTGGCTAACGGAGAAATTCGGAAGCGCCCCCTGATTGAAACC | |
| | | AACGGAGAAACTGGAGAAATTGTGTGGGACAAGGGACGGGACTTCGC | |
| | | CACCGTCCGCAAGGTCCTCTCAATGCCCCAAGTCAACATCGTGAAAA | |
| | | AGACCGAAGTGCAAACCGGCGGCTTCTCAAAGGAGTCCATCCTGCCT | |
| | | AAGCGCAACAGCGACAAGCTGATTGCCAGGAAGAAGGACTGGGACCC | |
| | | GAAGAAGTACGGAGGATTTGATTCCCCTACCGTGGCCTACTCCGTGC | |
| | | TCGTGGTGGCCAAAGTGGAAAAGGGGAAATCCAAGAAGCTGAAGTCG | |
| | | GTGAAGGAGCTTTTGGGTATCACCATCATGGAACGCTCCTCGTTCGA | |
| | | AAAGAACCCAATCGATTTCCTGGAAGCTAAGGGTTATAAGGAAGTGA | |
| | | AAAAGGACCTGATTATCAAGCTGCCCAAGTACTCACTGTTCGAGCTG | |
| | | GAAAACGGTCGGAAAAGGATGCTGGCCAGCGCCGGAGAACTCCAGAA | |
| | | GGGAAACGAACTGGCACTGCCGTCCAAATACGTCAACTTCCTCTACC | |
| | | TTGCATCCCATTACGAAAAACTCAAGGGATCGCCGGAGGACAACGAG | |
| | | CAGAAGCAGCTTTTCGTGGAGCAACACAAGCATTACTTGGACGAGAT | |
| | | CATCGAGCAGATTTCCGAGTTCTCAAAGCGCGTGATCCTGGCCGACG | |
| | | CAAATCTGGACAAGGTCCTGTCCGCGTACAATAAGCATCGGGACAAG | |

| Name/<br>Description | Type | Sequence | SEQ ID NO |
|---|---|---|---|
| | | CCTATCCGCGAACAGGCCGAGAACATCATCCATCTGTTCACTCTGAC<br>AAACCTGGGCGCACCCGCCGCGTTCAAGTACTTTGACACCACCATCG<br>ATAGGAAGCGATACACCTCAACTAAGGAAGTGTTGGACGCGACCCTT<br>ATCCATCAGTCGATCACCGGGCTGTACGAAACACGGATCGACCTCAG<br>CCAGTTGGGAGGCGACAAGCGCCCTGCGGCTACCAAGAAGGCCGGAC<br>AGGCCAAGAAGAAGAAATGA | |
| RNA-009<br>coding region | RNA | AUGGCCCCUAAGAAGAAGAGAAAAGUCGGAAUUCACGGAGUCCCCGC<br>CGCCGACAAAAAGUACUCCAUUGGCCUUGAUAUUGGAACCAACUCCG<br>UGGGUUGGGCCGUGAUCACUGACGAGUACAAGGUGCCGUCCAAGAAG<br>UUCAAGGUGCUGGGGAACACUGACCGGCACUCAAUUAAGAAGAACCU<br>GAUUGGGGCGCUGCUGUUCGACUCCGGAGAAACCGCGGAGGCUACCC<br>GCCUGAAGCGGACUGCCCGGCGGAGAUACACGCGCAGGAAGAACCGG<br>AUUUGCUACCUCCAAGAAAUCUUCAGCAACGAAAUGGCAAAGGUGGA<br>CGAUUCCUUCUUCCAUCGCCUGGAAGAGAGCUUCCUGGUGGAAGAGG<br>ACAAGAAGCACGAAAGACACCCGAUUUUCGGCAACAUCGUGGAUGAG<br>GUCGCAUACCACGAAAAGUACCCCACCAUCUAUCAUCUUCGGAAGAA<br>GCUGGUCGACUCCACCGAUAAGGCCGAUCUGCGCCCUGAUCUACUUGG<br>CGCUGGCUCACAUGAUUAAGUUCAGAGGACACUUUCUGAUAGAGGGC<br>GACCUCAAUCCCGAUAACUCCGACGUGGAUAAGCUGUUCAUCCAACU<br>GGUGCAGACGUACAACCAACUGUUUGAAGAGAAUCCAAUCAACGCCA<br>GCGGGGUGGACGCCAAGGCCAUCCUGUCCGCCCGGCUGUCAAAGUCC<br>AGACGCCUGGAGAAUCUCAUCGCGCAACUCCCUGGCGAAAAAAAGAA<br>CGGACUCUUCGGGAAUCUGAUUGCUCUGUCCCUGGGGCUCACUCCGA<br>ACUUCAAGUCGAACUUCGACCUGGCGGAGGACGCUAAGCUGCAGCUG<br>UCCAAGGACACCUACGAUGACGAUCUGGAUAACCUUCUGGCCCAGAU<br>CGGGGAUCAAUACGCCGAUCUCUUCCUGGCCGCAAAGAACUUGUCGG<br>AUGCUAUUCUGCUGAGCGACAUUCUGCGGGUCAAUACUGAAAUCACC<br>AAGGCGCCCCUGUCGGCCAGCAUGAUCAAGCGCUACGACGAACACCA<br>CCAAGACCUGACUCUGCUGAAGGCCCUCGUGCGCCAGCAGCUGCCUG<br>AAAAGUACAAGGAGAUUUUCUUCGACCAGUCCAAGAACGGAUACGCC<br>GGAUACAUUGACGGAGGGGCCAGCCAGGAGGAAUUUUACAAAUUCAU<br>CAAGCCCAUUCUCGAGAAAAUGGACGGAACCGAAGAGUUGCUCGUGA<br>AGCUGAACAGAGAGGAUCUCCUCCGGAAGCAGCGGACCUUCGACAAC<br>GGUUCAUCCCGCACCAAAUCCACCUGGGCGAAUUGCACGCCAUCCU<br>CCGGCGGCAGGAAGAUUUCUACCCAUUCUUGAAGGACAAUCGCGAAA<br>AGAUCGAAAAGAUCUUGACUUUCCGCAUCCCGUACUACGUGGGCCCU<br>CUGGCCCGCGGCAACUCCCGCUUCGCUUGGAUGACACGGAAGUCCGA<br>GGAAACCAUUACGCCCUGGAACUUCGAGGAAGUGGUGGACAAGGGGG<br>CGUCCGCCCAGAGCUUCAUCGAACGCAUGACCAAUUUCGACAAGAAC<br>CUCCCGAACGAAAAGUGCUGCAAAGCACUCGCUCCCUCUACGAAUA<br>CUUCACCGUGUACAACGAGCUGACUAAGGUCAAAUACGUGACUGAGG<br>GAAUGCGGAAGCCGGCCUUCCUGUCGGGAGAGCAGAAGAAGGCCAUA<br>GUGGACUUGCUUUUCAAGACUAACCGGAAGGUCACUGUGAAGCAACU<br>CAAGGAGGACUACUUCAAGAAGAUCGAGUGUUUCGACUCGGUGGAGA<br>UCUCGGGUGUCGAGGACCGCUUCAACGCCUCCCUGGGAACUUACCAC<br>GAUCUGCUGAAGAUCAUCAAGGACAAGGACUUCCUCGAUAACGAAGA<br>AAAUGAGGACAUCCUCGAGGAUAUCGUGCUGACCCUGACCCUUGUUCG<br>AGGAUAGGGAGAUGAUCGAGGAGCGGCUCAAGACCUACGCCCACCUG<br>UUUGACGACAAAGUGAUGAAGCAACUGAAACGGCGGAGGUAUACCGG<br>CUGGGGUCGGCUGUCCCGCAAGCUGAUCAACGGGAUCAGGGACAAGC<br>AGUCCGGAAAGACCAUCCUCGACUUCCUUAAGUCCGACGGAUUCGCG<br>AACCGCAACUUCAUGCAACUUAUCCACGACGACUCGCUGACAUUCAA<br>GGAAGAUAUCCAGAAGGCCCAGGUGUCCGGACAGGGGGACUCGCUUC<br>AUGAGCACAUCGCUAACCUGGCCGGAUCCCCCGCCAUAAAAAAGGGC<br>AUUCUGCAGACCGUCAAAGUGGUGGAUGAGCUGGUCAAGGUCAUGGG<br>CCGGCAUAAGCCGGAAAACAUCGUCAUCGAGAUGGCCCGCGAGAACC<br>AGACUACGCAGAAGGGCCAGAAGAACUCCCGGGAGCGGAUGAAGCGG<br>AUUGAAGAGGGCAUCAAGGAGCUCGGCAGCCAGAUUCUGAAGGAACA<br>UCCCGUGGAAAACACCCAGCUGCAAAACGAAAAGCUCUAUUUGUACU<br>AUCUGCAAAACGGACGCGAUAUGUACGUGGAUCAGGAGCUGGACAUU<br>AACAGACUGAGCGACUAUGACGUGGAUCACAUUGUGCCUCAAAGCUU<br>CCUCAAGGACGACUCAAUUGACAACAAGGUCCUGACCAGAAGCGACA<br>AGAACAGAGGAAAGUCGGAUAAUGUGCCGUCCGAAGAAGUGGUCAAG<br>AAGAUGAAGAAUUACUGGAGACAGCUCCUGAAUGCGAAGCUCAUUUAC<br>CCAGCGGAAGUUCGAUAACCUGACCAAGGCCGAAAGGGGUGGACUGU<br>CCGAACUCGACAAAGCUGGCUUCAUCAAGCGCCAACUGGUCGAAACC<br>AGGCAGAUCACCAAGCACGUCGCCCAGAUUCUGGACAGCCGCAUGAA<br>CACUAAGUACGACGAGAACGAUAAGCUGAUCCGCGAAGUGAAGGUCA<br>UCACCCUGAAGUCCAAGCUGGUGUCCGACUUUCGGAAGGAUUUCCAG<br>UUUUACAAGGUCCGCGAGAUCAACAACUACCAUCACGCCCACGACGC<br>GUACCUUAACGCAGUCGUGGGAACGGCUCUUAUCAAGAAGUACCCAA<br>AGCUGGAGUCGGAAUUUGUGUACGGAGACUACAAAGUGUACGACGUG<br>CGCAAGAUGAUCGCCAAAUCUGAGCAAGAGAUCGGGAAGGCAACCGC<br>CAAAUACUUCUUCUACUCAAACAUUAUGAAUUUUUUCAAAACUGAGA<br>UUACCCUGGCUAACGGAGAAAUUCGGAAGCGCCCCCUGAUUGAAACC | 4 |

-continued

| Name/Description | Type | Sequence | SEQ ID NO |
|---|---|---|---|
| | | AACGGAGAAACUGGAGAAAUUGUGUGGGACAAGGGACGGGACUUCGC<br>CACCGUCCGCAAGGUCCUCUCAAUGCCCCAAGUCAACAUCGUGAAAA<br>AGACCGAAGUGCAAACCGGCGGCUUCUCAAAGGAGUCCAUCCUGCCU<br>AAGCGCAACAGCGACAAGCUGAUUGCCAGGAAGAAGGACUGGGACCC<br>GAAGAAGUACGGAGGAUUUGAUUCCCCUACCGUGGCCUACUCCGUGC<br>UCGUGGUGGCCAAAGUGGAAAAGGGGAAAUCCAAGAAGCUGAAGUCG<br>GUGAAGGAGCUUUUGGGUAUCACCAUCAUGGAACGCUCCUCGUUCGA<br>AAAGAACCCAAUCGAUUUCCUGGAAGCUAAGGGUUAUAAGGAAGUGA<br>AAAAGGACCUGAUUAUCAAGCUGCCCAAGUACUCACUGUUCGAGCUG<br>GAAAACGGUCGGAAAAGGAUGCUGGCCAGCGCCGGAGAACUCCAGAA<br>GGGAAACGAACUGGCACUGCCGUCCAAAUACGUCAACUUCCUCUACC<br>UUGCAUCCCAUUACGAAAAACUCAAGGGAUCGCCGGAGGACAACGAG<br>CAGAAGCAGCUUUUCGUGGAGCAACACAAGCAUUACUUGGACGAGAU<br>CAUCGAGCAGAUUUCCGAGUUCUCAAAGCGCGUGAUCCUGGCCGACG<br>CAAAUCUGGACAAGGUCCUGUCCGCGUACAAUAAGCAUCGGGACAAG<br>CCUAUCCGCGAACAGGCCGAGAACAUCAUCCAUCUGUUCACUCUGAC<br>AAACCUGGGCGCACCCGCCGCGUUCAAGUACUUUGACACCACCAUCG<br>AUAGGAAGCGAUACACCUCAACUAAGGAAGUGUUGGACGCGACCCUU<br>AUCCAUCAGUCGAUCACCGGGCUGUACGAAACACGGAUCGACCUCAG<br>CCAGUUGGGGAGGCGACAAGCGCCCUGCGGCUACCAAGAAGGCCGGAC<br>AGGCCAAGAAGAAGAAAUGA | |
| RNA-009 coding region Nucleoplasmin NLS underlined SV40 NLS in bold italics SpCas9 polypeptide in italics | amino acid | MAPKKKRKVGIHGVPAADKKYSIGLDIGTNSVGWAVITDEYKVPSKK<br>FKVLGNTDRHSIKKNLIGALLFDSGETAEATRLKRTARRRYTRRKNR<br>ICYLQEIFSNEMAKVDDSFFHRLEESFLVEEDKKHERHPIFGNIVDE<br>VAYHEKYPTIYHLRKKLVDSTDKADLRLIYLALAHMIKFRGHFLIEG<br>DLNPDNSDVDKLFIQLVQTYNGLFEENPINASGVDAKAILSARLSKS<br>RRLENLIAQLPGEKKNGLFGNLIALSLGLTPNFKSNFDLAEDAKLQL<br>SKDTYDDDLDNLLAQIGDQYADLFLAAKNLSDAILLSDILRVNTEIT<br>KAPLSASMTKRYDEHHGDLTLLKALVRGGLPEKYKEIFFDGSKNGYA<br>GYIDGGASQEEFYKFIKPILEKMDGTEELLVKLNREDLLRKGRTFDN<br>GSIPHQIHLGELHAILRRQEDFYPFLKDNREKIEKILTFRIPYYVGP<br>LARGNSRFAWMTRKSEETITPWNFEEVVDKGASAQSFIERMTNFDKN<br>LPNEKVLPKHSLLYEYFTVYNELTKVKYVTEGMRKPAFLSGEQKKAI<br>VDLLFKTNRKVTVKQLKEDYFKKIECFDSVEISGVEDRFNASLGTYH<br>DLLKIIKDKDFLDNEENEDILEDIVLTLTLFEDREMIEERLKTYAHL<br>FDDKVMKGLKRRRYTGWGRLSRKLINGIRDKGSGKTILDFLKSDGFA<br>NRNFMGLIHDDSLTFKEDIQKAQVSGQGDSLHEHIANTAGSPAIKKG<br>ILQTVKVVDELVKVMGRHKPENIVIEMARENGTTGKGQKNSRERMKR<br>IEEGIKELGSGILKEHPVENTQLGNEKLYLYYLGNGRDMYVDGELDI<br>NRLSDYDVDHIVPQSFLKDDSIDNKVLTRSDKNRGKSDNVPSEEVVK<br>KMKNYWRGLLNAKLITGRKFDNLTKAERGGLSELDKAGFIKRGLVET<br>RQITKHVAQILDSRMNTKYDENDKLIREVKVITLKSKLVSDFRKDFQ<br>FYKVREINNYHHAHDAYLNAVVGTALIKKYPKLESEFVYGDYKVYDV<br>RKMIAKSEQEIGKATAKYFFYSNIMNFFKTEITLANGEIRKRPLIET<br>NGETGEIVWDKGRDFATVRKVLSMPGVNIVKKTEVGTGGFSKESILP<br>KRNSDKLIARKKDWDPKKYGGFDSPTVAYSVLVVAKVEKGKSKKLKS<br>VKELLGITIMERSSFEKNPIDFLEAKGYKEVKKDLIIKLPKYSLFEL<br>ENGRKRMLASAGELQKGNELALPSKYVNFLYLASHYEKLKGSPEDNE<br>QKQLFVEQHKHYLDEIIEQISEFSKRVILADANLDKVLSAYNKHRDK<br>PIREQAENIIHLFTLTNLGAPAAFKYFDTTIDRKRYTSTKEVLDATL<br>IHGSITGLYETRIDLSGLGGDKRPAATKKAGQAKKKK | 5 |
| SpCas9 polypeptide | Amino acid | DKKYSIGLDIGTNSVGWAVITDEYKVPSKKFKVLGNTDRHSIKKNLI<br>GALLFDSGETAEATRLKRTARRRYTRRKNRICYLQEIFSNEMAKVDD<br>SFFHRLEESFLVEEDKKHERHPIFGNIVDEVAYHEKYPTIYHLRKKL<br>VDSTDKADLRLIYLALAHMIKFRGHFLIEGDLNPDNSDVDKLFIQLV<br>QTYNQLFEENPINASGVDAKAILSARLSKSRRLENLIAQLPGEKKNG<br>LFGNLIALSLGLTPNFKSNFDLAEDAKLQLSKDTYDDDLDNLLAQIG<br>DQYADLFLAAKNLSDAILLSDILRVNTEITKAPLSASMIKRYDEHHQ<br>DLTLLKALVRQQLPEKYKEIFFDQSKNGYAGYIDGGASQEEFYKFIK<br>PILEKMDGTEELLVKLNREDLLRKQRTFDNGSIPHQIHLGELHAILR<br>RQEDFYPFLKDNREKIEKILTFRIPYYVGPLARGNSRFAWMTRKSEE<br>TITPWNFEEVVDKGASAQSFIERMTNFDKNLPNEKVLPKHSLLYEYF<br>TVYNELTKVKYVTEGMRKPAFLSGEQKKAIVDLLFKTNRKVTVKQLK<br>EDYFKKIECFDSVEISGVEDRFNASLGTYHDLLKIIKDKDFLDNEEN<br>EDILEDIVLTLTLFEDREMIEERLKTYAHLFDDKVMKQLKRRRYTGW<br>GRLSRKLINGIRDKQSGKTILDFLKSDGFANRNFMQLIHDDSLTFKE<br>DIQKAQVSGQGDSLHEHIANLAGSPAIKKGILQTVKVVDELVKVMGR<br>HKPENIVIEMARENQTTQKGQKNSRERMKRIEEGIKELGSQILKEHP<br>VENTQLQNEKLYLYYLQNGRDMYVDQELDINRLSDYDVDHIVPQSFL<br>KDDSIDNKVLTRSDKNRGKSDNVPSEEVVKKMKNYWRQLLNAKLITQ<br>RKFDNLTKAERGGLSELDKAGFIKRQLVETRQITKHVAQILDSRMNT<br>KYDENDKLTREVKVITLKSKLVSDFRKDFQFYKVREINNYHHAHDAY<br>LNAVVGTALIKKYPKLESEFVYGDYKVYDVRKMIAKSEQEIGKATAK<br>YFFYSNIMNFEKTEITLANGEIRKRPLIETNGETGEIVWDKGRDFAT | 6 |

| Name/Description | Type | Sequence | SEQ ID NO |
|---|---|---|---|
| | | VRKVLSMPQVNIVKKTEVQTGGFSKESILPKRNSDKLIARKKDWDPK<br>KYGGFDSPTVAYSVLVVAKVEKGKSKKLKSVKELLGITIMERSSFEK<br>NPIDFLEAKGYKEVKKDLIIKLPKYSLFELENGRKRMLASAGELQKG<br>NELALPSKYVNFLYLASHYEKLKGSPEDNEQKQLFVEQHKHYLDEII<br>EQISEFSKRVILADANLDKVLSAYNKHRDKPIREQAENIIHLFTLTN<br>LGAPAAFKYFDTTIDRKRYTSTKEVLDATLIHQSITGLYETRIDLSQ<br>LGGD | |
| nucleoplasmin NLS | Amino acid | KRPAATKKAGQAKKKK | 7 |
| SV40 NLS | Amino acid | PKKKRKV | 8 |
| RNA-009 5' UTR | DNA | AGAGGAAATAAGAGAGAAAAGAAGAGTAAGAAGAAATATAAGAGCCA<br>CC | 9 |
| RNA-009 5' UTR | RNA | AGAGGAAAUAAGAGAGAAAAGAAGAGUAAGAAGAAAUAUAAGAGCCA<br>CC | 10 |
| RNA-009 3' UTR | DNA | GCGGCCGCTTAATTAAGCTGCCTTCTGCGGGGCTTGCCTTCTGGCCA<br>TGCCCTTCTTCTCTCCCTTGCACCTGTACCTCTTGGTCTTTGAATAA<br>AGCCTGAGTAGGAAGTCTAG | 11 |
| RNA-009 3' UTR | RNA | GCGGCCGCUUAAUUAAGCUGCCUUCUGCGGGGCUUGCCUUCUGGCCA<br>UGCCCUUCUUCUCUCCCUUGCACCUGUACCUCUUGGUCUUUGAAUAA<br>AGCCUGAGUAGGAAGUCUAG | 12 |
| Poly-A tail | RNA | AAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAA | 13 |
| RNA-009.2 Full-length mRNA 5' UTR IN BOLD 3' UTR IN BOLD ITALICS POLY-A TAIL IN UNDERLINE | RNA | AGGAAAUAAGAGAGAAAAGAAGAGUAAGAAGAAAUAUAAGAGCCACC<br>AUGGCCCCUAAGAAGAAGAGAAAAGUCGGAAUUCACGGAGUCCCCGC<br>CGCCGACAAAAAGUACUCCAUUGGCCUUGAUAUUGGAACCAACUCCG<br>UGGGUUGGGCCGUGAUCACUGACGAGUACAAGGUGCCGUCCAAGAAG<br>UUCAAGGUGCUGGGGAACACUGACCGGCACUCAAUUAAGAAGAACCU<br>GAUUGGGGCGCUGCUGUUCGACUCCGGAGAAACCGCGGAGGCUACCC<br>GCCUGAAGCGGACUGCCCGGCGGGAGAUACACGCGCAGGAAGAACCG<br>GAUUUGCUACCUCCAAGAAAUCUUCAGCAACGAAAUGGCAAAGGUGGA<br>CGAUUCCUUCUUCCAUCGCCUGGAAGAGAGCUUCCUGGUGGAAGAGG<br>ACAAGAAGCACGAAAGACACCCGAUUUUCGGCAACAUCGUGGAUGAG<br>GUCGCAUACCACGAAAAGUACCCCACCAUCUAUCAUCUUCGGAAGAA<br>GCUGGUCGACUCCACCGAUAAGGCCGAUCUGCGCCUGAUCUACUUGG<br>CGCUGGCUCACAUGAUUAAGUUCAGAGGACACUUUCUGAUAGAGGGC<br>GACCUCAAUCCCGAUAACUCCGACGUGGAUAAGCUGUUCAUCCAACU<br>GGUGCAGACGUACAACCAACUGUUUGAAGAGAAUCCAAUCAACGCCA<br>GCGGGGUGGACGCCAAGGCCAUCCUGUCCGCCCGGCUGUCAAAGUCC<br>AGACGCCUGGAGAAUCUCAUCGCGCAACUCCCUGGCGAAAAAAAGAA<br>CGGACUCUUCGGGAAUCUGAUUGCUCUGUCCCUGGGGCUCACUCCGA<br>ACUUCAAGUCGAACUUCGACCUGGCGGAGGACGCUAAGCUGCAGCUG<br>UCCAAGGACACCUACGAUGACGAUCUGGAUAACCUUCUGGCCCAGAU<br>CGGGGAUCAAUACGCCGAUCUCUUCCUGGCCGCAAAGAACUUGUCGG<br>AUGCUAUUCUGCUGAGCGACAUUCUGCGGGUCAAUACUGAAAUCACC<br>AAGGCGCCCCUGUCGGCCAGCAUGAUCAAGCGCUACGACGAACACCA<br>CCAAGACCUGACUCUGCUGAAGGCCCUCGUGCGCCAGCAGCUGCCUG<br>AAAAGUACAAGGAGAUUUUCUUCGACCAGUCCAAGAACGGAUACGCC<br>GGAUACAUUGACGGAGGGGCCAGCCAGGAGGAAUUUUACAAAUUCAU<br>CAAGCCCAUUCUCGAGAAAAUGGACGGAACCGAAGAGUUGCUCGUGA<br>AGCUGAACAGAGAGGAUCUCCUCCGGAAGCAGCGGACCUUCGACAAC<br>GGUUCCAUCCCGCACCAAAUCCACCUGGGCGAAUUGCACGCCAUCCU<br>CCGGCGGCAGGAAGAUUUCUACCCAUUCUUGAAGGACAAUCGCGAAA<br>AGAUCGAAAAGAUCUUGACUUUCCGCAUCCCGUACUACGUGGGCCCU<br>CUGGCCCGCGGCAACUCCCGCUUCGCUUGGAUGACACGGAAGUCCGA<br>GGAAACCAUUACGCCCUGGAACUUCGAGGAAGUGGUGGACAAGGGGG<br>CGUCCGCCCAGAGCUUCAUCGAACGCAUGACCAAUUUCGACAAGAAC<br>CUCCCGAACGAAAAAGUGCUGCCAAAGCACUCGCUCCUCUACGAAUA<br>CUUCACCGUGUACAACGAGCUGACUAAGGUCAAAUACGUGACUGAGG<br>GAAUGCGGAAGCCGGCCUUCCUGUCGGGAGAGCAGAAGAAGGCCAUA<br>GUGGACUUGCUUUUCAAGACUAACCGGAAGGUCACUGUGAAGCAACU<br>CAAGGAGGACUACUUCAAGAAGAUCGAGUGUUUCGACUCGGUGGAGA<br>UCUCGGGUGUCGAGGACCGCUUCAACGCCUCCCUGGGAACUUACCAC<br>GAUCUGCUGAAGAUCAUCAAGGACAAGGACUUCCUCGAUAACGAAGA<br>AAAUGAGGACAUCCUCGAGGAUAUCGUGCUGACCCUGACCUUGUUCG<br>AGGAUAGGGAGAUGAUCGAGGAGCGGCUCAAGACCUACGCCCACCUG<br>UUUGACGACAAAGUGAUGAAGCAACUGAAACGGCGGAGGUAUACCGG | 14 |

| Name/ Description | Type | Sequence | SEQ ID NO |
|---|---|---|---|
| | | CUGGGGUCGGCUGUCCCGCAAGCUGAUCAACGGGAUCAGGGACAAGC<br>AGUCCGGAAAGACCAUCCUCGACUUCCUUAAGUCCGACGGAUUCGCG<br>AACCGCAACUUCAUGCAACUUAUCCACGACGACUCGCUGACAUUCAA<br>GGAAGAUAUCCAGAAGGCCCAGGUGUCCGGACAGGGGGACUCGCUUC<br>AUGAGCACAUCGCUAACCUGGCCGGAUCCCCCGCCAUAAAAAGGGC<br>AUUCUGCAGACCGUCAAAGUGGUGGAUGAGCUGGUCAAGGUCAUGGG<br>CCGGCAUAAGCCGGAAAACAUCGUCAUCGAGAUGGCCCGCGAGAACC<br>AGACUACGCAGAAGGGCCAGAAGAACUCCCGGGAGCGGAUGAAGCGG<br>AUUGAAGAGGGCAUCAAGGAGCUCGGCAGCCAGAUUCUGAAGGAACA<br>UCCCGUGGAAAACACCCAGCUGCAAAACGAAAAGCUCUAUUUGUACU<br>AUCUGCAAAACGGACGCGAUAUGUACGUGGAUCAGGAGCUGGACAUU<br>AACAGACUGAGCGACUAUGACGUGGAUCACAUUGUGCCUCAAAGCUU<br>CCUCAAGGACGACUCAAUUGACAACAAGGUCCUGACCAGAAGCGACA<br>AGAACAGAGGAAAGUCGGAUAAUGUGCCGUCCGAAGAAGUGGUCAAG<br>AAGAUGAAGAAUUACUGGAGACAGCUCCUGAAUGCGAAGCUCAUUAC<br>CCAGCGGAAGUUCGAUAACCUGACCAAGGCCGAAAGGGGUGGACUGU<br>CCGAACUCGACAAAGCUGGCUUCAUCAAGCGCCAACUGGUCGAAACC<br>AGGCAGAUCACCAAGCACGUCGCCCAGAUUCUGGACAGCCGCAUGAA<br>CACUAAGUACGACGAGAACGAUAAGCUGAUCCGCGAAGUGAAGGUCA<br>UCACCCUGAAGUCCAAGCUCGUGUCCGACUUUCGGAAGGAUUUCCAG<br>UUUUACAAGGUCCGCGAGAUCAACAACUACCAUCACGCCCACGACGC<br>GUACCUUAACGCAGUCGUGGGAACGGCUCUUAUCAAGAAGUACCCAA<br>AGCUGGAGUCGGAAUUUGUGUACGGAGACUACAAAGUGUACGACGUG<br>CGCAAGAUGAUCGCCAAAUCUGAGCAAGAGAUCGGGAAGGCAACCGC<br>CAAAUACUUCUUCUACUCAAACAUUAUGAAUUUUUUCAAAACUGAGA<br>UUACCCUGGCUAACGGAGAAAUUCGGAAGCGCCCCCUGAUUGAAACC<br>AACGGAGAAACUGGAGAAAUUGUGUGGGACAAGGGACGGGACUUCGC<br>CACCGUCCGCAAGGUCCUCUCAAUGCCCCAAGUCAACAUCGUGAAAA<br>AGACCGAAGUGCAAACCGGCGGCUUUCUCAAAGGAGUCCAUCCUGCCU<br>AAGCGCAACAGCGACAAGCUGAUUGCCAGGAAGAAGGACUGGGACCC<br>GAAGAAGUACGGAGGAUUUGAUUCCCCUACCGUGGCCUACUCCGUGC<br>UCGUGGUGGCCAAAGUGGAAAAGGGGAAAUCCAAGAAGCUGAAGUCG<br>GUGAAGGAGCUUUUGGGUAUCACCAUCAUGGAACGCUCCUCGUUCGA<br>AAAGAACCCAAUCGAUUUCCUGGAAGCUAAGGGUUAUAAGGAAGUGA<br>AAAAGGACCUGAUUAUCAAGCUGCCCAAGUACUCACUGUUCGAGCUG<br>GAAAACGGUCGAAAAGGAUGCUGGCCAGCGCCGGAGAACUCCAGAA<br>GGGAAACGAACUGGCACUGCCGUCCAAAUACGUCAACUUCCUCUACC<br>UUGCAUCCCAUUACGAAAAACUCAAGGGAUCGCCGGAGGACAACGAG<br>CAGAAGCAGCUUUUCGUGGAGCAACAAGCAUUACUUGGACGAGAU<br>CAUCGAGCAGAUUUCCGAGUUCUCAAAGCGCGUGAUCCUGGCCGACG<br>CAAAUCUGGACAAGGUCCUGUCCGCGUACAAUAAGCAUCGGGACAAG<br>CCUAUCCGCGAACAGGCCGAGAACAUCAUCCAUCUGUUCACUCUGAC<br>AAACCUGGGCGCACCCGCCGCGUUCAAGUACUUUGACACCACCAUCG<br>AUAGGAAGCGAUACACCUCAACUAAGGAAGUGUUGGACGCGACCCUU<br>AUCCAUCAGUCGAUCACCGGGCUGUACGAAACACGGAUCGACCUCAG<br>CCAGUUGGGAGGCGACAAGCGCCCUGCGGCUACCAAGAAGGCCGGAC<br>AGGCCAAGAAGAAGAAAUGA*GCGGCCGCUUAAUUAAGCUGCCUUCUG*<br>*CGGGGCUUGCCUUCUGGCCAUGCCCUUCUUCUCUCCCUUGCACCUGU*<br>*ACCUCUUGGUCUUUGAAUAAAGCCUGAGUAGGAAGUCUAG*<u>AAAAAA</u><br><u>AAAAAAAAAAAAAAAAAAAAAAAAAAAAAAAAAAAAAAAAAAAAAAA</u><br><u>AAAAAAAAAAAAAAAAAAAAAAAAAAAAAAAAAAAAAAAAAAAAAAA</u><br><u>AAAAAAAAAAAAAAAAAAAAAAAAAAAAAAAAAAA</u> | |
| RNA-009.2<br>5' UTR | RNA | AGGAAAUAAGAGAGAAAAGAAGAGUAAGAAGAAAUAUAAGAGCCACC | 15 |
| Parent mRNA | DNA | AGGAAATAAGAGAGAAAAGAAGAGTAAGAAGAAATATAAGAGCCACC<br>ATGGCCCCAAAGAAGAAGCGGAAGGTCGGTATCCACGGAGTCCCAGC<br>AGCCGACAAGAAGTACAGCATCGGCCTGGACATCGGCACCAACTCTG<br>TGGGCTGGGCCGTGATCACCGACGAGTACAAGGTGCCCAGCAAGAAA<br>TTCAAGGTGCTGGGCAACACCGACCGGCACAGCATCAAGAAGAACCT<br>GATCGGAGCCCTGCTGTTCGACAGCGGCGAAACAGCCGAGGCCACCC<br>GGCTGAAGAGAACCGCCAGAAGAAGATACACCAGACGGAAGAACCGG<br>ATCTGCTATCTGCAAGAGATCTTCAGCAACGAGATGGCCAAGGTGGA<br>CGACAGCTTCTTCCACAGACTGGAAGAGTCCTTCCTGGTGGAAGAGG<br>ACAAGAAGCACGAGAGACACCCCATCTTCGGCAACATCGTGGACGAG<br>GTGGCCTACCACGAGAAGTACCCCACCATCTACCACCTGAGAAAGAA<br>ACTGGTGGACAGCACCGACAAGGCCGACCTGAGACTGATCTACCTGG<br>CCCTGGCCCACATGATCAAGTTCAGAGGCCACTTCCTGATCGAGGGC<br>GACCTGAACCCCGACAACAGCGACGTGGACAAGCTGTTCATCCAGCT<br>GGTGCAGACCTACAACCAGCTGTTCGAGGAAAACCCCATCAACGCCA<br>GCGGCGTGGACGCCAAGGCTATCCTGTCTGCCAGACTGAGCAAGAGC<br>AGAAGGCTGGAAAATCTGATCGCCCAGCTGCCCGGCGAGAAGAAGAA<br>CGGCCTGTTCGGCAACCTGATTGCCCTGAGCCTGGGCCTGACCCCCA<br>ACTTCAAGAGCAACTTCGACCTGGCCGAGGATGCCAAACTGCAGCTG<br>AGCAAGGACACCTACGACGACGACCTGGACAACCTGCTGGCCCAGAT | 16 |

| Name/Description | Type | Sequence | SEQ ID NO |
|---|---|---|---|
| | | CGGCGACCAGTACGCCGACCTGTTCCTGGCCGCCAAGAACCTGTCTG | |
| | | ACGCCATCCTGCTGAGCGACATCCTGAGAGTGAACACCGAGATCACC | |
| | | AAGGCCCCCCTGAGCGCCTCTATGATCAAGAGATACGACGAGCACCA | |
| | | CCAGGACCTGACCCTGCTGAAAGCTCTCGTGCGGCAGCAGCTGCCTG | |
| | | AGAAGTACAAAGAAATCTTCTTCGACCAGAGCAAGAACGGCTACGCC | |
| | | GGCTACATCGATGGCGGCGCTAGCCAGGAAGAGTTCTACAAGTTCAT | |
| | | CAAGCCCATCCTGGAAAAGATGGACGGCACCGAGGAACTGCTCGTGA | |
| | | AGCTGAACAGAGAGGACCTGCTGAGAAAGCAGAGAACCTTCGACAAC | |
| | | GGCAGCATCCCCCACCAGATCCACCTGGGAGAGCTGCACGCTATCCT | |
| | | GAGAAGGCAGGAAGATTTTTACCCATTCCTGAAGGACAACCGGGAAA | |
| | | AGATCGAGAAGATCCTGACCTTCAGGATCCCCTACTACGTGGGCCCC | |
| | | CTGGCCAGAGGCAACAGCAGATTCGCCTGGATGACCAGAAAGAGCGA | |
| | | GGAAACCATCACCCCCTGGAACTTCGAGGAAGTGGTGGACAAGGGCG | |
| | | CCAGCGCCCAGAGCTTCATCGAGAGAATGACAAACTTCGATAAGAAC | |
| | | CTGCCCAACGAGAAGGTGCTGCCCAAGCACAGCCTGCTGTACGAGTA | |
| | | CTTCACCGTGTACAACGAGCTGACCAAAGTGAAATACGTGACCGAGG | |
| | | GAATGAGAAAGCCCGCCTTCCTGAGCGGCGAGCAGAAAAAGGCCATC | |
| | | GTGGACCTGCTGTTCAAGACCAACAGAAAAGTGACCGTGAAGCAGCT | |
| | | GAAAGAGGACTACTTCAAGAAAATCGAGTGCTTCGACTCCGTGGAAA | |
| | | TCTCCGGCGTGGAAGATAGATTCAACGCCTCCCTGGGCACATACCAC | |
| | | GATCTGCTGAAAATTATCAAGGACAAGGACTTCCTGGATAACGAAGA | |
| | | GAACGAGGACATTCTGGAAGATATCGTGCTGACCCTGACACTGTTTG | |
| | | AGGACCGCGAGATGATCGAGGAAAGGCTGAAAACCTACGCTCACCTG | |
| | | TTCGACGACAAAGTGATGAAGCAGCTGAAGAGAAGGCGGTACACCGG | |
| | | CTGGGGCAGGCTGAGCAGAAAGCTGATCAACGGCATCAGAGACAAGC | |
| | | AGAGCGGCAAGACAATCCTGGATTTCCTGAAGTCCGACGGCTTCGCC | |
| | | AACCGGAACTTCATGCAGCTGATCCACGACGACAGCCTGACATTCAA | |
| | | AGAGGACATCCAGAAAGCCCAGGTGTCCGGCCAGGGCGACTCTCTGC | |
| | | ACGAGCATATCGCTAACCTGGCCGGCAGCCCCGCTATCAAGAAGGGC | |
| | | ATCCTGCAGACAGTGAAGGTGGTGGACGAGCTCGTGAAAGTGATGGG | |
| | | CAGACACAAGCCCGAGAACATCGTGATCGAGATGGCTAGAGAGAACC | |
| | | AGACCACCCAGAAGGGACAGAAGAACTCCCGCGAGAGGATGAAGAGA | |
| | | ATCGAAGAGGGCATCAAAGAGCTGGCAGCCAGATCCTGAAAGAACA | |
| | | CCCCGTGGAAAACACCCAGCTGCAGAACGAGAAGCTGTACCTGTACT | |
| | | ACCTGCAGAATGGCCGGGATATGTACGTGGACCAGGAACTGGACATC | |
| | | AACAGACTGTCCGACTACGATGTGGACCATATCGTGCCTCAGAGCTT | |
| | | TCTGAAGGACGACTCCATCGATAACAAAGTGCTGACTCGGAGCGACA | |
| | | AGAACAGAGGCAAGAGCGACAACGTGCCCTCCGAAGAGGTCGTGAAG | |
| | | AAGATGAAGAACTACTGGCGACAGCTGCTGAACGCCAAGCTGATTAC | |
| | | CCAGAGGAAGTTCGATAACCTGACCAAGGCCGAGAGAGGCGGCCTGA | |
| | | GCGAGCTGGATAAGGCCGGCTTCATCAAGAGGCAGCTGGTGGAAACC | |
| | | AGACAGATCACAAAGCACGTGGCACAGATCCTGGACTCCCGGATGAA | |
| | | CACTAAGTACGACGAAAACGATAAGCTGATCCGGGAAGTGAAAGTGA | |
| | | TCACCCTGAAGTCCAAGCTGGTGTCCGATTTCCGGAAGGATTTCCAG | |
| | | TTTTACAAAGTGCGCGAGATCAACAACTACCACCACGCCCACGACGC | |
| | | CTACCTGAACGCCGTCGTGGGAACCGCCCTGATCAAAAAGTACCCTA | |
| | | AGCTGGAAAGCGAGTTCGTGTACGGCGACTACAAGGTGTACGACGTG | |
| | | CGGAAGATGATCGCCAAGAGCGAGCAGGAAATCGGCAAGGCTACCGC | |
| | | CAAGTACTTCTTCTACAGCAACATCATGAACTTTTTCAAGACCGAAA | |
| | | TCACCCTGGCCAACGGCGAGATCAGAAAGCGCCCTCTGATCGAGACA | |
| | | AACGGCGAAACCGGGGAGATCGTGTGGGATAAGGGCAGAGACTTCGC | |
| | | CACAGTGCGAAAGGTGCTGAGCATGCCCCAAGTGAATATCGTGAAAA | |
| | | AGACCGAGGTGCAGACAGGCGGCTTCAGCAAAGAGTCTATCCTGCCC | |
| | | AAGAGGAACAGCGACAAGCTGATCGCCAGAAAGAAGGACTGGGACCC | |
| | | CAAGAAGTACGGCGGCTTCGACAGCCCTACCGTGGCCTACTCTGTGC | |
| | | TGGTGGTGGCTAAGGTGGAAAAGGGCAAGTCCAAGAAACTGAAGAGT | |
| | | GTGAAAGAGCTGCTGGGGATCACCATCATGGAAAGAAGCAGCTTTGA | |
| | | GAAGAACCCTATCGACTTTCTGGAAGCCAAGGGCTACAAAGAAGTGA | |
| | | AAAAGGACCTGATCATCAAGCTGCCTAAGTACTCCCTGTTCGAGCTG | |
| | | GAAAACGGCAGAAAGAGAATGCTGGCCTCTGCCGGCGAACTGCAGAA | |
| | | GGGAAACGAGCTGGCCCTGCCTAGCAAATATGTGAACTTCCTGTACC | |
| | | TGGCCTCCCACTATGAGAAGCTGAAGGGCAGCCCTGAGGACAACGAA | |
| | | CAGAAACAGCTGTTTGTGGAACAGCATAAGCACTACCTGGACGAGAT | |
| | | CATCGAGCAGATCAGCGAGTTCTCCAAGAGAGTGATCCTGGCCGACG | |
| | | CCAATCTGGACAAGGTGCTGTCTGCCTACAACAAGCACAGGGACAAG | |
| | | CCTATCAGAGAGCAGGCCGAGAATATCATCCACCTGTTCACCCTGAC | |
| | | AAACCTGGGCGCTCCTGCCGCCTTCAAGTACTTTGACACCACCATCG | |
| | | ACCGGAAGAGGTACACCAGCACCAAAGAGGTGCTGGACGCCACCCTG | |
| | | ATCCACCAGAGCATCACCGGCCTGTACGAGACAAGAATCGACCTGTC | |
| | | TCAGCTGGGAGGCGACAAGAGACCTGCCGCCACTAAGAAGGCCGGAC | |
| | | AGGCCAAAAAGAAGAAGTGAGCGGCCGCTTAATTAAGCTGCCTTCTG | |
| | | CGGGGCTTGCCTTCTGGCCATGCCCTTCTTCTCTCCCTTGCACCTGT | |
| | | ACCTCTTGGTCTTTGAATAAAGCCTGAGTAGGAAGTCTAGAAAAAAA | |
| | | AAAAAAAAAAAAAAAAAAAAAAAAAAAAAAAAAAAAAAAAAAAAAAA | |
| | | AAAAAAAAAAAAAAAAAAAAAA | |

| Name/Description | Type | Sequence | SEQ ID NO |
|---|---|---|---|
| Parent mRNA Full-length mRNA 5' UTR IN BOLD 3' UTR IN BOLD ITALICS POLY-A TAIL IN UNDERLINE | RNA | AGGAAAUAAGAGAGAAAAGAAGAGUAAGAAGAAAUAUAAGAGCCACCAUGGGCCCAAAGAAGAAGCGGAAGGUCGGUAUCCACGGAGUCCCAGCAGCCGACAAGAAGUACAGCAUCGGCCUGGACAUCGGCACCAACUCUGUGGGCUGGGCCGUGAUCACCGACGAGUACAAGGUGCCCAGCAAGAAAUUCAAGGUGCUGGGCAACACCGACCGGCACAGCAUCAAGAAGAACCUGAUCGGAGCCCUGCUGUUCGACAGCGGCGAAACAGCCGAGGCCACCCGGCUGAAGAGAACCGCCAGAAGAAGAUACACCAGACGGAAGAACCGGAUCUGCUAUCUGCAAGAGAUCUUCAGCAACGAGAUGGCCAAGGUGGACGACAGCUUCUUCCACAGACUGGAAGAGUCCUUCCUGGUGGAAGAGGACAAGAAGCACGAGAGACACCCCAUCUUCGGCAACAUCGUGGACGAGGUGGCCUACCACGAGAAGUACCCCACCAUCUACCACCUGAGAAAGAAACUGGUGGACAGCACCGACAAGGCCGACCUGAGACUGAUCUACCUGGCCCUGGCCCACAUGAUCAAGUUCAGAGGCCACUUCCUGAUCGAGGGCGACCUGAACCCCGACAACAGCGACGUGGACAAGCUGUUCAUCCAGCUGGUGCAGACCUACAACCAGCUGUUCGAGGAAAACCCCAUCAACGCCAGCGGCGUGGACGCCAAGGCUAUCCUGUCUGCCAGACUGAGCAAGAGCAGAAGGCUGGAAAAUCUGAUCGCCCAGCUGCCCGGCGAGAAGAAGAACGGCCUGUUCGGCAACCUGAUUGCCCUGAGCCUGGGCCUGACCCCAACUUCAAGAGCAACUUCGACCUGGCCGAGGAUGCCAAACUGCAGCUGAGCAAGGACACCUACGACGACGACCUGGACAACCUGCUGGCCCAGAUCGGCGACCAGUACGCCGACCUGUUCCUGGCCGCCAAGAACCUGUCUGACGCCAUCCUGCUGAGCGACAUCCUGAGAGUGAACACCGAGAUCACCAAGGCCCCCCUGAGCGCCUCUAUGAUCAAGAGAUACGACGAGCACCACCAGGACCUGACCCUGCUGAAAGCUCUCGUGCGGCAGCAGCUGCCUGAGAAGUACAAAGAAAUCUUCUUCGACCAGAGCAAGAACGGCUACGCCGGCUACAUCGAUGGCGGCGCUAGCCAGGAAGAGUUCUACAAGUUCAUCAAGCCCAUCCUGGAAAAGAUGGACGGCACCGAGGAACUGCUCGUGAGCUGAACAGAGAGGACCUGCUGAGAAAGCAGAGAACCUUCGACAACGGCAGCAUCCCCCACCAGAUCCACCUGGGAGAGCUGCACGCUAUCCUGAGAAGGCAGGAAGAUUUUUACCCAUUCCUGAAGGACAACCGGGAAAAGAUCGAGAAGAUCCUGACCUUCAGGAUCCCCUACUACGUGGGCCCCCUGGCCAGAGGCAACAGCAGAUUCGCCUGGAUGACCAGAAAGAGCGAGGAAACCAUCACCCCCUGGAACUUCGAGGAAGUGGUGGACAAGGGCGCCAGCGCCCAGAGCUUCAUCGAGAGAAUGACAAACUUCGAUAAGAACCUGCCCAACGAGAAGGUGCUGCCCAAGCACAGCCUGCUGUACGAGUACUUCACCGUGUACAACGAGCUGACCAAAGUGAAAUACGUGACCGAGGGAAUGAGAAAGCCCGCCUUCCUGAGCGGCGAGCAGAAAAAGGCCAUCGUGGACCUGCUGUUCAAGACCAACAGAAAAGUGACCGUGAAGCAGCUGAAAGAGGACUACUUCAAGAAAAUCGAGUGCUUCGACUCCGUGGAAAUCUCCGGCGUGGAAGAUAGAUUCAACGCCUCCCUGGGCACAUACCACGAUCUGCUGAAAAUUAUCAAGGACAAGGACUUCCUGGAUAACGAAGAAACGAGGACAUUCUGGAAGAUAUCGUGCUGACCCUGACACUGUUUGAGGACCGCGAGAUGAUCGAGGAAAGGCUGAAAACCUACGCUCACCUGUUCGACGACAAAGUGAUGAAGCAGCUGAAGAGAAGGCGGUACACCGGCUGGGGCAGGCUGAGCAGAAAGCUGAUCAACGGCAUCAGAGACAAGCAGAGCGGCAAGACAAUCCUGGAUUUCCUGAAGUCCGACGGCUUCGCCAACCGGAACUUCAUGCAGCUGAUCCACGACGACAGCCUGACAUUCAAAGAGGACAUCCAGAAAGCCCAGGUGUCCGGCCAGGGCGACUCUCUGCACGAGCAUAUCGCUAACCUGGCCGGCAGCCCCGCUAUCAAGAAGGGCAUCCUGCAGACAGUGAAGGUGGUGGACGAGCUCGUGAAAGUGAUGGGCAGACACAAGCCCGAGAACAUCGUGAUCGAGAUGGCUAGAGAGAACCAGACCACCCAGAAGGGACAGAAGAACUCCCGCGAGAGGAUGAAGAGAAUCGAAGAGGGCAUCAAAGAGCUGGGCAGCCAGAUCCUGAAAGAACACCCCGUGGAAAACACCCAGCUGCAGAACGAGAAGCUGUACCUGUACUACCUGCAGAAUGGCCGGGAUAUGUACGUGGACCAGGAACUGGACAUCAACAGACUGUCCGACUACGAUGUGGACCAUAUCGUGCCUCAGAGCUUUCUGAAGGACGACUCCAUCGAUAACAAAGUGCUGACUCGGAGCGACAAGAACAGAGGCAAGAGCGACAACGUGCCCUCCGAAGAGGUCGUGAAGAAGAUGAAGAACUACUGGCGACAGCUGCUGAACGCCAAGCUGAUUACCCAGAGGAAGUUCGAUAACCUGACCAAGGCCGAGAGAGGCGGCCUGAGCGAGCUGGAUAAGGCCGGCUUCAUCAAGAGGCAGCUGGUGGAAACCAGACAGAUCACAAAGCACGUGGCACAGAUCCUGGACUCCCGGAUGAACACUAAGUACGACGAAAACGAUAAGCUGAUCCGGGAAGUGAAAGUGAUCACCCUGAAGUCCAAGCUGGUGUCCGAUUUCCGGAAGGAUUUCCAGUUUUACAAAGUGCGCGAGAUCAACAACUACCACCACGCCCACGACGCCUACCUGAACGCCGUCGUGGGAACCGCCCUGAUCAAAAAGUACCCCAAGCUGGAAAGCGAGUUCGUGUACGGCGACUACAAGGUGUACGACGUGCGGAAGAUGAUCGCCAAGAGCGAGCAGGAAAUCGGCAAGGCUACCGCCAAGUACUUCUUCUACAGCAACAUCAUGAACUUUUUCAAGACCGAAAUCACCCUGGCCAACGGCGAGAUCAGAAAGCGCCCUCUGAUCGAGACAAACGGCGAAACCGGGGAGAUCGUGUGGGAUAAGGGCAGAGACUUCGCCACAGUGCGAAAGGUGCUGAGCAUGCCCCAAGUGAAUAUCGUGAAAAAGACCGAGGUGCAGACAGGCGGCUUCAGCAAAGAGUCUAUCCUGCCCAAGAGGAACAGCGACAAGCUGAUCGCCAGAAAGAAGGACUGGGACCCCAAGAAGUACGGCGGCUUCGACAGCCCCUACCGUGGCCUACUCUGUGCUGGUGGUGGCUAAGGUGGAAAAGGGCAAGUCCAAGAAACUGAAGAGU | 17 |

| Name/Description | Type | Sequence | SEQ ID NO |
|---|---|---|---|
| | | GUGAAAGAGCUGCUGGGGAUCACCAUCAUGGAAAGAAGCAGCUUUGA | |
| | | GAAGAACCCUAUCGACUUUCUGGAAGCCAAGGGCUACAAAGAAGUGA | |
| | | AAAAGGACCUGAUCAUCAAGCUGCCUAAGUACUCCCUGUUCGAGCUG | |
| | | GAAAACGGCAGAAAGAGAAUGCUGGCCUCUGCCGGCGAACUGCAGAA | |
| | | GGGAAACGAGCUGGCCCUGCCUAGCAAAUAUGUGAACUUCCUGUACC | |
| | | UGGCCUCCCACUAUGAGAAGCUGAAGGGCAGCCCUGAGGACAACGAA | |
| | | CAGAAACAGCUGUUUGUGGAACAGCAUAAGCACUACCUGGACGAGAU | |
| | | CAUCGAGCAGAUCAGCGAGUUCUCCAAGAGAGUGAUCCUGGCCGACG | |
| | | CCAAUCUGGACAAGGUGCUGUCUGCCUACAACAAGCACAGGGACAAG | |
| | | CCUAUCAGAGAGCAGGCCGAGAAUAUCAUCCACCUGUUCACCCUGAC | |
| | | AAACCUGGGCGCUCCUGCCGCCUUCAAGUACUUUGACACCACCAUCG | |
| | | ACCGGAAGAGGUACACCAGCACCAAAGAGGUGCUGGACGCCACCCUG | |
| | | AUCCACCAGAGCAUCACCGGCCUGUACGAGACAAGAAUCGACCUGUC | |
| | | UCAGCUGGGAGGCGACAAGAGACCUGCCGCCACUAAGAAGGCCGGAC | |
| | | AGGCCAAAAAGAAGAAGUGA*GCGGCCGCUUAAUUAAGCUGCCUUCUG* | |
| | | *CGGGGCUUGCCUUCUGGCCAUGCCCUUCUUCUCUCCCUUGCACCUGU* | |
| | | *ACCUCUUGGUCUUUGAAUAAAGCCUGAGUAGGAAGUCUAG*AAAAAAA | |
| | | AAAAAAAAAAAAAAAAAAAAAAAAAAAAAAAAAAAAAAAAAAAAAAA | |
| | | AAAAAAAAAAAAAAAAAAAAAAAAAA | |

What is claimed:

1. An mRNA comprising:
   a 5' untranslated region (UTR);
   an open reading frame (ORF) comprising a nucleotide sequence that encodes a site-directed endonuclease, comprising the sequence of SEQ ID NO: 6, wherein the nucleotide sequence is at least 95% identical to a nucleotide sequence of SEQ ID NO: 4; and
   a 3' untranslated region (UTR).

2. The mRNA of claim 1, wherein the mRNA comprises at least one chemically modified nucleoside.

3. The mRNA of claim 2, wherein the chemically modified nucleoside is selected from pseudouridine, N1-methylpseudouridine, and 5-methoxyuridine.

4. The mRNA of claim 2, wherein the chemically modified nucleoside is N1-methylpseudouridine.

5. The mRNA of claim 1, wherein at least about 80% of the uridines are chemically modified or replaced with N1-methylpseudouridine.

6. The mRNA of claim 1, wherein the 5' UTR comprises a nucleotide sequence of SEQ ID NO: 10 or SEQ ID NO: 15.

7. The mRNA of claim 1, wherein the 3' UTR comprises a nucleotide sequence of SEQ ID NO: 12.

8. The mRNA of claim 1, wherein the mRNA further comprises a poly-A tail.

9. The mRNA of claim 8, wherein the poly-A tail is about 100 to about 1000, about 10 to about 500, about 10 to about 300, about 10 to about 200, about 50 to about 150, about 100 to about 150, or about 120 to about 150 adenosine nucleotides.

10. The mRNA of claim 1, wherein the mRNA comprises the nucleotide sequence of SEQ ID NO: 2 or SEQ ID NO: 14.

11. An mRNA comprising a nucleotide sequence of SEQ ID NO: 2 or SEQ ID NO: 14, wherein 100% of the uridines of the mRNA are modified and/or replaced with N1-methylpseudouridine.

12. The mRNA of claim 1, wherein the mRNA comprises a 5' cap.

13. The mRNA of claim 1, wherein the 5' cap is a cap-0, a cap-1, or a cap-2 structure.

14. A pharmaceutical composition comprising:
   the mRNA of claim 1 and
   a pharmaceutically acceptable carrier.

15. A kit for inducing a DSB in a target gene in a cell, the kit comprising:
   a container comprising an mRNA of claim 1 and
   a package insert comprising instructions for use.

* * * * *